(12) United States Patent
Wan et al.

(10) Patent No.: US 11,597,968 B2
(45) Date of Patent: Mar. 7, 2023

(54) RIBONUCLEIC ACID (RNA) INTERACTIONS

(71) Applicant: Agency for Science, Technology and Research, Singapore (SG)

(72) Inventors: Yue Wan, Singapore (SG); Jong Ghut Ashley Aw, Singapore (SG); Niranjan Nagarajan, Singapore (SG); Andreas Wilm, Singapore (SG); Miao Sun, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 16/300,664

(22) PCT Filed: May 12, 2017

(86) PCT No.: PCT/SG2017/050254
§ 371 (c)(1),
(2) Date: Nov. 12, 2018

(87) PCT Pub. No.: WO2017/196264
PCT Pub. Date: Nov. 16, 2017

(65) Prior Publication Data
US 2019/0284622 A1  Sep. 19, 2019

(30) Foreign Application Priority Data

May 12, 2016 (SG) .......................... 10201603786V

(51) Int. Cl.
*C12Q 1/6869* (2018.01)
*C12Q 1/6806* (2018.01)
*C40B 50/00* (2006.01)

(52) U.S. Cl.
CPC ......... *C12Q 1/6869* (2013.01); *C12Q 1/6806* (2013.01); *C40B 50/00* (2013.01)

(58) Field of Classification Search
CPC ...... C12Q 1/6869; C12Q 1/6806; C40B 50/00
See application file for complete search history.

(56) References Cited

U.S. PATENT DOCUMENTS

| 2004/0175732 A1* | 9/2004 | Rana ...................... C12N 15/111 435/6.14 |
| 2015/0099671 A1* | 4/2015 | Moore ................ C12N 15/1096 506/26 |
| 2016/0040218 A1* | 2/2016 | Guttman .............. C12Q 1/6809 506/9 |

FOREIGN PATENT DOCUMENTS

| CN | 101410516 A | 4/2009 | |
| WO | 2014/152397 A2 | 9/2014 | |
| WO | 2014/152397 A3 | 9/2014 | |
| WO | 2016/048843 A1 | 3/2016 | |
| WO | WO 2016048843 | * 3/2016 | ............. C40B 30/04 |
| WO | 2017/196264 A1 | 11/2017 | |

OTHER PUBLICATIONS

Kudla et al. (PNAS Jun. 14, 2011 108 (24) 10010-10015, S1-S7).*
Nilsen (Abstract of: Cold Spring Harb Protoc. Sep. 2, 2014;2014(9):996-1000).*
PCT/SG2017/050254 received a Written Opinion of the International Searching Authority, dated Oct. 8, 2017, 6 pages.
PCT/SG2017/050254 received an International Search Report, dated Oct. 8, 2017, 6 pages.
Aw, J.G.A. et al., In Vivo mapping of eukaryotic RNA interactomes reveals principles of higher-order organization and regulation. *Mo/Cell*, May 12, 2016, vol. 62, No. 4, pp. 603-617.
Aw, J.G.A. et al., Mapping RNA-RNA interactions globally using biotinylated psoralen. *J Vis Exp*, May 24, 2017, No. 123, 3 pages.
Engreitz, J.M. et al., RNA-RNA interactions enable specific targeting of 1-26 noncoding RNAs to nascent pre-mRNAs and chromatin sites. *Cell*, Sep. 25, 2014, vol. 159, No. 1, pp. 189-199 <DOI: 10.1016/J.CELL.2014.08.018> Whole document.
Kudla, G. et al., Cross-linking, ligation, and sequencing of hybrids reveals 1-26 RNA-RNA interactions in yeast. *Proc Natl Acad Sci US A*, May 24, 2011, vol. 108, No. 24, p. 10010-10015 Whole document, particularly methods and results; fig 1A; section "Cross-Linking, Library Preparation, and Sequencing" in Supplemental Information.
Helwak, A. et al., Mapping the human miRNA interactome by CLASH reveals frequent noncanonical binding. *Cell*, Apr. 25, 2013, vol. 153, No. 3, 37 pages.
Liu, T. et al., Detecting RNA-RNA interactions in *E.coli* using a modified CLASH method. *BMC Genomics*, May 3, 2017, vol. 18, No. 1, pp. 343:1-11.
Lu, Z. et al., RNA duplex map in living cells reveals higher-order transcriptome structure, *cell*, May 12, 2016, vol. 165, No. 5, pp. 1267-1279.

(Continued)

*Primary Examiner* — Robert H Havlin
(74) *Attorney, Agent, or Firm* — Kilpatrick Townsend & Stockton LLP

(57) ABSTRACT

The invention relates to a method for analysing ribonucleic acid (RNA) interactions comprising: a) cross-linking base-paired nucleotides of at least one RNA molecule and/or at least one pair of RNA molecules using a tagged, reversible cross-linking agent (preferably tagged-psoralen) under ultra-violet irradiation; b) fragmenting the said cross-linked RNA molecule(s); c) using said tag to extract said cross-linked RNA fragment(s); d) ligating the said cross-linked RNA fragment(s) to produce cross-linked ligated RNA chimera (s); e) reversing the cross-linking of the said agent to the said RNA molecule(s); f) preparing a sequence library by sequencing the ligated RNA chimera molecule(s) or pair(s); and g) analysing the sequence library to determine RNA interactions. Also disclosed is a method of studying a subject by analysing RNA interactions and attributing them to a clinical picture, or a drug discovery method by attributing an efficacy score to the drug based upon determined RNA interactions.

Figure 1:
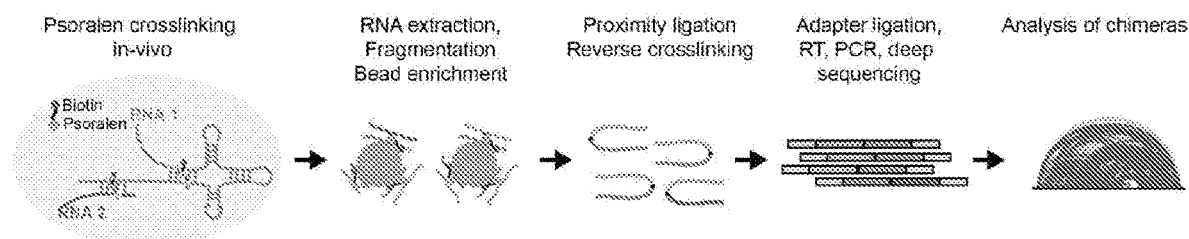
Figure 1:
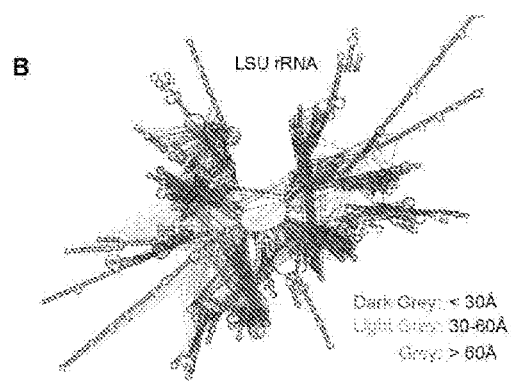
Figure 1:
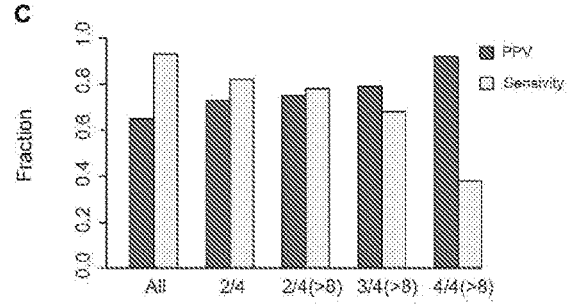

17 Claims, 14 Drawing Sheets
Specification includes a Sequence Listing.

(56) References Cited

OTHER PUBLICATIONS

Sharma, E. et al., Global mapping of human RNA-RNA interactions. *Mo/Cell*, May 12, 2016, vol. 62, No. 4, pp. 618-626.
De Vree; et al., "Targeted sequencing by proximity ligation for comprehensive variant detection and local haplotyping", Nature Biotechnology, vol. 32, No. 10, Oct. 2014, 9 pages.
EP 17796504 received a Supplementary European Search Report dated Apr. 12, 2019, 2 pages.
Singapore Application No. 11201809996Q received a Written Opinion dated Mar. 6, 2020, 7 pages.
China Application No. 201780043464.2 First Office Action dated Oct. 8, 2021, 14 pages, (7 pages original document, 7 pages English Translation).
Singapore Patent Application No. 11201809996Q received A Second Written Opinion dated Jun. 10, 2021, 8 pages.

* cited by examiner

A

B

C

A

Biotinylated psoralen

B

C

D

E

F

G

H

SEQUENCE LISTING

```
<160> NUMBER OF SEQ ID NOS: 74

<210> SEQ ID NO 1
<211> LENGTH: 17
<212> TYPE: DNA
<213> ORGANISM: Artificial Sequence
<220> FEATURE:
<223> OTHER INFORMATION: custom sequence

<400> SEQUENCE: 1
ctgtaggcac catcaat                                                    17

<210> SEQ ID NO 2
<211> LENGTH: 96
<212> TYPE: DNA
<213> ORGANISM: Artificial Sequence
<220> FEATURE:
<223> OTHER INFORMATION: custom sequence
<220> FEATURE:
<221> NAME/KEY: iSp18
<222> LOCATION: (49)..(50)
<223> OTHER INFORMATION: iSp18 position
<220> FEATURE:
<221> NAME/KEY: iSp18
<222> LOCATION: (55)..(56)
<223> OTHER INFORMATION: iSp18 position

<400> SEQUENCE: 2
agatcggaag agcgtcgtgt agggaaagag tgtagatctc ggtggtcgcc actcattcag     60
acgtgtgctc ttccgatcta ttgatggtgc ctacag                               96

<210> SEQ ID NO 3
<211> LENGTH: 20
<212> TYPE: DNA
<213> ORGANISM: Artificial Sequence
<220> FEATURE:
<223> OTHER INFORMATION: custom sequence

<400> SEQUENCE: 3
ctggcaggat caaccaggta                                                 20

<210> SEQ ID NO 4
<211> LENGTH: 20
<212> TYPE: DNA
<213> ORGANISM: Artificial Sequence
<220> FEATURE:
<223> OTHER INFORMATION: custom sequence

<400> SEQUENCE: 4
gggcggtggc tcgcctcgcg                                                 20

<210> SEQ ID NO 5
<211> LENGTH: 20
```

```
<212> TYPE: DNA
<213> ORGANISM: Artificial Sequence
<220> FEATURE:
<223> OTHER INFORMATION: custom sequence

<400> SEQUENCE: 5
tgacccgcac ttactgggaa                                                20

<210> SEQ ID NO 6
<211> LENGTH: 21
<212> TYPE: DNA
<213> ORGANISM: Artificial Sequence
<220> FEATURE:
<223> OTHER INFORMATION: custom sequence

<400> SEQUENCE: 6
aatgatcctt ccgcaggttc a                                              21

<210> SEQ ID NO 7
<211> LENGTH: 20
<212> TYPE: DNA
<213> ORGANISM: Artificial Sequence
<220> FEATURE:
<223> OTHER INFORMATION: custom sequence

<400> SEQUENCE: 7
acgtctgatc tgaggtcgcg                                                20

<210> SEQ ID NO 8
<211> LENGTH: 22
<212> TYPE: DNA
<213> ORGANISM: Artificial Sequence
<220> FEATURE:
<223> OTHER INFORMATION: custom sequence

<400> SEQUENCE: 8
tggtccgtgt ttcaagacgg gt                                             22

<210> SEQ ID NO 9
<211> LENGTH: 22
<212> TYPE: DNA
<213> ORGANISM: Artificial Sequence
<220> FEATURE:
<223> OTHER INFORMATION: custom sequence

<400> SEQUENCE: 9
caagacctct aatcattcgc tt                                             22

<210> SEQ ID NO 10
<211> LENGTH: 21
<212> TYPE: DNA
<213> ORGANISM: Artificial Sequence
<220> FEATURE:
<223> OTHER INFORMATION: custom sequence

<400> SEQUENCE: 10
tgtcgagggc tgactttcaa t                                              21

<210> SEQ ID NO 11
<211> LENGTH: 21
<212> TYPE: DNA
<213> ORGANISM: Artificial Sequence
<220> FEATURE:
<223> OTHER INFORMATION: custom sequence

<400> SEQUENCE: 11
```
tgcttagctt ccgagatcag a                    21

<210> SEQ ID NO 12
<211> LENGTH: 21
<212> TYPE: DNA
<213> ORGANISM: Artificial Sequence
<220> FEATURE:
<223> OTHER INFORMATION: custom sequence

<400> SEQUENCE: 12
aagcctacag cacccggtat t                    21

<210> SEQ ID NO 13
<211> LENGTH: 23
<212> TYPE: DNA
<213> ORGANISM: Artificial Sequence
<220> FEATURE:
<223> OTHER INFORMATION: custom sequence

<400> SEQUENCE: 13
gtaagaacac agcctgtggt aag                  23

<210> SEQ ID NO 14
<211> LENGTH: 20
<212> TYPE: DNA
<213> ORGANISM: Artificial Sequence
<220> FEATURE:
<223> OTHER INFORMATION: custom sequence

<400> SEQUENCE: 14
tcctctttct atacagtcag                      20

<210> SEQ ID NO 15
<211> LENGTH: 20
<212> TYPE: DNA
<213> ORGANISM: Artificial Sequence
<220> FEATURE:
<223> OTHER INFORMATION: custom sequence

<400> SEQUENCE: 15
atatggggta ggtttactct                      20

<210> SEQ ID NO 16
<211> LENGTH: 20
<212> TYPE: DNA
<213> ORGANISM: Artificial Sequence
<220> FEATURE:
<223> OTHER INFORMATION: custom sequence

<400> SEQUENCE: 16
gaggaaaagc gaagcgaggc                      20

<210> SEQ ID NO 17
<211> LENGTH: 20
<212> TYPE: DNA
<213> ORGANISM: Artificial Sequence
<220> FEATURE:
<223> OTHER INFORMATION: custom sequence

<400> SEQUENCE: 17
gcgaatgctt gtggaatgta                      20

<210> SEQ ID NO 18
<211> LENGTH: 20
<212> TYPE: DNA
<213> ORGANISM: Artificial Sequence

```
<220> FEATURE:
<223> OTHER INFORMATION: custom sequence

<400> SEQUENCE: 18
aacttgatcc aacctctttg                                                  20

<210> SEQ ID NO 19
<211> LENGTH: 20
<212> TYPE: DNA
<213> ORGANISM: Artificial Sequence
<220> FEATURE:
<223> OTHER INFORMATION: custom sequence

<400> SEQUENCE: 19
ggcaaacccg ttgcgaaaaa                                                  20

<210> SEQ ID NO 20
<211> LENGTH: 20
<212> TYPE: DNA
<213> ORGANISM: Artificial Sequence
<220> FEATURE:
<223> OTHER INFORMATION: custom sequence

<400> SEQUENCE: 20
tagttttcac gacacctgtg                                                  20

<210> SEQ ID NO 21
<211> LENGTH: 20
<212> TYPE: DNA
<213> ORGANISM: Artificial Sequence
<220> FEATURE:
<223> OTHER INFORMATION: custom sequence

<400> SEQUENCE: 21
accactgatt aagagtgggg                                                  20

<210> SEQ ID NO 22
<211> LENGTH: 20
<212> TYPE: DNA
<213> ORGANISM: Artificial Sequence
<220> FEATURE:
<223> OTHER INFORMATION: custom sequence

<400> SEQUENCE: 22
acatgatctg ggtcatcttc                                                  20

<210> SEQ ID NO 23
<211> LENGTH: 20
<212> TYPE: DNA
<213> ORGANISM: Artificial Sequence
<220> FEATURE:
<223> OTHER INFORMATION: custom sequence

<400> SEQUENCE: 23
ggatagcaca gcctggatag                                                  20

<210> SEQ ID NO 24
<211> LENGTH: 20
<212> TYPE: DNA
<213> ORGANISM: Artificial Sequence
<220> FEATURE:
<223> OTHER INFORMATION: custom sequence

<400> SEQUENCE: 24
atctcttgct cgaagtccag                                                  20
```

<210> SEQ ID NO 25
<211> LENGTH: 20
<212> TYPE: DNA
<213> ORGANISM: Artificial Sequence
<220> FEATURE:
<223> OTHER INFORMATION: custom sequence

<400> SEQUENCE: 25
tcattgccaa tggtgatgac                                               20

<210> SEQ ID NO 26
<211> LENGTH: 20
<212> TYPE: DNA
<213> ORGANISM: Artificial Sequence
<220> FEATURE:
<223> OTHER INFORMATION: custom sequence

<400> SEQUENCE: 26
ctcaggagga gcaatgatct                                               20

<210> SEQ ID NO 27
<211> LENGTH: 20
<212> TYPE: DNA
<213> ORGANISM: Artificial Sequence
<220> FEATURE:
<223> OTHER INFORMATION: custom sequence

<400> SEQUENCE: 27
cacattgtga actttggggg                                               20

<210> SEQ ID NO 28
<211> LENGTH: 20
<212> TYPE: DNA
<213> ORGANISM: Artificial Sequence
<220> FEATURE:
<223> OTHER INFORMATION: custom sequence

<400> SEQUENCE: 28
gacttcctgt aacaacgcat                                               20

<210> SEQ ID NO 29
<211> LENGTH: 20
<212> TYPE: DNA
<213> ORGANISM: Artificial Sequence
<220> FEATURE:
<223> OTHER INFORMATION: custom sequence

<400> SEQUENCE: 29
gtctcaagtc agtgtacagg                                               20

<210> SEQ ID NO 30
<211> LENGTH: 20
<212> TYPE: DNA
<213> ORGANISM: Artificial Sequence
<220> FEATURE:
<223> OTHER INFORMATION: custom sequence

<400> SEQUENCE: 30
acccatgttt agttaattat                                               20

<210> SEQ ID NO 31
<211> LENGTH: 20
<212> TYPE: DNA
<213> ORGANISM: Artificial Sequence
<220> FEATURE:
<223> OTHER INFORMATION: custom sequence

<400> SEQUENCE: 31
tcgacatgac cgataacgac                                               20

<210> SEQ ID NO 32
<211> LENGTH: 20
<212> TYPE: DNA
<213> ORGANISM: Artificial Sequence
<220> FEATURE:
<223> OTHER INFORMATION: custom sequence

<400> SEQUENCE: 32
accaccacac ttgtaaatca                                               20

<210> SEQ ID NO 33
<211> LENGTH: 20
<212> TYPE: DNA
<213> ORGANISM: Artificial Sequence
<220> FEATURE:
<223> OTHER INFORMATION: custom sequence

<400> SEQUENCE: 33
cacggattat ttgcctgatt                                               20

<210> SEQ ID NO 34
<211> LENGTH: 20
<212> TYPE: DNA
<213> ORGANISM: Artificial Sequence
<220> FEATURE:
<223> OTHER INFORMATION: custom sequence

<400> SEQUENCE: 34
attttgcgta acctattcgc                                               20

<210> SEQ ID NO 35
<211> LENGTH: 20
<212> TYPE: DNA
<213> ORGANISM: Artificial Sequence
<220> FEATURE:
<223> OTHER INFORMATION: custom sequence

<400> SEQUENCE: 35
ttagagggac aagtggcgtt                                               20

<210> SEQ ID NO 36
<211> LENGTH: 20
<212> TYPE: DNA
<213> ORGANISM: Artificial Sequence
<220> FEATURE:
<223> OTHER INFORMATION: custom sequence

<400> SEQUENCE: 36
ggacatctaa gggcatcaca                                               20

<210> SEQ ID NO 37
<211> LENGTH: 20
<212> TYPE: DNA
<213> ORGANISM: Artificial Sequence
<220> FEATURE:
<223> OTHER INFORMATION: custom sequence

<400> SEQUENCE: 37
gagaactttg aaggccgaag                                               20

<210> SEQ ID NO 38

<211> LENGTH: 20
<212> TYPE: DNA
<213> ORGANISM: Artificial Sequence
<220> FEATURE:
<223> OTHER INFORMATION: custom sequence

<400> SEQUENCE: 38
catctctcag gaccgactga					20

<210> SEQ ID NO 39
<211> LENGTH: 22
<212> TYPE: DNA
<213> ORGANISM: Artificial Sequence
<220> FEATURE:
<223> OTHER INFORMATION: custom sequence

<400> SEQUENCE: 39
gcgcccgatc tcgtctgatc tc				22

<210> SEQ ID NO 40
<211> LENGTH: 21
<212> TYPE: DNA
<213> ORGANISM: Artificial Sequence
<220> FEATURE:
<223> OTHER INFORMATION: custom sequence

<400> SEQUENCE: 40
caggcggtct cccatccaag t					21

<210> SEQ ID NO 41
<211> LENGTH: 22
<212> TYPE: DNA
<213> ORGANISM: Artificial Sequence
<220> FEATURE:
<223> OTHER INFORMATION: custom sequence

<400> SEQUENCE: 41
caggctgtgt tcttacactg ac				22

<210> SEQ ID NO 42
<211> LENGTH: 22
<212> TYPE: DNA
<213> ORGANISM: Artificial Sequence
<220> FEATURE:
<223> OTHER INFORMATION: custom sequence

<400> SEQUENCE: 42
atgttccccc attcacaata ca				22

<210> SEQ ID NO 43
<211> LENGTH: 21
<212> TYPE: DNA
<213> ORGANISM: Artificial Sequence
<220> FEATURE:
<223> OTHER INFORMATION: custom sequence

<400> SEQUENCE: 43
ggtcattacc aaggcttttta g				21

<210> SEQ ID NO 44
<211> LENGTH: 21
<212> TYPE: DNA
<213> ORGANISM: Artificial Sequence
<220> FEATURE:
<223> OTHER INFORMATION: custom sequence

<400> SEQUENCE: 44

-continued

| | |
|---|---|
| gcagatagaa aacctactgg g | 21 |

<210> SEQ ID NO 45
<211> LENGTH: 22
<212> TYPE: DNA
<213> ORGANISM: Artificial Sequence
<220> FEATURE:
<223> OTHER INFORMATION: custom sequence

<400> SEQUENCE: 45

| | |
|---|---|
| tcagagtgag cgctgggtac ag | 22 |

<210> SEQ ID NO 46
<211> LENGTH: 20
<212> TYPE: DNA
<213> ORGANISM: Artificial Sequence
<220> FEATURE:
<223> OTHER INFORMATION: custom sequence

<400> SEQUENCE: 46

| | |
|---|---|
| ggaaggcagt agagaatggt | 20 |

<210> SEQ ID NO 47
<211> LENGTH: 20
<212> TYPE: DNA
<213> ORGANISM: Artificial Sequence
<220> FEATURE:
<223> OTHER INFORMATION: custom sequence

<400> SEQUENCE: 47

| | |
|---|---|
| cgatatggct gagatcgaga | 20 |

<210> SEQ ID NO 48
<211> LENGTH: 20
<212> TYPE: DNA
<213> ORGANISM: Artificial Sequence
<220> FEATURE:
<223> OTHER INFORMATION: custom sequence

<400> SEQUENCE: 48

| | |
|---|---|
| ctttggaagg cagtggattt | 20 |

<210> SEQ ID NO 49
<211> LENGTH: 20
<212> TYPE: DNA
<213> ORGANISM: Artificial Sequence
<220> FEATURE:
<223> OTHER INFORMATION: custom sequence

<400> SEQUENCE: 49

| | |
|---|---|
| ctgtcaagga tgttcgtcgt | 20 |

<210> SEQ ID NO 50
<211> LENGTH: 20
<212> TYPE: DNA
<213> ORGANISM: Artificial Sequence
<220> FEATURE:
<223> OTHER INFORMATION: custom sequence

<400> SEQUENCE: 50

| | |
|---|---|
| cttatttggc ctggatggtt | 20 |

<210> SEQ ID NO 51
<211> LENGTH: 20
<212> TYPE: DNA

<213> ORGANISM: Artificial Sequence
<220> FEATURE:
<223> OTHER INFORMATION: custom sequence

<400> SEQUENCE: 51
tcgcaaagga tctccttcat                                        20

<210> SEQ ID NO 52
<211> LENGTH: 19
<212> TYPE: DNA
<213> ORGANISM: Artificial Sequence
<220> FEATURE:
<223> OTHER INFORMATION: custom sequence

<400> SEQUENCE: 52
ccaggcgttt cttcttgtg                                         19

<210> SEQ ID NO 53
<211> LENGTH: 20
<212> TYPE: DNA
<213> ORGANISM: Artificial Sequence
<220> FEATURE:
<223> OTHER INFORMATION: custom sequence

<400> SEQUENCE: 53
actctgcatt ctcgcttcct                                        20

<210> SEQ ID NO 54
<211> LENGTH: 20
<212> TYPE: DNA
<213> ORGANISM: Artificial Sequence
<220> FEATURE:
<223> OTHER INFORMATION: custom sequence

<400> SEQUENCE: 54
ctcgtttgta cccgttgatg                                        20

<210> SEQ ID NO 55
<211> LENGTH: 20
<212> TYPE: DNA
<213> ORGANISM: Artificial Sequence
<220> FEATURE:
<223> OTHER INFORMATION: custom sequence

<400> SEQUENCE: 55
tggtatcgtg gaaggactca                                        20

<210> SEQ ID NO 56
<211> LENGTH: 20
<212> TYPE: DNA
<213> ORGANISM: Artificial Sequence
<220> FEATURE:
<223> OTHER INFORMATION: custom sequence

<400> SEQUENCE: 56
ccagtagagg cagggatgat                                        20

<210> SEQ ID NO 57
<211> LENGTH: 19
<212> TYPE: DNA
<213> ORGANISM: Artificial Sequence
<220> FEATURE:
<223> OTHER INFORMATION: custom sequence

<400> SEQUENCE: 57
agagaggcat cctcaccct                                         19

<210> SEQ ID NO 58
<211> LENGTH: 20
<212> TYPE: DNA
<213> ORGANISM: Artificial Sequence
<220> FEATURE:
<223> OTHER INFORMATION: custom sequence

<400> SEQUENCE: 58
cacacgcagc tcattgtaga                                               20

<210> SEQ ID NO 59
<211> LENGTH: 20
<212> TYPE: DNA
<213> ORGANISM: Artificial Sequence
<220> FEATURE:
<223> OTHER INFORMATION: custom sequence

<400> SEQUENCE: 59
gaaggaggag ctgctgaaac                                               20

<210> SEQ ID NO 60
<211> LENGTH: 21
<212> TYPE: DNA
<213> ORGANISM: Artificial Sequence
<220> FEATURE:
<223> OTHER INFORMATION: custom sequence

<400> SEQUENCE: 60
tcggatctta gagagcttgg a                                             21

<210> SEQ ID NO 61
<211> LENGTH: 20
<212> TYPE: DNA
<213> ORGANISM: Artificial Sequence
<220> FEATURE:
<223> OTHER INFORMATION: custom sequence

<400> SEQUENCE: 61
gactttgtca cagcccaaga                                               20

<210> SEQ ID NO 62
<211> LENGTH: 20
<212> TYPE: DNA
<213> ORGANISM: Artificial Sequence
<220> FEATURE:
<223> OTHER INFORMATION: custom sequence

<400> SEQUENCE: 62
caagcaagca gaatttggaa                                               20

<210> SEQ ID NO 63
<211> LENGTH: 20
<212> TYPE: DNA
<213> ORGANISM: Artificial Sequence
<220> FEATURE:
<223> OTHER INFORMATION: custom sequence

<400> SEQUENCE: 63
gaatcagaaa gcggtggatt                                               20

<210> SEQ ID NO 64
<211> LENGTH: 19
<212> TYPE: DNA
<213> ORGANISM: Artificial Sequence
<220> FEATURE:

<223> OTHER INFORMATION: custom sequence

<400> SEQUENCE: 64
accagaccag ggatgagtg                                                    19

<210> SEQ ID NO 65
<211> LENGTH: 23
<212> TYPE: DNA
<213> ORGANISM: Artificial Sequence
<220> FEATURE:
<223> OTHER INFORMATION: custom sequence

<400> SEQUENCE: 65
catgggtaaa gagaagtctc aca                                               23

<210> SEQ ID NO 66
<211> LENGTH: 22
<212> TYPE: DNA
<213> ORGANISM: Artificial Sequence
<220> FEATURE:
<223> OTHER INFORMATION: custom sequence

<400> SEQUENCE: 66
ggttctcttg tcaataccac ca                                                22

<210> SEQ ID NO 67
<211> LENGTH: 21
<212> TYPE: DNA
<213> ORGANISM: Artificial Sequence
<220> FEATURE:
<223> OTHER INFORMATION: custom sequence

<400> SEQUENCE: 67
gattcgctgt cagagacatg a                                                 21

<210> SEQ ID NO 68
<211> LENGTH: 20
<212> TYPE: DNA
<213> ORGANISM: Artificial Sequence
<220> FEATURE:
<223> OTHER INFORMATION: custom sequence

<400> SEQUENCE: 68
cagccttggt aaccttagcg                                                   20

<210> SEQ ID NO 69
<211> LENGTH: 20
<212> TYPE: DNA
<213> ORGANISM: Artificial Sequence
<220> FEATURE:
<223> OTHER INFORMATION: custom sequence

<400> SEQUENCE: 69
gagaaggatg tggtccgagt                                                   20

<210> SEQ ID NO 70
<211> LENGTH: 20
<212> TYPE: DNA
<213> ORGANISM: Artificial Sequence
<220> FEATURE:
<223> OTHER INFORMATION: custom sequence

<400> SEQUENCE: 70
gtgcatagtc gctgcttgat                                                   20

```
<210> SEQ ID NO 71
<211> LENGTH: 20
<212> TYPE: DNA
<213> ORGANISM: Artificial Sequence
<220> FEATURE:
<223> OTHER INFORMATION: custom sequence

<400> SEQUENCE: 71
gctggtaggg agtcagaagg                                                   20

<210> SEQ ID NO 72
<211> LENGTH: 20
<212> TYPE: DNA
<213> ORGANISM: Artificial Sequence
<220> FEATURE:
<223> OTHER INFORMATION: custom sequence

<400> SEQUENCE: 72
ttggtttcct tcctggagtt                                                   20

<210> SEQ ID NO 73
<211> LENGTH: 20
<212> TYPE: DNA
<213> ORGANISM: Artificial Sequence
<220> FEATURE:
<223> OTHER INFORMATION: custom sequence

<400> SEQUENCE: 73
tcaagaaggt ggtgaagcag                                                   20

<210> SEQ ID NO 74
<211> LENGTH: 20
<212> TYPE: DNA
<213> ORGANISM: Artificial Sequence
<220> FEATURE:
<223> OTHER INFORMATION: custom sequence

<400> SEQUENCE: 74
cgctgttgaa gtcagaggag                                                   20
```

RIBONUCLEIC ACID (RNA) INTERACTIONS

CROSS-REFERENCE TO RELATED APPLICATIONS

The present application is a national phase of PCT International Application Number PCT/SG2017/050254, filed on May 12, 2017, which claims the benefit of Singapore Patent Application Number 10201603786V, filed on May 12, 2016. Each of these applications is hereby incorporated by reference in its entirety for all purposes.

The invention relates to a method for analysing ribonucleic acid (RNA) interactions comprising cross-linking base-paired nucleotides of at least one RNA molecule and/or at least one pair of RNA molecules using a tagged reversible cross-linking agent; a kit for analysing ribonucleic acid (RNA) interactions comprising at least said tagged reversible cross-linking agent; a method of studying a subject using the said method and/or kit; and a drug discovery method using the said method and/or kit.

BACKGROUND OF INVENTION

The ability of an RNA to base pair with itself and with others is crucial for its function in vivo. RNA carries information in both its linear sequence and its secondary and tertiary structure. While significant advances have been made to map RNA secondary structures genome-wide, understanding how different parts of an RNA interact to form higher order structures requires considerable pairwise structural information. RNA's ability to interact with other RNAs, such as miRNA-mRNA and lncRNA-mRNA interactions, plays an important role in post-transcriptional gene regulation. However, the global prevalence and dynamics of RNA interaction networks and their impact on gene regulation is still largely unknown. As such, mapping RNA structure and interactomes in different cellular states is crucial to expanding our understanding of RNA function.

To identify which two RNA regions are interacting with each other, we need spatial connectivity information to link nucleotides that are physically pairing. Numerous RNA cross-linkers, including methylene blue, UV and psoralen, have been used to connect far away interacting regions of RNAs to each other. However, the readout for these strategies has typically been slow and tedious. Alternative strategies for identifying pairwise interactions have utilized sequence mutations followed by structure probing to detect base pairing partners within an RNA. These approaches are higher throughput, but are not amenable to studying whole genomes. Recent strategies such as CLASH, Hi-CLIP and RAP have leveraged on high-throughput sequencing to identify subpopulations of RNA interactions that are associated with a specific RNA binding protein or RNA species. A recent proximity ligation based approach, RPL, has also been used to identify stems in the transcriptome in a non-selective manner. However, RPL does not utilize cross-linking to identify stable interactions and is mostly limited to mapping intramolecular RNA interactions.

We herein disclose a high-throughput methodology, termed Sequencing of Psoralen crosslinked, Ligated, and Selected Hybrids (SPLASH), that maps pairwise RNA interactions in-vivo with high sensitivity and specificity, genome-wide. Applying SPLASH to human and yeast transcriptomes permits the diversity and dynamics of thousands of long-range intra and intermolecular RNA-RNA interactions to be studied. This, for example, permitted analysis that highlighted key structural features of RNA classes, including the modular organization of mRNAs, its impact on translation and decay, and the enrichment of long-range interactions in non-coding RNAs. Additionally, intermolecular mRNA interactions were organized into network clusters and were remodelled during cellular differentiation. Also, it allowed identification of hundreds of known and new snoRNA-rRNA binding sites, expanding the knowledge base of rRNA biogenesis. These results highlight the underexplored complexity of RNA interactomes and paves the way to better understand how RNA organization impacts biology.

STATEMENTS OF INVENTION

According to a first aspect of the invention there is provided a method for analysing ribonucleic acid (RNA) interactions comprising:
  a. cross-linking base-paired nucleotides of at least one RNA molecule and/or at least one pair of RNA molecules using a tagged, reversible cross-linking agent to produce at least one cross-linked RNA molecule and/or at least one pair of cross-linked RNA molecules;
  b. fragmenting the said cross-linked RNA molecule and/or pair of cross-linked RNA molecules to produce a plurality of fragments comprising at least one cross-linked RNA fragment;
  c. using said tag to extract said cross-linked RNA fragment(s) from said plurality of fragments;
  d. ligating the said cross-linked RNA fragment(s) to produce cross-linked ligated RNA chimera(s);
  e. reversing the cross-linking of the said agent to the said RNA molecule and/or pair of RNA molecules to produce a ligated RNA chimera molecule(s) and/or RNA chimera pair(s);
  f. preparing a sequence library by sequencing the ligated RNA chimera molecule(s) or pair(s); and
  g. analysing the sequence library to determine RNA interactions.

In a preferred method of the invention said RNA is present in a cell and said cross-linking using said tagged, reversible cross-linking agent involves the use of a cellular uptake agent, such as a detergent. Ideally, the detergent is digitonin and preferably used at a concentration of 0.01% or thereabouts. In this embodiment of the invention, said RNA is extracted from said cell prior to performing the fragmentation step of part b.

Those skilled in the art will appreciate that when working the invention part c may be undertaken before or after part b.

In a preferred method of the invention said cross-linking agent comprises a furocoumarin compound, ideally, psoralen. We have found that psoralen intercalates into base-paired regions independently of whether they are formed by the same RNA strand, or between two different RNA strands, enabling SPLASH to interrogate both intra- and inter-molecular RNA interactions.

Psoralen (also called psoralene) is the parent compound in a family of natural products known as furocoumarins. It is structurally related to coumarin by the addition of a fused furan ring, and may be considered as a derivative of umbelliferone. Practising the invention herein described may involve the use of any one or more of these compounds. Advantageously, these furocoumarins are capable of reversibly and/or selectively cross-linking nucleotides.

In yet a further preferred method of the invention said tag of said cross-linking agent comprises a first member of a binding pair. Ideally, said tag is one member of one of the"

following binding pairs: biotin/streptavidin, antigen/antibody, protein/protein, polypeptide/protein and polypeptide/polypeptide. Accordingly, using said tag to extract said cross-linked RNA fragment from said plurality of fragments involves the use of the other member of said binding pair which may, optionally, be provided on a support.

More preferably still, the cross-linking of said RNA molecule(s) with said cross-linking agent to produce cross-linked RNA molecule(s) is carried out using ultraviolet irradiation at wavelengths in the range of about 300 nm to about 400 nm. Similarly, reversing the cross-linking of the cross-linked ligated RNA molecule(s) is carried out using ultraviolet irradiation at a different wavelength i.e. in the range of about 200 nm to no more than about 300 nm.

Preferably, the method step of preparing a sequence library by sequencing the ligated RNA chimera molecule(s) or pair(s) comprises the use of at least one or more of the following techniques: adaptor ligation, reverse transcription, cDNA circularization or polymerase chain reaction (PCR).

In a preferred method of the invention, the step of fragmenting the cross-linked RNA molecule and/or pair of RNA molecules to produce a plurality of fragments comprises producing fragments having an average size in the range of 100 to 500 base pairs in length. Conventional means or agents for fragmenting RNA are used in the method of the invention, such as physical, chemical or enzymatic means including but not limited to acoustic shearing, sonication, hydrodynamic shearing, DNase or ribonuclease treatment, transposase treatment, and heat digestion with a divalent metal cation.

Ideally, when practising the method of the invention, the concentration of cross-linking agent used is calibrated such that it crosslinks at approximately one in every 150 bases.

Ideally, when analysing the sequence library continuous pairwise interactions or those spaced apart by less than 50 bases are removed, this enables one to focus the analysis on the long-range intramolecular and intermolecular interactions.

In yet a further preferred method of the invention said RNA molecule and/or at least one member of said pair of RNA molecules is ascribed a "circularization score" defined as the average base pair interaction distance within each molecule, normalized by the length of said RNA molecule or the length of said member of said pair of RNA molecules. More ideally still, when analysing the sequence library said RNA molecule and/or said at least one member of said pair of RNA molecules are classified into groups according to their "circularization score".

Reference herein to circularization score is reference to the propensity of RNA to form long-range pairwise interactions which we have found to be related to translation efficiency. Indeed, we have discovered that transcripts with high circularization scores tend to be translated better than those with low circularization scores, moreover, these scores can change as the corresponding RNA, particularly mRNA, undergoes conformational change. For example, mRNAs that shift from having a high circularization score in ES (stem) cells to a low circularization score in RA (differentiated) cells showed a corresponding decrease in translation efficiency and vice versa (FIG. 7A). This shows that conformational changes can serve as an underlying mechanism to control translation efficiency during changes in cellular states. For example, one of the chromatin genes, high mobility group 1, HMGA1, exhibited a notable decrease in circularization score and translation efficiency during RA differentiation, consistent with its key role in maintaining ES cell pluripotency (FIG. 7B). Corroboratively, protein and mRNA quantification using western blot and qPCR analysis showed that HMGA1 protein levels decrease after 5 days of differentiation, whereas its mRNA levels do not (FIG. 7C, D). Furthermore, translation efficiency, measured by ribosome profiling in mouse ES and differentiated cells, showed a corresponding decrease in HMGA1 translation efficiency upon cellular differentiation (FIG. 14H), reinforcing the association between structural rearrangement and translation.

In yet a further preferred method of the invention the cell is mammalian, human, bacterial or yeast.

Most typically, analysing the sequence library to determine RNA interactions comprises processing data derived from the sequence library through one or more computational blocks to determine RNA interactions. Most preferably, the one or more computational blocks is/are selected from the group consisting of: a computational block for filtering reads from adaptor RNAs; a computational block for filtering reads from PCR duplicates; a computational block for merging paired-end reads into single reads; a computational block for filtering reads from split alignments less than a predetermined number of base pairs apart; a computational block for filtering reads from splicing related false positives interactions; a computational block for filtering reads of co-transcribed transcripts relating to intermolecular interactions; a computational block for binning and filtering of data relating to interacting RNA pairs; and indeed any combination of the afore blocks.

Ideally, the computational block for filtering reads from split alignments less than a predetermined number of base pairs apart comprises filtering reads from split alignments less than 50 bases pairs apart.

Typically, the invention can be used so that the RNA interactions determined provide useful information relating to, amongst other things, intermolecular RNA interaction, intramolecular RNA interaction, primary RNA structure, secondary RNA structure, tertiary RNA structure, quaternary RNA structure, gene regulation, gene expression, gene translation efficiency, RNA decay rates, metabolites responsive to RNA elements and ribosome biogenesis.

Most advantageously, the method of the invention is indiscriminate in analysing RNA interactions genome-wide and is not limited to analysing RNA interactions associated with a specific RNA binding protein or RNA species.

In yet a further aspect, the invention concerns a kit for analysing ribonucleic acid (RNA) interactions comprising:
  a tagged, reversible cross-linking agent for reversibly cross-linking base paired nucleotides of at least one RNA molecule and/or at least one pair of RNA molecules to produce at least one cross-linked RNA molecule and/or at least one pair of cross-linked RNA molecules;
  a fragmentation buffer for fragmenting the said cross-linked RNA molecule and/or said pair of cross-linked RNA molecules to produce a plurality of fragments;
  an RNA ligase for ligating the cross-linked RNA fragment(s) to produce cross-linked ligated RNA chimera(s);
  a binding partner for said tag on said agent; and
  optionally, instructions on how to use the kit.

Preferably, the kit further comprising reagents for sequencing the cross-linked ligated RNA chimera(s) to prepare a sequence library. Ideally, the kit comprises at least one of a RNA ligase, reverse transcription primers and DNA polymerase.

Most preferably, the cross-linking agent comprises a furocoumarin compound, such as psoralen.

Additionally, said tag of said cross-linking agent comprises a first member of a binding pair. Ideally, said tag is one member of one of the following binding pairs: biotin/streptavidin, antigen/antibody, protein/protein, polypeptide/protein and polypeptide/polypeptide. Accordingly, using said tag to extract said cross-linked RNA fragment from said plurality of fragments involves the use of said binding partner, or the other member of said binding pair, which may, optionally, be provided on a support.

More preferably still, the kit further comprises an agent to facilitate cellular uptake of the cross-linking agent into a cell such as a detergent, an example of which is a mild detergent such as digitonin, and used at about 0.01%.

According to a further aspect of the invention there is provided a method of studying a subject, the method comprising:
 a. obtaining a cell sample from a subject;
 b. cross-linking base-paired nucleotides of at least one RNA molecule and/or at least one pair of RNA molecules using a tagged, reversible cross-linking agent to produce at least one cross-linked RNA molecule and/or at least one pair of cross-linked RNA molecules;
 c. fragmenting the said cross-linked RNA molecule and/or pair of cross-linked RNA molecules to produce a plurality of fragments comprising at least one cross-linked RNA fragment;
 d. using said tag to extract said cross-linked RNA fragment(s) from said plurality of fragments;
 e. ligating the said cross-linked RNA fragment(s) to produce cross-linked ligated RNA chimera(s);
 f. reversing the cross-linking of the said agent to the said RNA molecule and/or pair of RNA molecule(s) to produce ligated a RNA chimera molecule(s) and/or RNA chimera pair(s);
 g. preparing a sequence library by sequencing the ligated RNA chimera molecule(s) or pair(s);
 h. analysing the sequence library to determine RNA interactions in the cell sample; and
 i. comparing the determined RNA interactions with a set of pre-existing data to attribute a clinical picture to the subject.

In this preferred method of the invention, the method of studying a subject comprises at least one of: diagnosing the subject of a clinical condition, predicting the risk of the subject having a clinical condition, screening the subject for suitability for a particular treatment or determining the efficacy of a drug candidate on the subject.

According to a yet further aspect of the invention there is provided a drug discovery method, the method comprising:
 a. exposing RNA to a drug;
 b. cross-linking base-paired nucleotides of at least one RNA molecule and/or at least one pair of RNA molecules using a tagged, reversible cross-linking agent to produce at least one cross-linked RNA molecule and/or at least one pair of cross-linked RNA molecules;
 c. fragmenting the said cross-linked RNA molecule and/or pair of cross-linked RNA molecules to produce a plurality of fragments comprising at least one cross-linked RNA fragment;
 d. using said tag to extract said cross-linked RNA fragment(s) from said plurality of fragments;
 e. ligating the said cross-linked RNA fragment(s) to produce cross-linked ligated RNA chimera(s);
 f. reversing the cross-linking of the said agent to the said RNA molecule and/or pair of RNA molecules to produce a ligated a RNA chimera molecule(s) and/or RNA chimera pair(s);
 g. preparing a sequence library by sequencing the ligated RNA chimera molecule(s) or pair(s);
 h. analysing the sequence library to determine RNA interactions; and
 i. attributing an efficacy score to the drug based on the determined RNA interactions.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, corn pounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

The invention will now be described, by way of example only, with reference to the following figures and tables wherein:—

Figure 2:
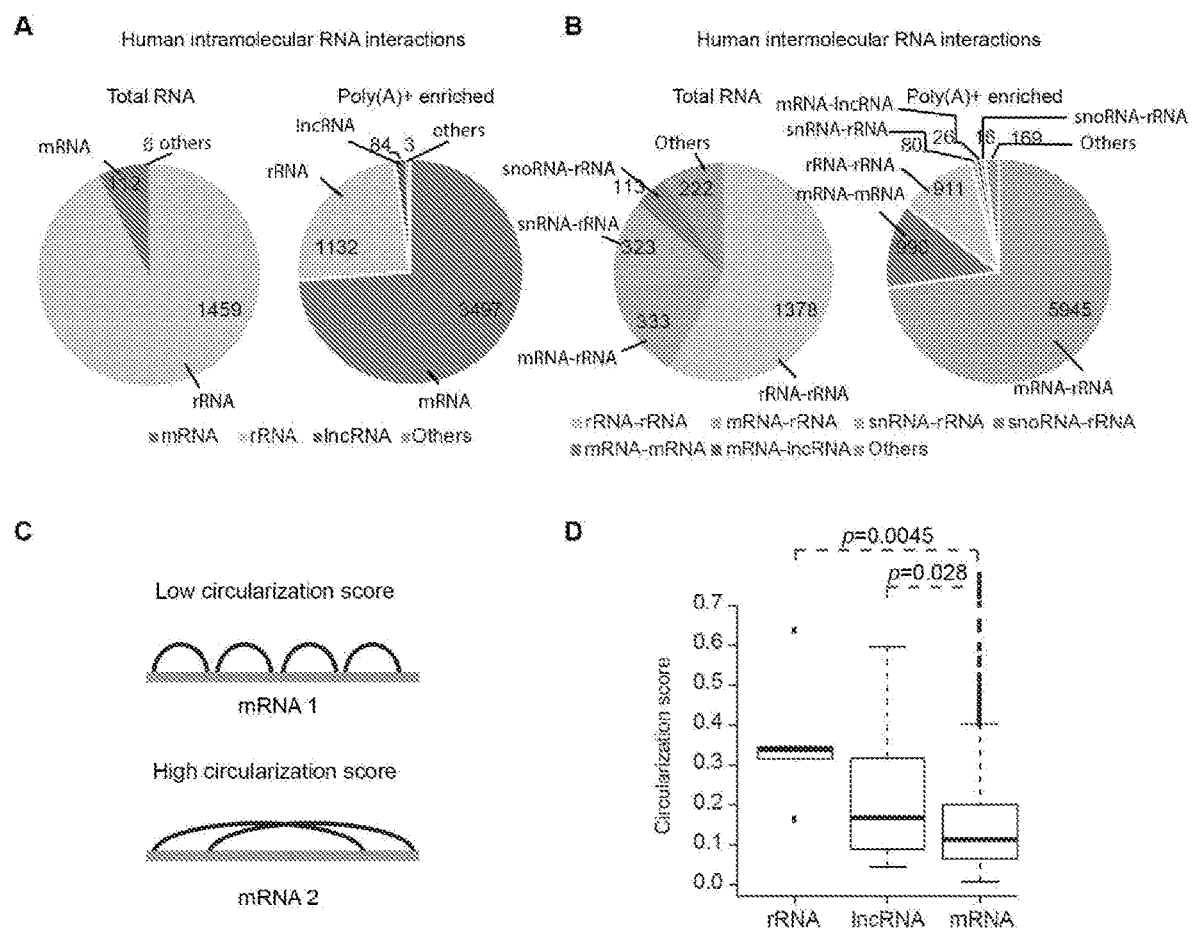
Figure 3:
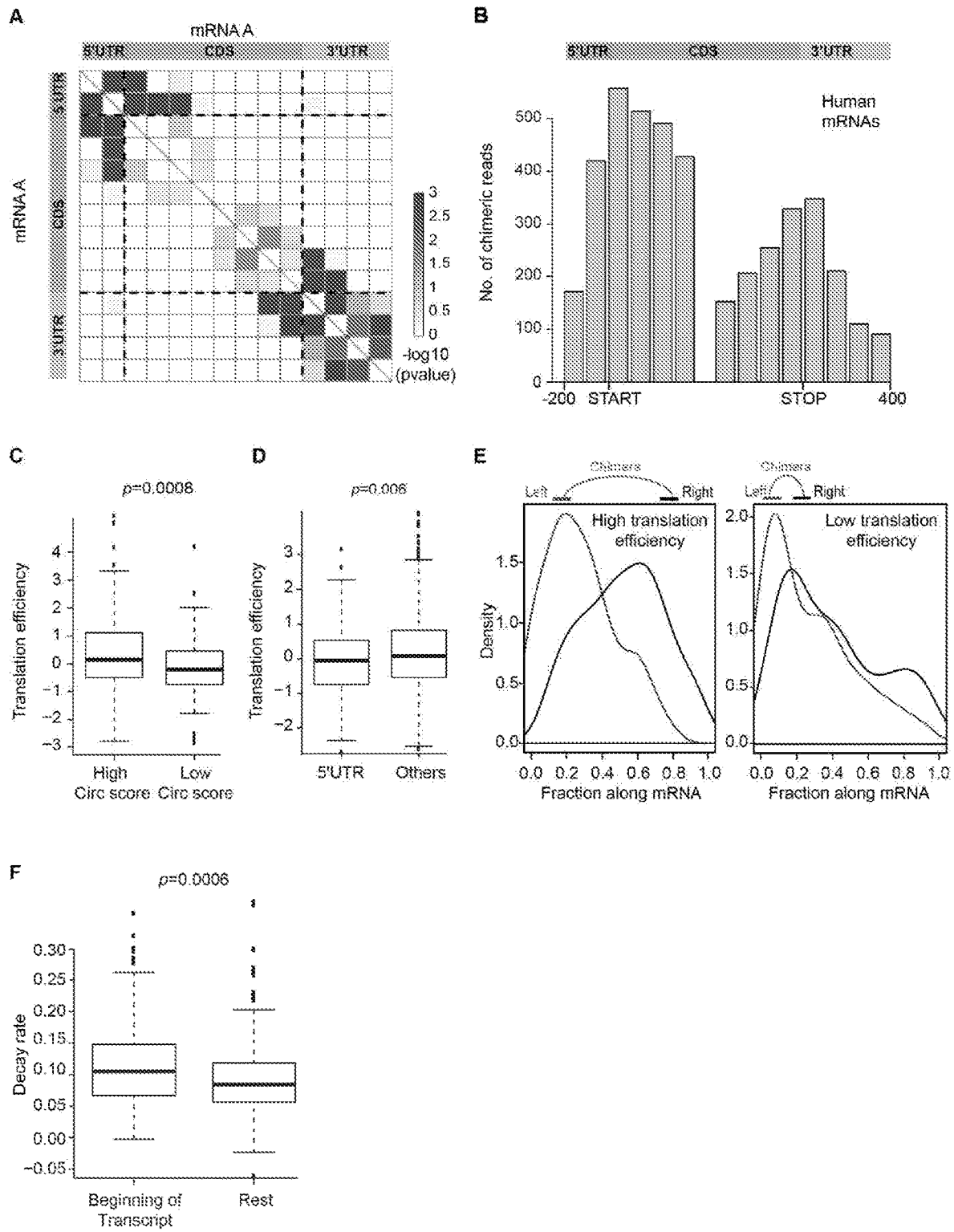
Figure 4:
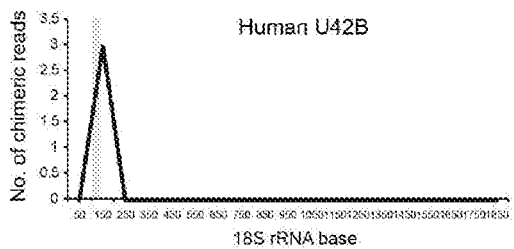
Figure 4:
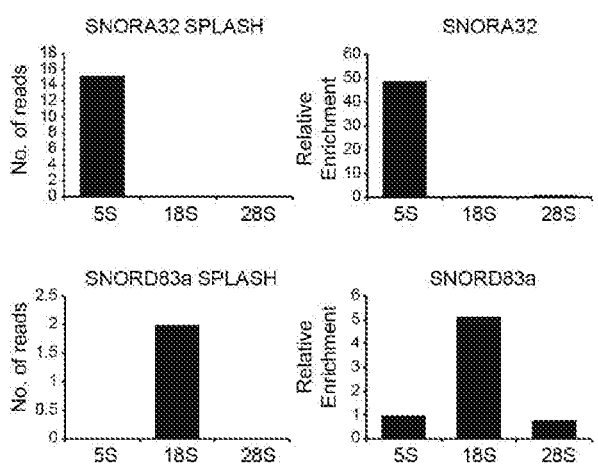
Figure 4:
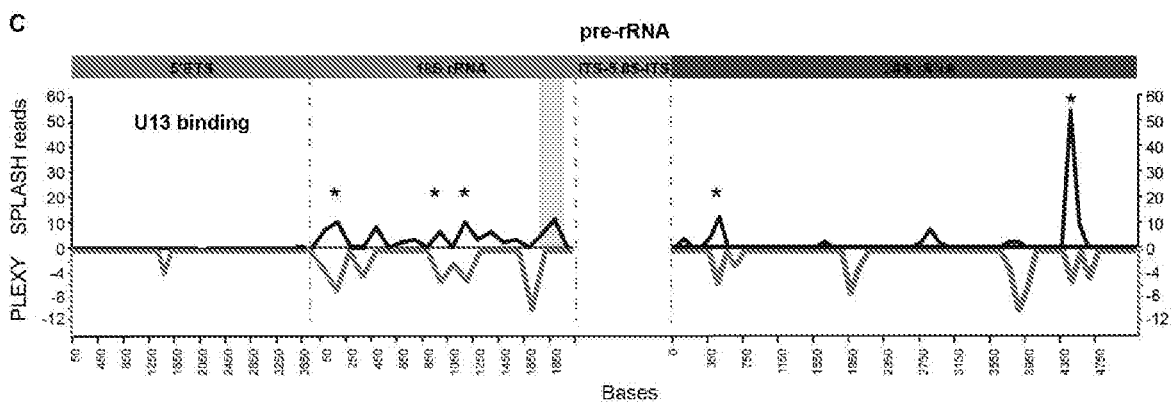
Figure 4:
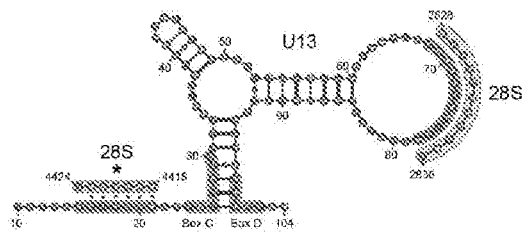
Figure 5:
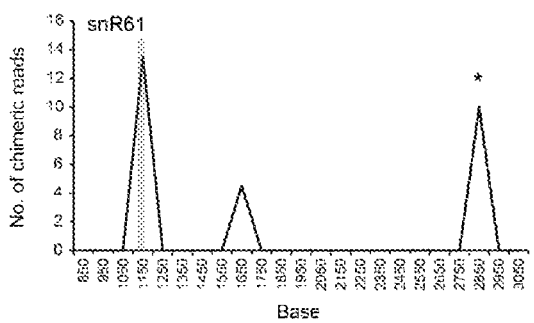
Figure 5:
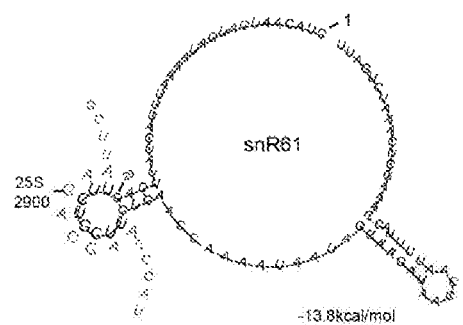
Figure 5:
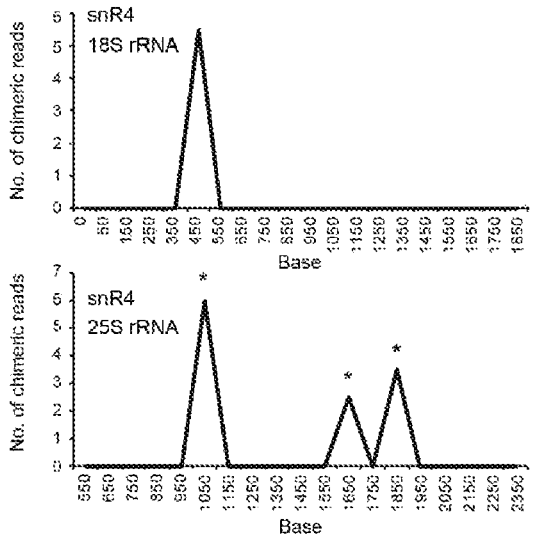
Figure 5:
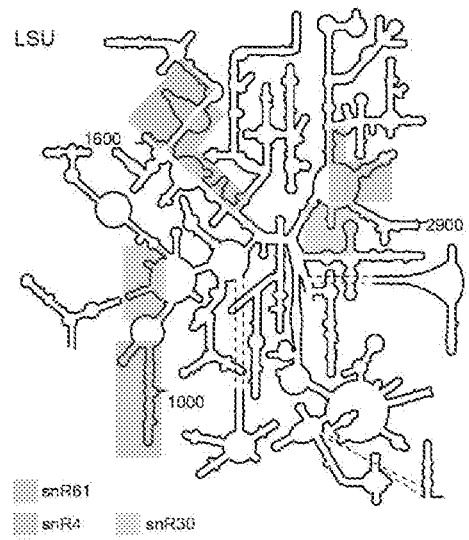
Figure 5:
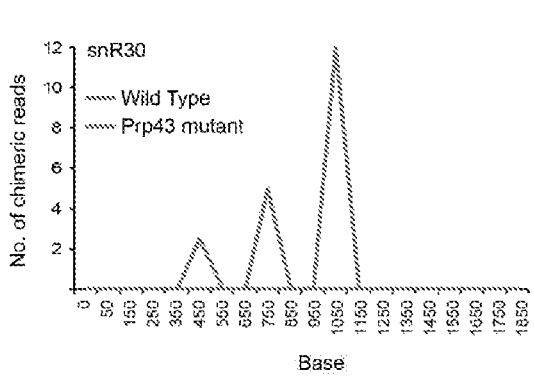
Figure 5:
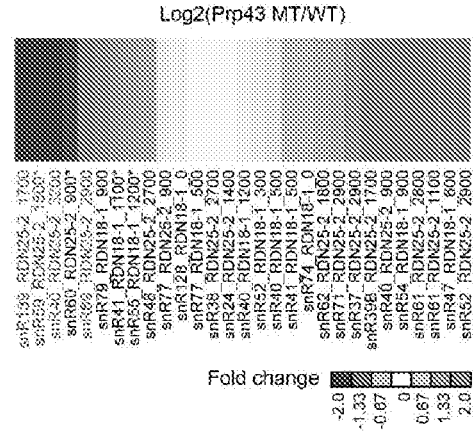
Figure 6:
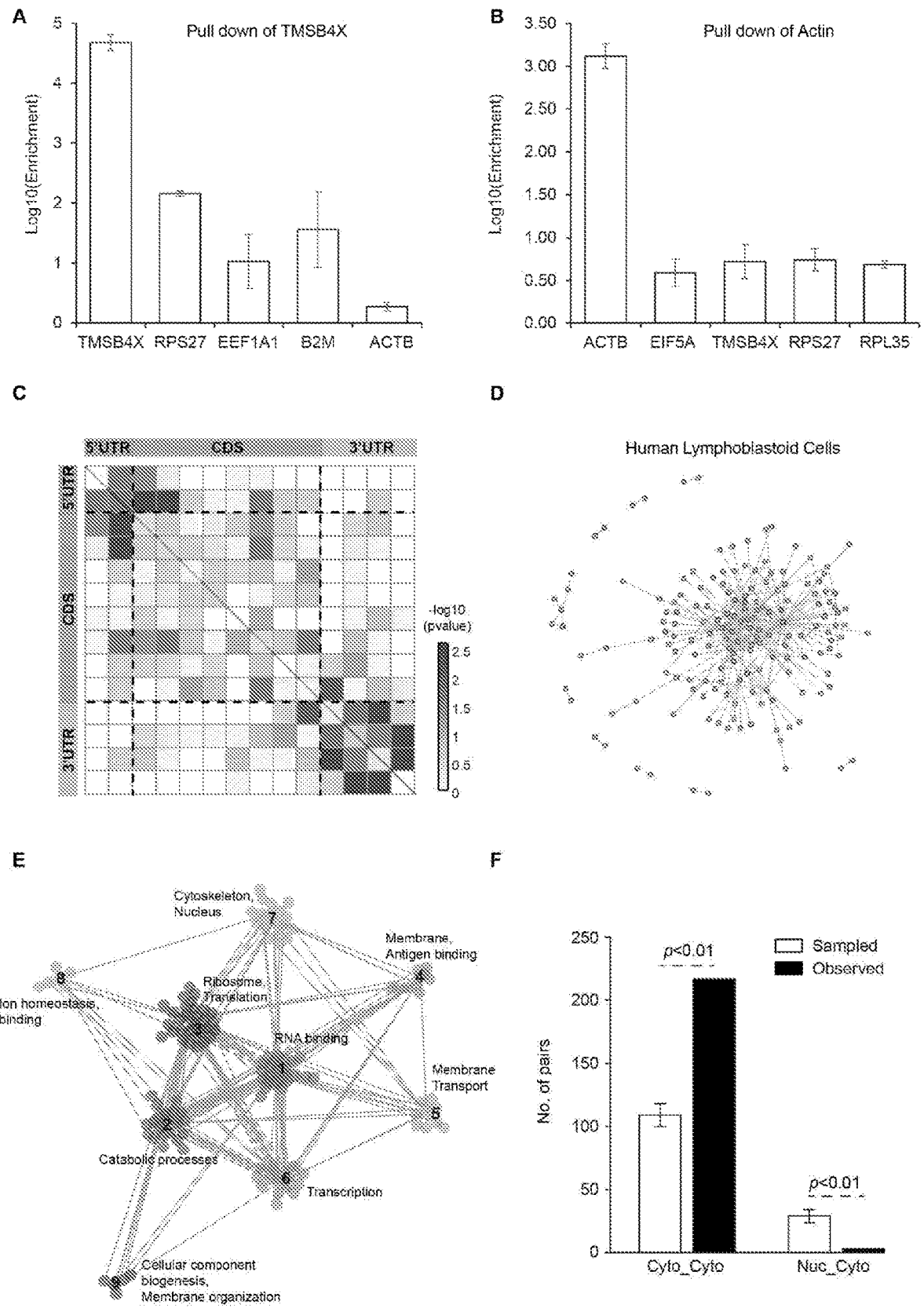
Figure 7:
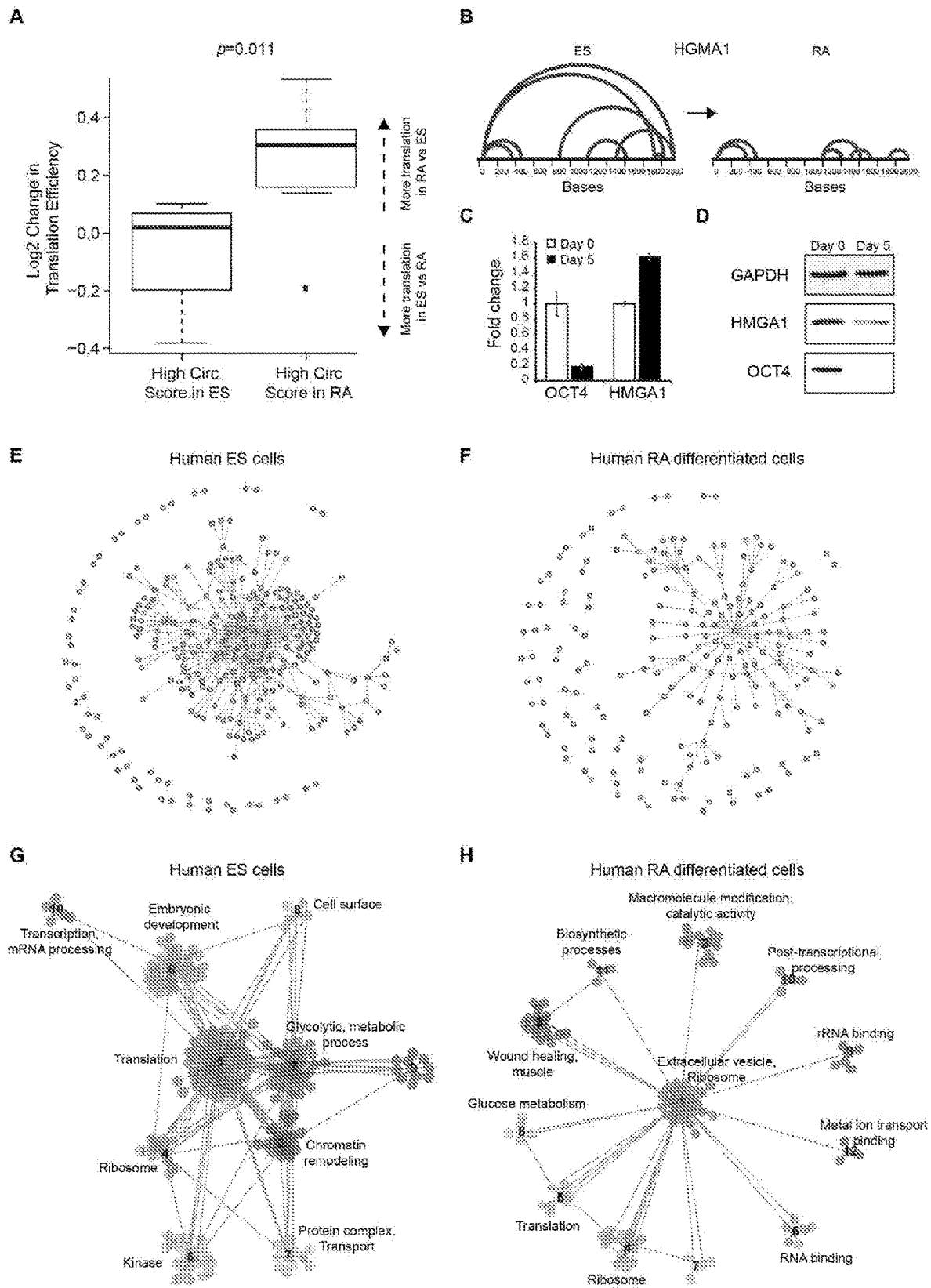

FIG. 1. SPLASH strategy identifies RNA interactions accurately. [A] Schematic of the SPLASH strategy. RNA-RNA interactions are crosslinked in vivo using biotinylated psoralen (biopsoralen) and then fragmented. Interacting regions that contain bio-psoralen are enriched by binding to streptavidin beads and ligated together. Chimeric RNAs are then cloned into a cDNA library for deep sequencing. [B] Visualization of chimeric interactions on the secondary structure of the 28S rRNA. The dark grey, light grey and grey lines represent interactions <30 Å apart, 30-60 Å apart, and >60 Å apart respectively, based on the 80S ribosome crystal structure. [C] Bar chart showing positive predictive value (PPV) and sensitivity in total RNA replicates, based on the 80S rRNA crystal structure, at different cut-offs. The cut-off "All" indicates interactions that exist in at least one out of the four biological replicates, while "2/4", "3/4" and "4/4" indicates interactions that are present in at least 2, 3 or 4 replicates. The notation ">8" indicates that the interaction needs to be supported by at least 8 chimeric reads across the libraries. See also FIG. 8, 9, Table 1;

FIG. 2. Distribution and function of the human RNA interactome. [A, B], Pie charts showing the distribution of intramolecular [A] and intermolecular [B] interactions belonging to different classes of transcripts in four biological replicates of total RNA (Left) and in all polyA(+) enriched RNA samples (Right). [C] Schematic of the circularization score. The circularization score is calculated as the average span of intramolecular interactions normalized by mRNA length. mRNAs with higher circularization score participate in more long-range interactions. [D] Boxplot of circularization scores for rRNAs, lncRNAs and mRNAs. P-values are calculated using Wilcoxon rank sum test. See also FIG. 10, 11, Table 2;

FIG. 3. Intramolecular interaction patterns and their association with gene regulation. [A] Two-dimensional heat map showing enrichment of intramolecular mRNA interactions based on the location of chimera ends. We aligned transcripts according to their translation start and stop sites and plotted interactions from the last 200 bases of the 5' UTR, the first and last 400 bases of the coding region, and the first 400 bases of the 3' UTR. Enrichment was calculated as –log 10 (p-value) based on random sampling across the transcript with 100 bp windows. The black dotted lines demarcate boundaries between the 5' UTR, CDS and 3' UTR. [B] Metagene analysis of the frequency of intramolecular interactions along human mRNAs, by aligning mRNAs along their translation start and stop. We plotted interactions that are present in the last 200 bases of the 5' UTR, first and last 400 bases of the coding region and the first 400 bases of the 3' UTR. [C] Boxplot of translation efficiency (Y-axis) in mRNAs with the highest and lowest 20% circularization scores. [D] Boxplot of translation efficiency in mRNAs that have interactions only in the 5' UTRs, versus mRNAs with interactions all over the transcript. [E] Density plot showing the distribution of the left (grey) and right (black) end of a pairwise interaction for top 5% of mRNAs that are translated efficiently (Left plot) and poorly (Right plot) based on ribosome profiling data. [F] Boxplot of decay rate (Y-axis) in genes that have pairwise interactions confined to the 5' end (Left plot), versus all over the transcript. Pairwise interactions at the 3' end tend to block decay. See also FIG. 12, Table 3;

FIG. 4. SPLASH identifies known and new human snoRNAs-rRNA interactions. [A], The black line graph indicates the region that U42B (Top) or U80 (bottom) interacts with 18S or 28S rRNA, respectively, in SPLASH. Light grey bars are the known interaction region for U42B and U80 respectively in the literature. Y-axis indicates the number of chimeric reads that mapped to rRNA. [B] Validation of novel human snoRNA-rRNA interactions. Left: SPLASH data indicates that SNORA32 (Top) interacts with the 5S rRNA, and SNORD83a (Bottom) interacts with the 18S rRNA. Y-axis indicates the number of chimeric reads supporting the interaction. Right: Independent pulldowns of 5S, 18S and 28S rRNA and qPCR analysis of SNORA32 (Top) and SNORD83a (Bottom) in each pulldown confirms the SPLASH data. Y-axis indicates the relative enrichment. [C] SPLASH reads for human U13-rRNA interactions are plotted along the 5' external transcribed spacer, 18S rRNA, and 28S rRNA. The light grey bar in the U13 plot indicates the known position of U13 binding. The grey line indicates the predicted sites for U13-rRNA interaction using the program PLEXY. U13 target sites that are supported by both SPLASH and PLEXY are starred. The Y-axis for PLEXY is in kcal/mol. [D] Model of RNA base pairing between U13 and 28S rRNA. The starred site is a newly identified U13-28S interaction that is supported by a PLEXY prediction. See also FIG. 13, Table 4;

FIG. 5. SPLASH identifies known and new yeast snoRNAs-rRNA interactions. [A] Line graph showing the locations of snR61 target sites on the 25S rRNA that are detected by SPLASH. The position of the known snR61 binding site is marked as a grey bar. The star indicates that the target site that is both identified by SPLASH and predicted by PLEXY. [B] A model showing predicted interactions between snR61 and 25S rRNA. 25S rRNA is shown in blue while snR61 is shown in black. [C] Line graphs showing SPLASH read counts for snR4 binding to 18S rRNA (Top) and 25S rRNA (Bottom). The starred sites indicate sites that are identified in SPLASH data, as well as previously in CLASH data. SPLASH identifies a new snR4 target site in the 18S rRNA, in addition to validating previously suggested sites [D] snR61, snR4 and snR30 sites are mapped onto the contour map of the yeast 25S rRNA. [E] Line graphs showing SPLASH reads for snR30-18S rRNA interactions in wild-type and Prp43 yeast mutant. [F] Heatmap of snoRNA target sites that are stabilized (left) or lost (right) in the Prp43 mutant as compared to wildtype yeast. The stabilized sites suggest that these snoRNAs might be dependent on Prp43 for release from rRNA. Newly identified target sites that require Prp43 for release are highlighted in red. Stars indicate sites where the snoRNAs have been previously found to bind to Prp43. See also FIG. 13, Table 5;

FIG. 6. Function and regulation of mRNA interaction modules. [A, B] Barcharts showing enrichment of Thymosin Beta 4, X-Linked (TMSB4X) [A] and Actin (ACTB) [B] interacting genes by qPCR analysis. The following names stands for Eukaryotic Translation Elongation Factor 1 Alpha 1 (EEF1A1), Ribosomal Protein S27 (RPS27), Beta-2-Microglobulin (B2M), Eukaryotic Translation Initiation Factor 5A (EIF5A) and Ribosomal Protein L35 (RPL35). Y-axis indicates login enrichment with respect to oligo pulldown against GFP. Error bars depict standard-deviation based on 3 biological replicates. [C] Two-dimensional heatmap showing enrichment of intermolecular interactions based on the location of chimera ends across mRNA pairs. We aligned transcripts according to their translation start and stop sites and plotted interactions from the last 200 bases of the 5' UTR, first and last 400 bases of the coding region, and first 400 bases of the 3' UTR. Enrichment was calculated as –log 10 (p-value) based on random sampling across the transcript with 100 bp windows. Black dotted lines demarcate the boundaries between 5' UTR, CDS and 3' UTR. [D] Network analysis of lymphoblastoid cells identified a major mRNA-mRNA interaction connected component. [E] Hierarchical clustering based on the density of mRNA-mRNA interactions separates the major component into 9 modules. GO term analysis of each module showed that the modules are enriched for mRNAs with specific functions and subcellular localization patterns. [F] Bar chart of the number of interaction pairs in observed interactions that are both cytoplasmic localized, or with one in the cytoplasm and the other in the nucleus, versus shuffled interaction pairs. Observed interactions between 2 mRNAs are significantly enriched when both RNAs are in the same cellular compartment, and depleted when they are in different compartments. See also FIG. 14, Table 6;

FIG. 7. Remodeling of the RNA interactome during human ES cell differentiation. [A] Boxplot showing changes in translation efficiency in mouse ES and RA cells for conserved human mRNAs with high circularization score in human ES cells and low circularization score in RA cells (Left), and vise versa (Right). mRNAs with a decrease in circularization score typically show a corresponding decrease in translation efficiency. [B} Arc plots of intramolecular interactions in the gene HMGA1, showing a decrease in circularization score after 5 days of RA differentiation. [C] Analysis of HMGA1 and Oct4 mRNA levels by qPCR in human ES cells and ES cells differentiated by retinoic acid (RA) for 5 days. [D] Analysis of HMGA1, Oct4 and GAPDH protein levels by western blotting in human ES and RA differentiated cells. [E, F] Network analysis of mRNA-mRNA intermolecular interactions in ES [E] and RA [F] cells showed that mRNAs are more interconnected in ES cells than in RA cells. [G, H] Hierarchical clustering based on density of mRNA-mRNA interactions identified specific modules in the major connected component of the interaction network. Representative enriched GO terms are shown as labels for each module. ES interaction modules [G] were observed to be more interconnected than RA interaction modules [H]. See also FIG. 14, Tables 6 and 7.

Figure 8:
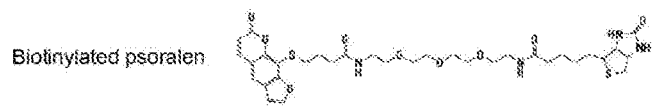
Figure 8:
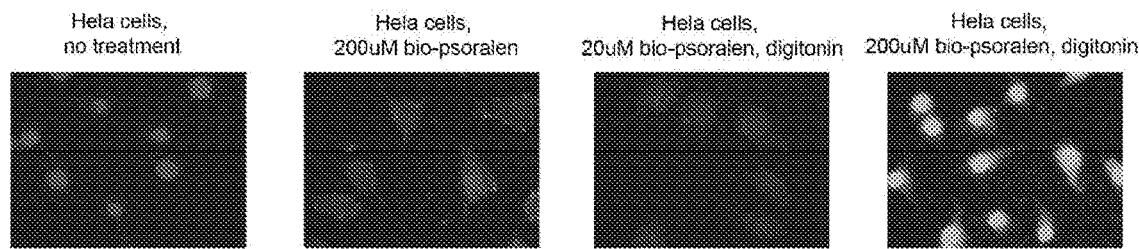
Figure 8:
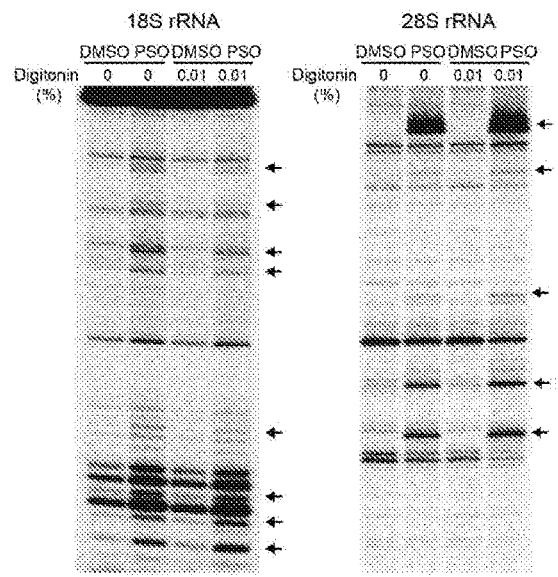
Figure 8:
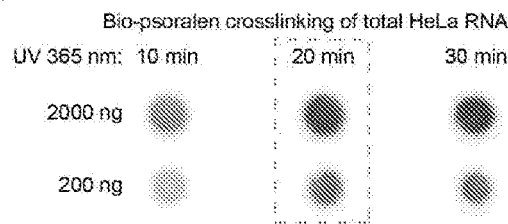
Figure 8:
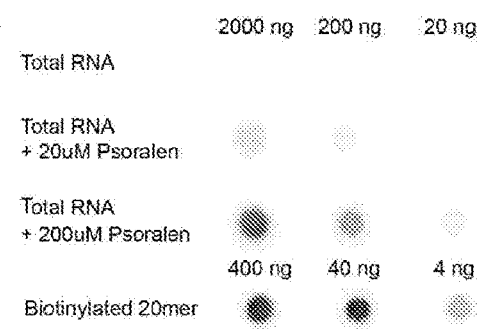
Figure 8:
Figure 8:
Figure 8:
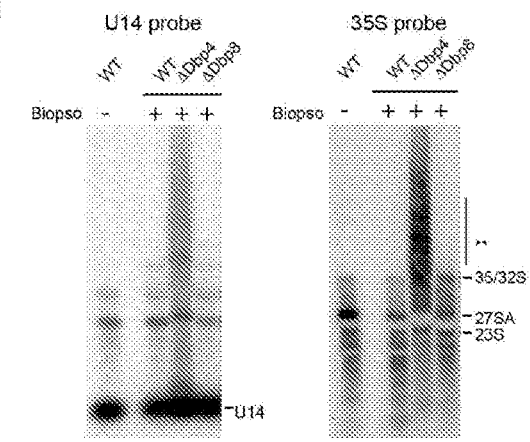

FIG. 8. Biotinylated psoralen can enter and crosslink RNAs in vivo, related to FIG. 1. [A] Structure of biotinylated psoralen. [B] Immunofluorescence images of HeLa cells treated with bio-psoralen and irradiated at 365 nm for UV crosslinking. Psoralen is present in both the nucleus and cytoplasm of the cells. 5 min treatment of 0.01% digitonin at 37° C. greatly increases the entry of biotinylated-psoralen into the cells. [C] Footprinting analysis on lymphoblastoid cells treated with (lanes 2, 4) and without 200 uM psoralen (Lanes 1, 3), in the absence (lanes 1, 2) and presence (lanes 3, 4) of 0.01% digitonin for 5 min. The black arrows indicate positions of reverse transcriptase stoppage due to psoralen crosslinking. Digitonin treatment does not change the pattern of psoralen crosslinking along 18S and 28S rRNA. [D] Titration of the amount of time for UV crosslinking of RNA interactions using psoralen. Dot blot using 2 μg (top) and 0.2 μg (bottom) of total RNA after crosslinking for 10, 20 and 30 min at UV 365 nm. The condition that we chose, 20 min, is boxed in grey dashed lines. [E] Dot blot showing the amount of biotinylated psoralen (bio-psoralen) incorporation into RNA as we increase the concentration of bio-psoralen added to the cells (Top). The biotinylated 20mer (Bottom) serves as a positive control for us to estimate the amount of psoralen incorporation into RNA. [F, G] Dotblot showing that psoralen can enter into *S. cerevisiae* and *E. coli* cells, although a higher concentration of psoralen is needed for a similar level of incorporation as in HeLa cells. [H] Northern blot analysis using probes complementary against U14 (left) and 35S precursor rRNA (right). U14 shows supershift in the presence of bio-psoralen, in Dbp4 mutant cells, confirming that bio-psoralen detects known interactions in the literature.

Figure 9:
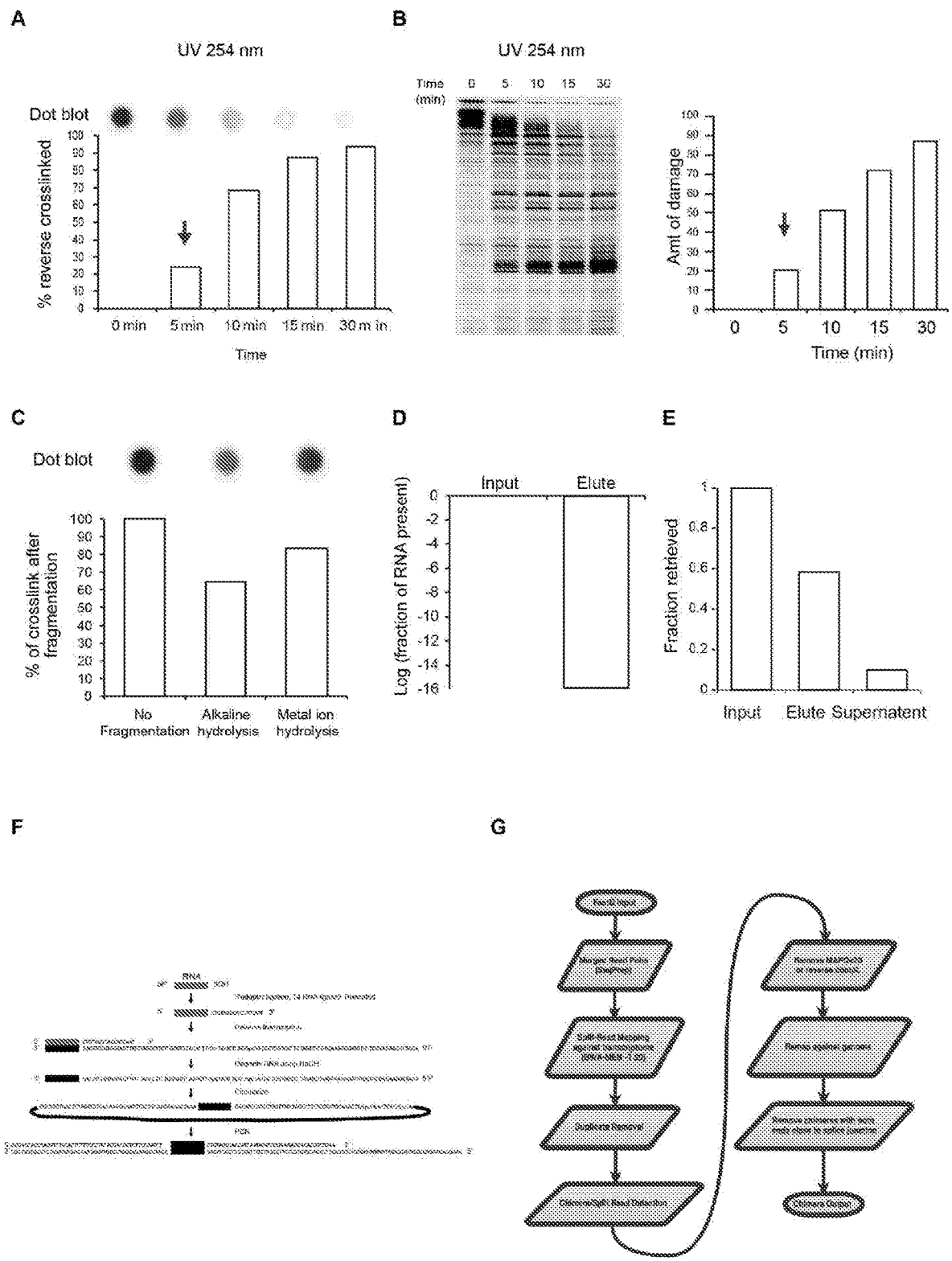

FIG. 9. SPLASH experimental pipeline, related to FIG. 1. [A] Quantification of the amount of reverse crosslinking upon irradiating the RNA with UV 254 nm over a time course. The dot blot indicates the amount of RNA that remains crosslinked upon irradiating with UV254 nm. The amount of reverse crosslinking on the Y-axis of the graph is 1-(fraction crosslinked). [B] RNA footprinting analysis of the yeast EFB1 mRNA that has been irradiated with UV 254 nM in vitro for 0, 5, 10, 15, 30 min. The bands indicate the stoppage sites by reverse transcription. RNA damage occurs as early as 5 mins after start of irradiation (Left). The percentage of damage is quantified as 100 (the percentage of full length transcripts detected by reverse transcription). The arrow indicates the condition that we used for library preparation (Right). [C] Metal ion hydrolysis retains the biotinylated psoralen on the RNA after fragmentation. Bar graph quantitating the amount of biotinylated psoralen (identified by dot blot) that remains on RNA before fragmentation, after fragmentation using alkaline hydrolysis at pH 9.2, after fragmentation using Mg2+ based metal ion hydrolysis. [D] qPCR quantification of the amount of non-specific binding on non-cross-linked EFB1 mRNA that remains bound to the beads after washing using the optimized wash protocol. We observed a $10^5$ fold decrease in non-specific binding in elute RNA compared to its original amount in input RNA after washing. [E] qPCR quantification of the amount of specific binding on bio-psoralen crosslinked TrxB2 mRNA that remains bound to the beads after washing using the optimized wash protocol. We retained about 60% of the mRNA in the elute, as compared to input, after binding and washing. [F] After ligating the two chimeras together, we devised an efficient of the chimeras, and then performed reverse transcription. We then circularized the cDNA and performed PCR amplification to obtain the final cDNA library. [G] Pipeline for analysis of SPLASH libraries, using sequenced 2×150 bp paired-end Illumina reads as input.

Figure 10:
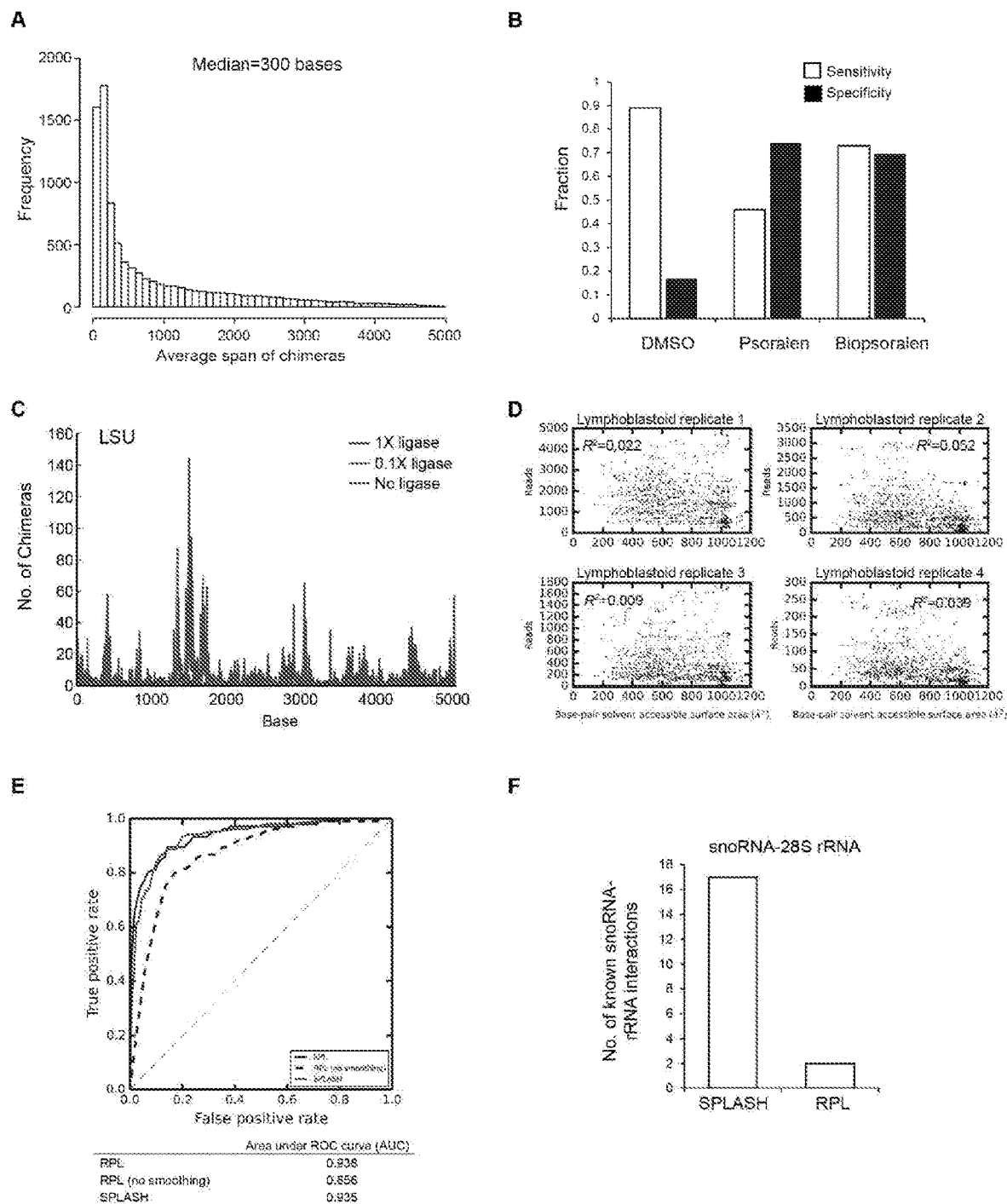

FIG. 10. SPLASH libraries are sensitive and accurate, related to FIG. 2. [A] Histogram showing the distribution of the span of chimeras that were found from SPLASH analysis in human lymphoblastoid cells. The median of the distribution is at 300 bases. [B] Barchart showing the sensitivity and specificity of a library without psoralen cross-linking, a psoralen crosslinked library and a biotinylated psoralen crosslinked library (SPLASH) benchmarked against known base pairs on the 28S rRNA. [C] No. of chimeric reads mapped to the 28S rRNA from libraries made with 1× ligase, 0.1× ligase and no ligase SPLASH libraries. Few chimeric reads are identified in the no ligase sample compared to the ligase samples. [D] Correlation analysis between the number of sequencing reads for four lymphoblastoid SPLASH libraries versus solvent accessibility at each base pair, evaluated using the FreeSASA program. Psoralen-biotin crosslinking to 28S rRNA does not show any dependence on solvent accessible surface area. [E] Receiver operating characteristic (ROC) curves for SPLASH data on 28S rRNA (using known base-pairing information as true positives) compared to RNA proximity ligation (RPL) with and without smoothing. [F] Number of known snoRNA-rRNA interactions detected in RPL and SPLASH libraries sequenced to similar depths, based on the human snoRNA database.

Figure 11:
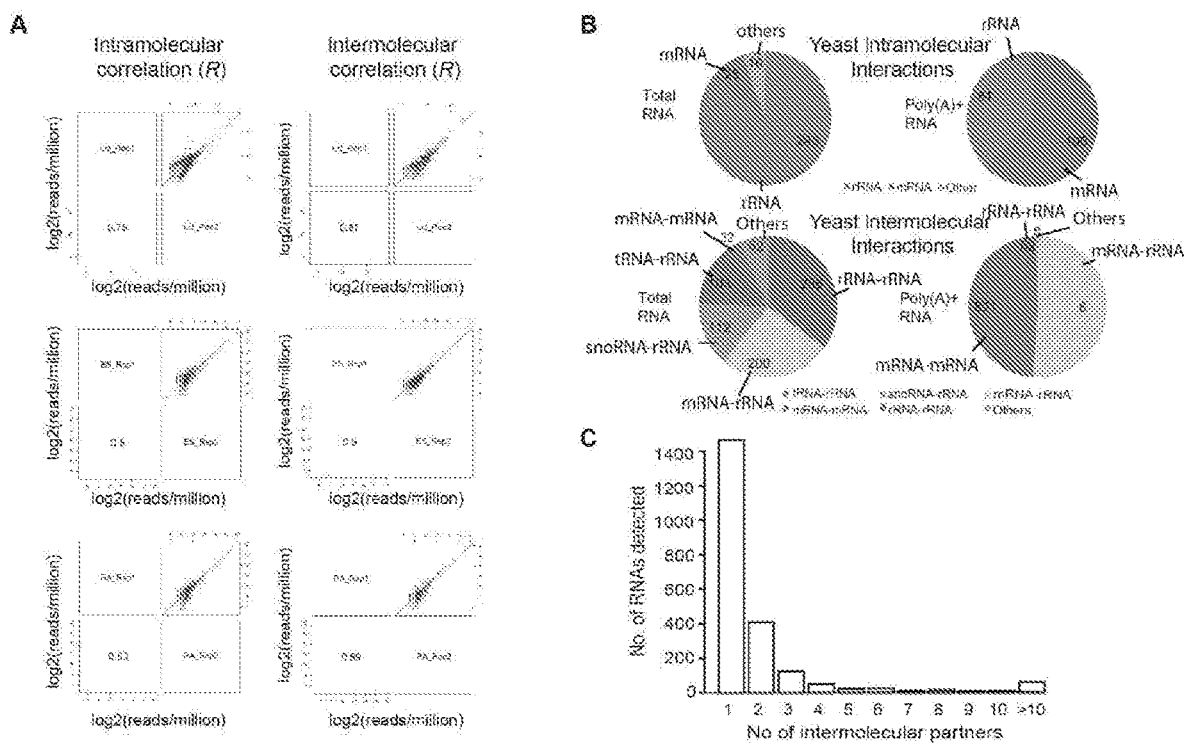

FIG. 11. Genomic analysis of SPLASH libraries, related to FIG. 2. [A] Correlation analysis between coverage of intramolecular (Left) and intermolecular (Right) chimeric interactions in 2 biological replicates of human ES, RA and lymphoblastoid cells. Intramolecular interaction correlations were calculated per interaction window while intermolecular interaction correlations were calculated for each gene pair. Read coverage was normalized by the total number of chimeric reads identified in each library. [B] Pie-charts showing the distribution of intramolecular (top) and intermolecular (bottom) interactions that belong to different classes of transcripts in two biological replicates of total RNA (Left) and polyA(+) enriched RNA (Right) in yeast. [C] Histogram showing the distribution of the number of RNA partners that an RNA was found to interact with (in lymphoblastoid cells). The median number of interactions was 1 per mRNA.

Figure 12:
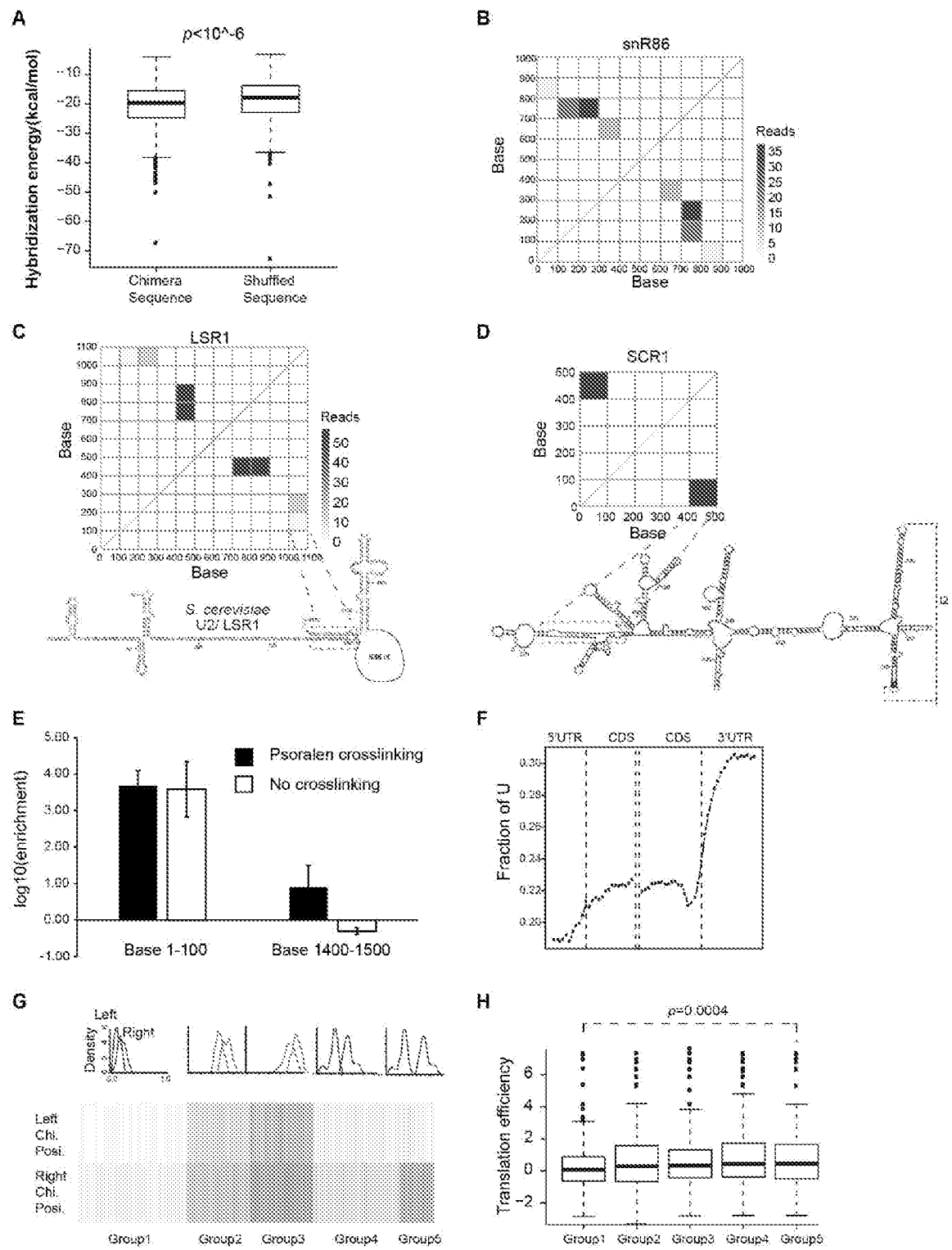

FIG. 12. Analysis and validation of SPLASH intramolecular interactions, related to FIG. 3. [A] Box plot of the interaction energy of intramolecular SPLASH chimeras in mRNAs (Left) versus randomly shuffled chimeras (Right). Y-axis shows the RNA hybridization energy (kcal/mol). True chimeras show a lower hybridization energy (calculated by RNAduplex) indicating that they form more stable base pairs. [B]Intramolecular interactions detected in yeast snR86 gene by SPLASH. The interactions suggest the formation of a long hairpin, consistent with the predicted secondary structure of snR86. [C] Top, Intramolecular interactions detected in yeast LSR1 gene by SPLASH. Both the 100-200:1000-1100 and the 400-500:800-900 interactions were consistent with previous crosslinking experiments. Bottom, secondary structure of LSR1 and where the 100-200:1000-1100 interaction is potentially occurring. [D] Top, Intramolecular interactions detected in yeast SCR1 gene by SPLASH. The 0100:400-500 interaction is consistent with previous reports and with the secondary structure of SCR1. [E] Validation of a long range intramolecular interaction between bases 1-100 and 1400-1500 of the yeast mRNA YBR118W. Psoralen and non-psoralen crosslinked yeast total RNA was fragmented and size selected to be between 100-300 bases, before pulldown of bases 1-100 using biotinylated antisense DNA probes. Y-axis indicates log(enrichment) of the fragment 1400-1500 that is pulled down together with bases 1-100 in the presence or absence of psoralen, by qPCR analysis. [F] Average fraction of U among all four nucleotides in human mRNAs, plotted for the last 200 bases of 5' UTR, first and last 400 bases of coding region and first 400 bases of 3' UTR. [G] K-means clustering of the locations of intramolecular interactions (from lymphoblastoid cells), into 5 clusters, show the different patterns of interactions that can occur within an RNA. Top, schematic of the positions of the chimeras along an mRNA. Bottom, heatmap showing the locations of the left (top) and right (bottom) ends of the interaction. The darker the shade [H] Boxplot showing the translation efficiency of the mRNAs in each cluster. mRNAs with more end-to-end interactions (Groups 4, 5) are translated more efficiently, while efficiently. The p-value was calculated using the Wilcoxon rank sum test.

Figure 13:
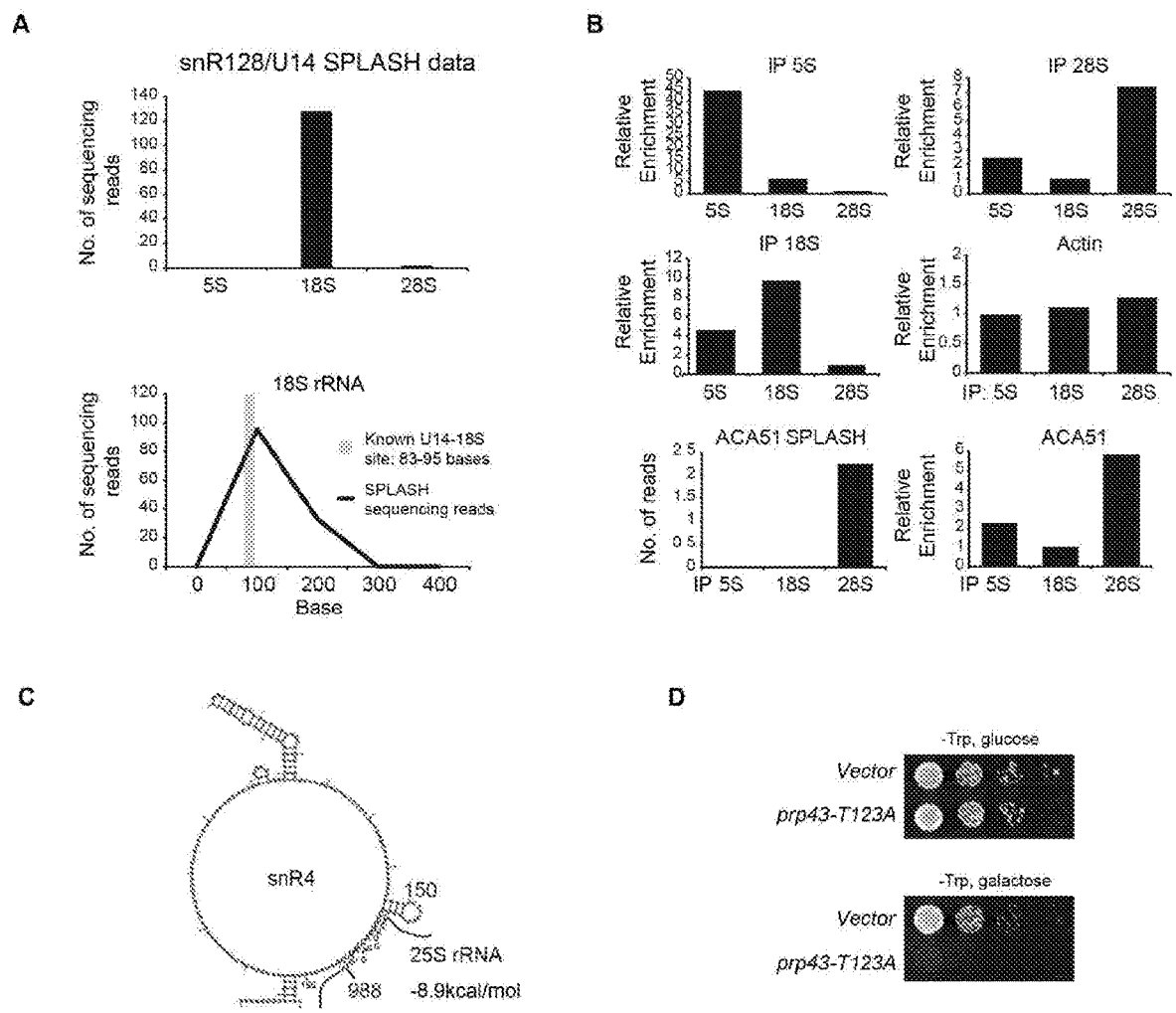

FIG. 13. SPLASH identifies snoRNA-rRNA interactions, related to FIG. 4,5. [A] SPLASH identifies the known U14-18S rRNA interaction (top), at the correct region along the 18S rRNA (bottom). Top: U14-rRNA chimeric reads mapped to 5S, 18S and 28S rRNA. Bottom: The black line indicates the number of U14-rRNA chimeric reads mapped along the 18S rRNA, while the light grey bar indicates the known position of U14-18S rRNA interaction. [B] Top and middle: Controls for snoRNA-rRNA pulldowns. Biotinylated antisense oligos against 5S, 18S and 28S rRNAs were used to pull down rRNAs. Y-axis indicates the log (enrichment) of the respective rRNAs normalized to pulldown by antisense probes to GFP. Actin is not selectively enriched in any of the three rRNAs. Bottom, validation of novel SNORA51/ACA51-28S rRNA interaction. Left: ACA51 interacts with 28S rRNA in SPLASH data. Right: ACA51-28S rRNA interaction is experimentally validated by pulldown of 5S, 18S and 28S rRNA. ACA51 binds to 28S with the highest affinity. [C] Model of snR4 interaction with 25S rRNA for an interaction site that is identified by SPLASH and predicted by PLEXY. [D] Prp43 mutant T-123A and WT yeast grown in the presence of galactose and glucose. Prp43 mutant yeast is defective when grown in galactose showing the successful deletion of Prp43.

Figure 14:
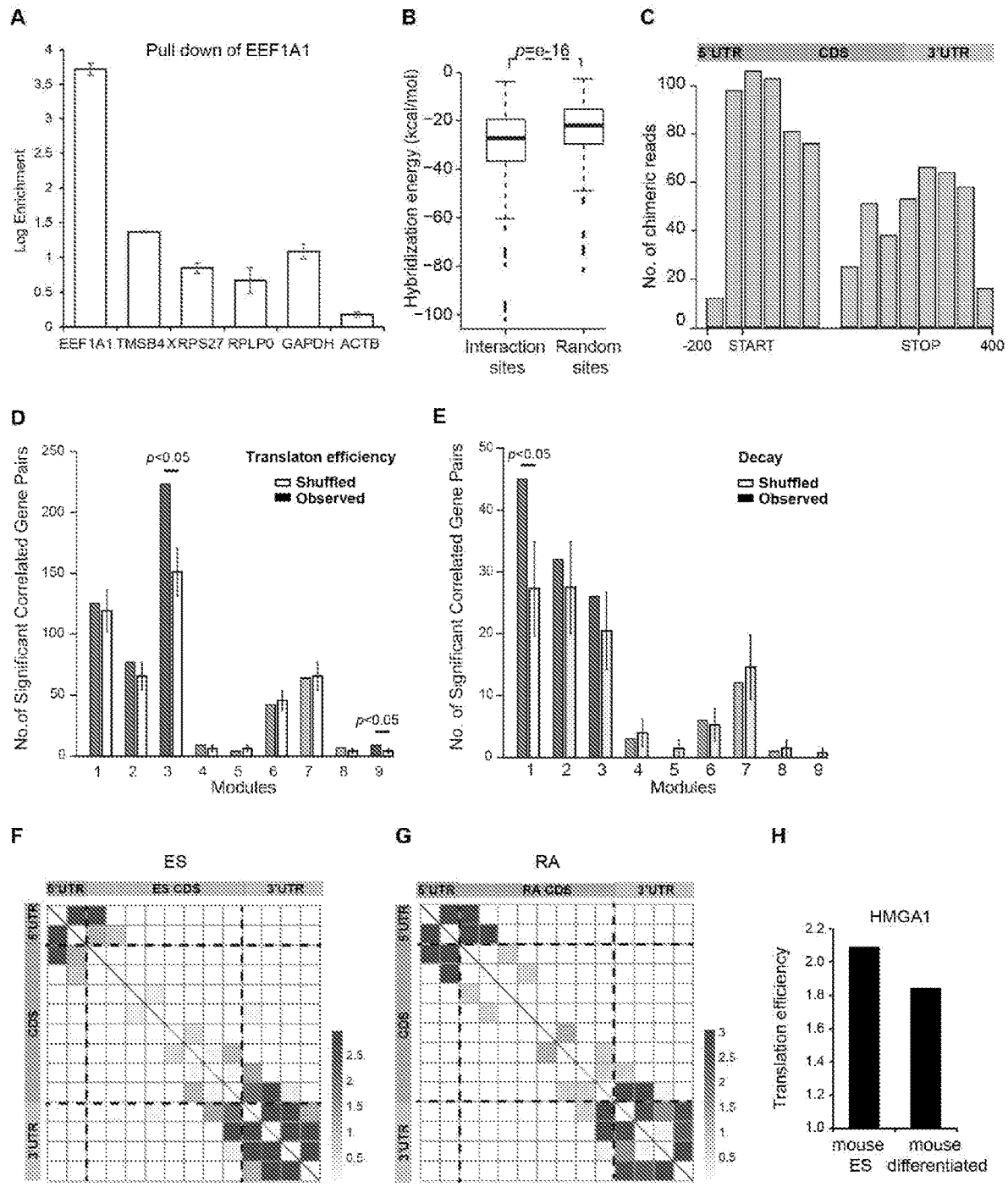

FIG. 14. Properties of intermolecular interactions detected by SPLASH, related to FIG. 6,7. [A] Barcharts showing log enrichment of EEF1A1 interacting genes by oligo pulldown of EEF1A1 and qPCR of its interacting genes in human ES cells. Oligo pulldown against GFP was used as negative control. Error bars depict standard-deviation based on 2 biological replicates. The following names stands for Eukaryotic Translation Elongation Factor 1 Alpha 1 (EEF1A1), Ribosomal Protein S27 (RPS27), Thymosin Beta 4, X-Linked (TMSB4X), Ribosomal Protein, Large, P0 (RPLP0), Glyceraldehyde 3-phosphate dehydrogenase (GAPDH), and Actin (ACTB). [B] Boxplot of the interaction energies of intermolecular SPLASH chimeras in mRNAs (Left) versus randomly shuffled chimeras in mRNAs (Right). Y-axis indicates the RNA hybridization energy (kcal/mol). True chimeras show a lower hybridization energy (computed by RNAduplex) indicating that they form more stable base pairs. [C] Metagene analysis of the frequency of intermolecular interactions along lymphoblastoid mRNAs, by aligning mRNAs along their translation start and stop. We plotted interactions that are present in the last 200 bases of 5' UTR, first and last 400 bases of coding region and first 400 bases of 3' UTR. [D, E] Barcharts showing the number of observed mRNA-mRNA pairs that are correlated in translation efficiency [D] or decay [E] versus random shuffling in each module. [F, G] Two-dimensional heatmap showing enrichment of interactions between one end of a chimera with the other end for all ES [F] and RA [G] mRNAs. We aligned transcripts according to their translation start and stop sites and plotted interactions from the last 200 bases of the 5' UTR, first and last 400 bases of the coding region, and first 400 bases of the 3' UTR. Enrichment was calculated as based on random sampling across the transcript with 100 bp windows. Black dotted lines demarcate the boundaries between 5' UTR, CDS and 3' UTR. Globally, the 2D heatmaps resemble the heatmap for lymphoblastoid cells. [H] Bar charts showing translation efficiency of HMGA1, as measured by ribosome profiling in mouse ES and differentiated cells. HMGA1 translation efficiency decreases during differentiation.

Table 1. Evaluation of different protocols for SPLASH, related to FIG. 1;

Table 2. Information of sequenced SPLASH libraries, related to FIG. 1;

Table 3. List of common human-human and human yeast interactions, related to FIG. 2;

Table 4. List of lymphoblastoid cells snoRNA target sites, related to FIG. 4;

Table 5. List of yeast snoRNA target sites, related to FIG. 5;

Table 6. GO analysis of network interactions in lymphblastoid, ES and RA cells, related to FIG. 6,7;

Table 7. Probes and qPCR primers used in validation, related to FIG. 6.

Methods & Materials

Cell culture. HeLa cells were grown in Dulbecco's Modified Eagle Medium (DMEM) supplemented with 10% Fetal bovine serum (FBS) and 1% Penicillin Streptomycin (PS). Human lymphoblastoid cells, GM12892, were grown in Roswell Park Memorial Institute (RPM') supplemented with 20% FBS, 1% PS and 2 mM L-Glutamine. hESC line H1 (WA-01, passage 30) was cultured in mTeSR1 (Stem cell technologies) media, on matrigel (BD) coated dishes. For Retinoic Acid (RA) treatment, the cells were seeded at 1:6 ratio and treated with 10 uM of RA after 16-24 hrs, and harvested after 5 days of treatment.

Crosslinking and extraction of human, yeast and *E. coli* RNAs. HeLa and GM12892 cells were washed with PBS and treated with 200 μM of EZ-Link™ Psoralen-PEG3-Biotin (Thermo Fisher Scientific) and 0.01% w/v Digitonin (Sigma) at 37° C. for 5 min. *Saccharomyces cerevisiae* (S288C, or W303a) or *Escherichia coli* (*E. coli* K12) were grown to exponential phase (OD=0.6), pelleted and washed in TE buffer and incubated with 2 mM of EZ-Link Psoralen-PEG3-Biotin at 37° C. for 10 min in TE. The cells were then spread onto a 10 cm plate and irradiated using 365 nm UV for 20 min on ice. Human and *E. coli* RNAs were isolated by using TRIzol reagent (Invitrogen) while Yeast RNAs were isolated using hot acid phenol extraction.

Fragmentation and enrichment of crosslinked RNA. 20 μg of RNA were fragmented with RNA fragmentation buffer (9 mM MgCl2, 225 mM KCl and 150 mM Tris HCl (pH 8.3)) at 95° C. for 5 min and size fractionated on a 6% TBE 8M Urea gel. Bases corresponding to 90-110 nt were excised and eluted overnight at 4° C. 1.5 µg of fragmented RNA was incubated with 100 µL of Dynabeads® MyOne™ Streptavidin C1 beads (Life Technology), dissolved in 2 mL of fresh Hybridization Buffer (750 mM NaCl, 1% SDS, 50 mM Tris-Cl pH 7.0, 1 mM EDTA, 15% formamide) and 1 ml of supplemented lysis buffer (50 mM Tris-Cl pH 7.0, 10 mM EDTA, 1% SDS) supplemented with Superase—in (1:200), at 37° C. for 30 min. The beads were washed with 1 mL of wash buffer (2× NaCl and Sodium citrate (SSC), 0.5% SDS) at 37° C. for 5 min with gentle agitation for five times.

Proximity ligation and reverse crosslinking. Enriched crosslinked samples were washed in cold T4 PNK buffer and treated with 0.5 unit of T4 PNK enzyme (NEB) at 37° C. for 4 hours in a 80 µl reaction. We then added fresh 1 mM ATP and 0.5 unit of T4 PNK in a 100 µL reaction, and incubated the reaction for 1 hr at 37° C. The chimeras were ligated using 2.5 units/µL of T4 RNA ligase I overnight at 16° C., in a 160 µL reaction, and eluted from the beads by incubating at 95° C. or 10 min in 100 µL of PK buffer (100 mM NaCl, 10 mM TrisCl pH 7.0, 1 mM EDTA, 0.5% SDS). Eluted RNA was extracted using TRIzol reagent, and cleaned up using RNeasy Cleanup Kit (Qiagen). We reverse crosslinked the RNA by irradiating at UV 254 nm for 5 min on ice.

3' Adapter ligation. Reverse crosslinked samples were resuspended in 6 µM of 3' adaptors and heat denatured at 80° C. for 90 seconds before snap cooling on ice. The 3' adaptors were ligated using T4 RNA ligase 2 KQ at 25° C. for 2.5 hours and size fractionated using a 6% TBE 8M Urea gel. RNA corresponding to 110-130 bases were excised and eluted overnight at 4° C.

Reverse transcription (RT). Eluted samples were resuspended in 208 nM of RT primers, heat denatured at 80° C. for 2 min and crashed on ice for 1 min. Denatured samples were then incubated at 50° C. for 30 min using SuperScript III (Invitrogen) for RT. cDNAs was recovered by degrading RNAs in 100 mM of NaOH, at 98° C. for 20 min, and size fractionating on a 6% TBE 8M Urea gel. cDNA of bases 200-220 were excised and eluted overnight at room temperature.

Circularization of cDNA product and PCR. The eluted cDNA samples were recovered by ethanol precipitation, circularized using Circligase II (Epicentre) and purified using DNA Clean & Concentrator™5 (Zymo). We performed 9-12 cycles of PCR amplification using primers from Primers Set 1 (New England Biolabs) and Q5 DNA polymerase (New England Biolabs). PCR products were ran on a 3% GTG Nusieve Agarose (Lonza) and bases 200-300 were gel extracted and purified using DNA gel extraction kit (Qiagen). The libraries were quantified using Qubit DNA HS Assay (Invitrogen), and sequenced on the Nextseq 500 machine (Illumina).

Human and Yeast Transcriptomes. Human and Yeast sequences were downloaded from the UCSC Genome Browser. Additional sequences belonging to human snoRNAs, snRNAs (extracted from NCBI), tRNAs (extracted from the UCSC Table Browser) and rRNAs were added to the human transcriptome list. Yeast UTR sequences, and non-coding gene sequences including rRNAs, tRNAs, snRNAs, snoRNAs and ncRNAs (*Saccharomyces* Genome Database) were also added to our transcriptome list.

Processing and detection of chimeric reads. Reads were adapter removed and merged using SeqPrep (version 1.0-7; https://github.com/jstjohn/SeqPrep). Merged reads were mapped to the transcriptome (see above) with BWA MEM (Li and Durbin, 2010) (version 0.7.12). Only split alignments that are i) >50 bp apart in transcriptome sequence, ii) not reverse complements of each other, and iii) with mapping quality >=20 are kept for downstream analysis. We further filtered the mapped transcriptome reads by ensuring that i) it could be uniquely mapped back to the human genome (hg19) using the program STAR, ii) does not span annotated splicing junctions, iii) present in at least two out of the four replicates, iii) had a minimum coverage of 2 and iv) if the average coverage in all replicates was at least 2. The final coverage of an interaction site is the average of normalized coverage in all replicates.

Availability. For source code and additional materials see http://csb5.qithub.io/splash/.

SRA accession number. SRP073550

SRA Bioproject ID. PRJNA318958

Cell culture. Human HeLa cells were grown in Dulbecco's Modified Eagle Medium (DMEM) supplemented with 10% Fetal bovine serum (FBS) and 1% Penicillin Streptomycin (PS) and psoralen crosslinked at 80% confluency. Human lymphoblastoid cells, GM12892, were grown in Roswell Park Memorial Institute (RPMI) supplemented with 20% FBS, 1% PS and 2 mM L-Glutamine to a concentration of $6 \times 10^5$ cells/mL. 20 mL were used for psoralen crosslinking. The hESC line H1 (WA-01, passage 30) was cultured in mTeSR1 (Stem cell technologies) media, on matrigel (BD) coated dishes. The media was refreshed daily. The hESCs were routinely subcultured with 1 mg/ml Dispase (Stem cell technologies) every 5-7 days. For Retinoic Acid (RA) treatment, the cells were seeded at 1:6 ratio. After 16-24 hrs, the cells were treated with 10 uM of RA. The media was refreshed daily and cells were harvested after 5 days of treatment.

SnoRNA immunoprecipitation. SnoRNA enriched samples were obtained by performing immunoprecipitation in IPP150 buffer (6 mM HEPES (pH8.0), 150 mM NaCl, 5 mM MgCl2, 0.1% Nonidet P-40) with protein A-agarose (Thermo Fischer Scientific) bound anti-TMG (R1131) antibodies. To precipitate TMG cap snoRNAs, total RNA was incubated with protein A-Agarose bound anti-TMG antibodies agarose beads on a rotating wheel for 3 hours at 4° C. The bead bound RNA was digested with proteinase K solution (50 mM Tris-HCl (pH7.5), 5 mM EDTA and proteinase K (2 g/l) for 30 min at 42° C. The RNA was extracted with phenol-chloroform and concentrated using ethanol precipitation.

3' adapter primer sequence.

```
                                              (SEQ ID NO: 1)
          5'-CTGTAGGCACCATCAAT-3' (IDT)
```

Reverse transcription primer sequence. 3' adapter ligated samples were recovered by ethanol precipitation and resuspended in 208 nM of RT primers,

```
                                              (SEQ ID NO: 2)
5'AGATCGGAAGAGCGTCGTGTAGGGAAAGAGTGTAGATCTCGGTGGTCG

C/iSp18/CACTC A/iSp18/TTCAGACGTGTGCTCTTCCGATCTATTG

ATGGTGCCTACAG-3' (IDT).
```

Preparation of control libraries. DMSO and psoralen crosslinked libraries were prepared the same way as the normal libraries, except for the skipping of the enrichment steps by binding to streptavidin beads. As we estimated that around 20 ng of bio-psoralen crosslinked and fragmented RNA is typically bound to streptavidin beads, we used the same amount (20 ng of fragmented, size selected samples) in the subsequent ligation and library preparation steps, using the same conditions as in SPLASH library generation.

Northern blot analysis of U14-18S rRNA interaction. Bio-psoralen crosslinked total RNA was extracted from wild-type, Dbp4p, or Dbp8p metabolic depleted yeast cells, and denatured at 95° C. for 5 minutes before separated by the gel electrophoresis (native, 1.2% agarose gel). RNA species that are crosslink by bio-psoralen will co-migrate in the gel. The double stars indicated a supershifted U14-35S rRNA complex, which is accumulated in the Dbp4 mutant. The non-bio-psoralen crosslinked wild-type RNA sample is used as a background control.

Dot blot analysis to detect the presence of biotinylated psoralen on RNA. Presence of biotinylated psoralen in the cross-linked RNA samples was detected with Chemiluminescent Nucleic Acid Detection Module (Thermo Fisher Scientific) following manufacturer's instructions. 1 ug of RNA was dotted on to a Biodyne™ B Nylon Membrane (Thermo Fisher Scientific) and cross-linked to the membrane by baking at 80 C for 15 minutes. The membrane was visualized using ChemiDoc™ MP System (BioRad) and quantified using the software Image J.

Calculation of bio-psoralen incorporation into cellular RNAs. Each positive control 20mer oligo contains one biotin molecule. From the number of moles of 20mer oligo and our crosslinked RNAs that are spotted, and intensity of the 20mer oligo by dot blot, we can estimate the amount of incorporation of psoralen in our RNAs.

Western Blotting and qPCR analysis of HMGA1, OCT4 and GAPDH. Human H1 ES cells and ES cells that are differentiated using retinoic acid (RA) for 5 days were lysed using RIPA buffer (150 mM sodium chloride, 1.0% Triton X-100, 0.5% sodium deoxycholate, 0.1% SDS, 50 mM Tris, pH 8.0) supplemented with 1:200 of Protease Inhibitor Cocktail Set III (Merck). Cells were incubated at 4 C for 20 minutes with gentle agitation. The lysate was then clarified by passing through a 25G BD Precision Glide Needle (Becton, Dickinson and Company) for a total of 6 times and centrifuged at 12000 rpm for 30 minutes at 4 C to pellet the insoluble fraction. The supernatant was collected and protein levels were normalized for each sample with Bio-Rad Protein Assay Dye Reagent Concentrate (Bio-Rad). Normalized samples were then size fractionated on a 12% sodium dodecyl sulfate polyacrylamide gel electrophoresis (SDS-PAGE) gel and transferred onto a Nitrocellulose Membrane (Bio-Rad). Membranes were blocked in 5% Blotting-Grade Blocker in PBST (137 mM NaCl, 2.7 mM KCl, 4.3 mM Na2HPO4, 1.47 mM KH2PO4, 0.1% Tween 20) and incubated with primary antibodies overnight at 4 C. The membranes were washed and incubated with secondary antibodies conjugated with HRP for 1 hour at room temperature. After washing, the membranes were incubated with Clarity™ Western ECL Substrate (Bio-Rad) and visualized with ChemiDoc™ MP System. The bands were quantified using the software Image J. The following antibodies were used with the dilutions stated: Anti-HMGA1 (cell signaling, #7777) 1:50000, Anti-Oct4 antibody (Abcam, ab19857) 1:10000, Anti-GAPDH Antibody (Merck, MAB374) 1:50000, anti-mouse IgG-HRP antibody (Santa Cruz, sc-2031) 1:5000, and anti-rabbit IgG-HRP antibody (Santa Cruz, sc-2313) 1:5000.

Total RNA was extracted from human ES and RA differentiated cells using the Trizol reagent (Thermo Fisher Scientific) and qPCR analysis was performed using the Brilliant II SYBR Green qRT-PCR 1-Step Master Mix kit, according to manufacturer's instructions. qPCR analysis are normalized to actin control.

Immunofluorescence imaging. HeLa cells were cultured on cover slips and treated with bio-psoralen. In vivo treated HeLa cells were rinsed with PBS once and fixed with 4% paraformaldehyde (Sigma) in PBS at room temperature for 30 min. Fixed cells were washed twice with PBS and permeabilized by incubating with 0.1% triton X-100 (Sigma) room temperature for 30 min. Permeabilized cells were rinsed once with PBS and blocked in 8% FBS (Gibco) in PBS for 2 hours at room temperature. 1:1000 of CF488A Streptavidin (Biotium) in blocking buffer was incubated with the cells at room temperature for 2 hours. After the incubation, the cells were washed with 0.1% Tween 20 in PBS and stained with 1:5000 DAPI (Biotium) for 3 min at room temperature and washed with PBS thrice. The prepared cover slips were transferred onto a glass slide coated with Prolong Gold Antifade (Thermo Fisher) and dried overnight at room temperature away from light.

Validation of intermolecular interactions by pulldown and qPCR. 10 µg of DNase treated psoralen cross-linked total RNA was diluted in 300 µL of water. The samples were then incubated with 100 µM of biotinylated probes, specific to the gene of interest, in fresh Hybridization Buffer (750 mMNaCl, 1% SDS, 50 mM Tris-Cl pH 7.0, 1 mM EDTA, 15% formamide) supplemented with Superase—in (1:200), and incubated at 37 C overnight with shaking. After hybridization of the probes, 100 uL of Dynabeads® MyOne™ Streptavidin C1 beads was used to pull out the RNA complexes. The beads were washed 5 times with wash buffer (0.1× NaCl and Sodium citrate (SSC), 0.5% SDS) that has been pre-warmed to 37 C. RNA was eluted from the beads by incubating with 100 µg of proteinase K (Thermo Scientific) in 95 µL of PK Buffer (100 mM NaCl, 10 mM TrisCl pH 7.0, 1 mM EDTA, 0.5% SDS) at 50 C for 45 min with end to end shaking, and boiling at 95 C for 10 minutes. Eluted RNA was recovered by using TRIzol reagent, and cleaned up using RNeasy MinElute Cleanup Kit (Qiagen). The recovered RNA was eluted in 20 µL of nuclease free water, irradiated with 254 nm UV for 5 min for reverse crosslinking. The samples were subsequently used for qPCR. Anti-GFP oligoes were used as a negative control.

Validation of intramolecular interactions. 100 µg of DNase treated psoralen or DMSO cross-linked total RNA was fragmented with RNA fragmentation buffer (9 mM MgCl2, 225 mM KCl and 150 mM Tris HCl (pH 8.3) at 95° C. for 3 min. After fragmentation, the RNA was size fractionated using a 6% TBE 8M Urea gel and RNA fragments corresponding to 100-300 bases were excised and eluted overnight at 4° C. 5 µg of RNA were used for the hybridization in the same conditions as in the pull down of intermolecular interactions. All probe and qPCR primer sequences for the pull down and qPCR are compiled in Table 7.

Data Analysis

Overview of the Computational Pipeline. The SPLASH pipeline automates read processing, mapping, interaction detection and filtering by using the snakemake workflow management system (version 3.4.1 (Koster and Rahmann, 2012)). See Supplementary FIG. 3B for a flowchart.

Human Transcriptome. To construct a transcriptome we downloaded all transcripts for hg19 RefSeq genes from the UCSC Table Browser. We then grouped isoforms into genes based on their gene names, and took the longest coding isoform, or if absent, the longest non-coding isoform as the representative of each gene. To this we added manually curated versions of snoRNAs, snRNAs (extracted from NCBI) and tRNAs (extracted from the UCSC Table Browser) and also replaced the complete repeating rRNA unit (U13369) with the resp. single rRNA sequences (including 5S rRNA and spacers) matching the used PDB structure (see below). This set of sequences was then deduplicated Bbmap's dedup.sh (options absorbcontainment=t minoverlappercent=11 absorbc=f; http://sourceforcre.net/projects/bbmap/). Any non-coding entry that did not belong to either miRNAs, rRNAs, snoRNAs, snRNAs or tRNAs was marked as small non-coding RNA, if its sequence was shorter than 200 bp, or lncRNA otherwise.

Yeast Transcriptome. To construct the yeast transcriptome, we extracted the sequences of yeast coding genes from UCSC Table Browser (sacCer3, sgdGene), and added in UTR sequences to the transcripts based on Nagalakshmi et al (Nagalakshmi et al., 2008). We then supplemented the sequences of non-coding genes, including rRNAs, tRNAs, snRNAs, snoRNAs and ncRNAs downloaded from *Saccharomyces* Genome Database. Duplicated sequences were then removed to yield the yeast transcriptome used in this study.

Processing of Sequencing Reads. Reads were preprocessed with SeqPrep (version 1.0-7; https://qithub.com/istjohn/SeqPrep) to remove adapters and merge overlapping paired-end reads into single reads of high quality. To speed this time consuming step up we parallelized the processing by working on split FastQ files. Since the majority of our paired-end reads should overlap, we used only the successfully merged ones for further analysis. Merged reads were mapped to the transcriptome (see above) with BWA MEM (version 0.7.12; and arXiv:1303.3997v1). We tuned BWA's parameters such that regions of minimum length 20 were detectable (-T 20; as opposed to the default 30). Mapped reads were sorted and converted to BAM with samtools (version 1.1). Afterwards, we removed all but the first read aligning to identical start coordinates and with identical CIGAR strings, which aggressively filters potential PCR duplicates (Ramani et al., 2015).

Detection of long range RNA interactions. To detect RNA interactions we scanned the BAM file for primary alignments containing BWA MEM's split alignment (SA) tag. We then discarded split alignments less than 50 bp apart. This mainly serves two purposes: 1) these would likely always evaluate as true in our PDB-based evaluation (see below) because bases are very close in sequence and therefore in structure and 2) we want to focus on the detection of long range RNA interactions. In addition we discarded interacting pairs where either end is mapped as reverse complement (transcriptome mapping) or has a mapping quality below 20. The latter effectively removes ambiguously mapped reads as well as alignments with close second best hits (e.g. pseudogenes).

Removal of splicing related false positives interactions. To deal with false positive interactions caused by splicing events, we remapped split reads from the transcriptome mapping back to the human genome (hg19) using the program STAr, and removed any read that entirely spans an annotated junction, allowing less than 5 bp soft-clip for both ends. The parameters of running STAR are: —twopassMode Basic—alignSplicedMateMapLminOverLmate 0.1—outSJfilterOverhangMin 10 6 6 6—outSJfilterCountUniqueMin 6 1 1 1—outSJfilterCountTotalMin 6 1 1 1—outSJfilterDistToOtherSJmin 5 0 5 0—alignSJDBoverhangMin 3—alignMatesGapMax 1000000—alignIntronMax 1000000—alignSJstitchMismatchNmax 5 -1 5 5—outStd SAM—outSAMtype SAM—winAnchorMultimapNmax 9000—seedPerWindowNmax 1000—outSAMstrandField None—outSAMmultNmax 1—outMultimapperOrder Random—outSAMattributes All—outSAMprimaryFlag AllBestScore—outFilterMultimapScoreRange 0—outFilterMultimapNmax 9000—outFilterMismatchNmax 2—outFilterIntronMotifs None—outFilterMatchNminOverLread 0.1—outFilterScoreMinOverLread 0.1—alignEndsTypeLocal". —outSAMmultNmax 1—outMultimapperOrder Random—outSAMattributes All—outSAMprimaryFlag AllBestScore—outFilterMultimapScoreRange 0—outFilterMultimapNmax 9000—outFilterMismatchNmax 2—outFilterIntronMotifs None—outFilterMatchNminOverLread 0.1—outFilterScoreMinOverLread 0.1—

The junction information was downloaded from the ENCODE project database Release 19 (GRCh37.p13).

Evaluation of ribosomal RNA interactions. To evaluate predicted rRNA-rRNA interactions we used the human 80S ribosome (PDB 4V6X), a cryo-EM structure with 5 Angstrom resolution. Each interaction pair window was mapped to the base combination with minimum 3D distance in the PDB structure. For each base we computed its centroid 3D position and counted a base pair as true, if its respective centroid distance was smaller than 30 Angstrom.

Comparison of sensitivity versus specificity between DMSO, psoralen and bio-psoralen libraries. True base-pairs of 28S rRNA were determined from Petrov et al. (Petrov et al., 2014). Results for RPL was obtained from Ramani et al. (Ramani et al., 2015), and processed as described in their paper and accompanying scripts. The smoothing step was omitted in an alternative analysis to evaluate RPL with minimal post-processing. In both cases the data were then coarse-grained into 100-base windows for direct comparison with SPLASH. The receiver operating characteristic (ROC) curve was then obtained by varying the threshold above which RPL value was deemed to have identified a hit. Similarly, we varied the threshold for SPLASH, systematically increasing the cutoff for identifying hits while still retaining the requirement of having consensus with at least two replicates and total reads of at least 8.

Evaluating the solvent accessibility of bio-psoralen. We consolidated the frequency each base-pair nucleotide appeared in a sequencing read, and estimated the corresponding base-pairs solvent accessible surface area (SASA) as the sum of the SASA of all the nucleotides in the identified base-pair, its preceding and succeeding base-pairs (i.e. total SASA of three consecutive base-pairs). Nucleotide SASA was evaluated using FreeSASA.

Prediction of snoRNA-rRNA interactions. Potential interaction sites of C/D box snoRNAs and the rRNA where predicted with Plexy in conjunction with RNAplex (version 2.1.9). To include weaker interactions the default energy threshold was removed. Interaction interfaces and energies for each predicted interaction were recorded for visualization.

Hybridization energies of RNA interactions. Hybridization energies for 1000 randomly chosen non-rRNA chimeras from human lymphoblastoid cells were computed with RNAduplex (ViennaRNA version 2.1.9). For each observed interaction, we also created a random equivalent, by shuffling the observed sequence preserving dinucleotide content. P-values were computed with Kolmogorov-Smirnov tests.

Visualization. For drawing classical RNA 2D structures we used VARNA (version 3.93). Arc diagrams were plotted using R4RNA.

Classification of RNA classes by circularization score. Circularization score for each mRNA is calculated by taking the average of all pair-wise intramolecular interactions in the RNA, and dividing by RNA length. P-value for boxplots were calculated using Wilcoxon rank sum test.

Association between RNA interactions, translation efficiency and decay. Translation efficiency, obtained from ribosome profiling data (Guo et al., 2010), was calculated for mRNAs with top and bottom 20% of circularization scores. For the association of the location of intramolecular interactions with translation, translation efficiency was calculated for mRNAs with interactions only in the 5' UTRs, versus all other interactions. Translation efficiency for human ES cells and RA cells was estimated from conserved mRNAs using mouse ES and mouse differentiated ribosome profiling data. mRNA decay was calculated for mRNAs with intramolecular interactions present only at the first, and last one third of the transcript, versus all over the transcript.

Two-dimensional RNA interactome maps. To generate a global view of intra-, or intermolecular mRNA-mRNA interaction as a heatmap, we analyzed the last 200 bases of 5'UTR, first and last 400 bases of CDS and the first 400 bases of 3'UTR, centered around the around the start/codon for each detected transcript. As each bin represents 100 bases along the transcript, we have 14 bins across the 5i UTR, CDS and the 3' UTR region in total. We then calculated the observed interactions on the 14×14 matrix.

We used resampling tests to access the significance of observed interactions in each bin within the matrix. Specifically, for each interaction, we generated a resampled interaction by randomly picking a pair of positions, weighted by the coverage of non-chimeric reads at the respective positions, from the same transcript as the observed interaction. We then aggregated all of resampled interactions in a 14×14 (or 10×10) matrix. Resampling was repeated 10,000 times. The p-value of observed number of interactions in each bin was calculated from this empirical distribution. Enrichment values as presented as $\log_{10}$ (p-value).

Enrichment of intermolecular mRNA interactions in different cellular compartments. We downloaded the nuclear and cytoplasmic polyA+ RNA-seq data for the GM12892 lymphoblastoid cell line from the GEO database under accession number GSM758560 and GSM765386. The raw reads were mapped to Human Genome (hg19) by STAR (v2.5.0) and FeatureCounts (v1.4.6) was used to count the number of raw reads for each gene, using GTF file downloaded from Ensembl (vGRCh37.75). We took genes with more than 10 reads in two out of four samples, and used a variance stabilizing transformation algorithm to normalize read counts across different replicates and conditions using DEseq2. The nuclear vs. cytoplasmic enrichment ratio was calculated for each gene by comparing normalized read counts between nuclear and cytoplasmic samples. We defined a gene as either nuclear- or cytoplasmic-enriched if the log 2 nuclear vs. cytoplasmic enrichment ratio was greater than 2 or less than −2 respectively. We then used resampling to test the significance of enrichment of intermolecular interactions (IMIs) among RNAs present in the same cellular compartment. We first grouped interactions based on the cellular compartmentalization of each partner, such as "cytoplasmic RNA—cytoplasmic RNA" and "cytoplasmic RNA—nuclear RNA". We then sampled the same number of genes from all expressed genes, requiring the distribution of gene expression (estimated from non-chimeric reads, which were mapped without splitting and derived from SPLASH libraries) to be similar to the genes with IMIs. Resampling was repeated 10,000 times. The observed number of IMIs was compared to the number of IMIs from the resampled gene sets for each cellular compartment, and the relative rank of observed IMIs was converted into the enrichment p-value accordingly.

Intermolecular interaction network analysis and correlation with gene regulation. mRNA-mRNA interaction network was constructed by excluding all disconnected edges and extracting modules from the network using the fast-greedy algorithm. We calculated the significance of correlation with gene regulation between pairs of mRNA genes within each of these modules by extracting datasets for gene expression, translation efficiency and decay rates and calculating the pair-wise Pearson correlation for all gene pairs within each module. The significance of correlation was then accessed by permuting the modules 10000 times.

Gene Ontology (GO) enrichment analysis of interaction modules. We used the TopGO package to access the functional enrichment of genes in each individual module in yeast, lymphoblastoid, ES and RA cells, with respect to biological process, molecular function and subcellular components. Genes in each module were compared against all genes with intermolecular interactions detected. The significance level of enrichment was computed with the "elim" algorithm implemented in TopGO. All reported enrichment terms are based on a false discovery rate threshold of 0.05.

Results

The SPLASH Protocol Enriches Effectively for In Vivo RNA-RNA Hybrids

To develop SPLASH, we used a biotinylated version of the crosslinker psoralen (bio-psoralen, FIG. 8A) to identify intramolecular and intermolecular RNA-RNA base pairing. Psoralen enters the cells and intercalates into base paired nucleotides, preferentially crosslinking pyrimidines, especially at Ts and Us, at UV 365 nm. The crosslinked RNAs were then extracted, fragmented and enriched for the crosslinked regions using streptavidin beads before undergoing proximity ligation and conversion into a deep sequencing library (FIG. 1A). Importantly, the use of bio-psoralen allows the preservation of RNA interactions in living cells, akin to the use of formaldehyde as an in vivo crosslinker for detecting protein-DNA and DNA-DNA interactions in chromatin immunoprecipitation (ChIP) and chromatin conformation capture experiments (Hi-C). In particular, the reversibility of bio-psoralen crosslinking at UV 254 nm enables reverse transcription across the ligated chimeras during library preparation. The biotin group on bio-psoralen also allows the selective enrichment of crosslinked interaction sites during the library preparation process, increasing the signal of pairwise interactions over the background of non-interacting sites (FIG. 1A).

While psoralen has been used to crosslink nucleotides in vivo, we observed that the entry of bio-psoralen into human cells was low. To increase the cellular uptake of bio-psoralen, we incubated cells with different concentrations of bio-psoralen, and in the presence of 0.01% digitonin, a mild detergent. Treating human cells with digitonin for 5 min significantly increased the entry of bio-psoralen as determined by immunofluorescence staining (FIG. 8B). We confirmed that a brief treatment of digitonin does not change psoralen crosslinking patterns (FIG. 8C) and titrated the amount of time it takes to efficiently crosslink RNAs in vivo (FIG. 8D). As RNA structure probing typically aims for "single hit kinetics", with few modified molecules per transcript, we titrated the concentration of bio-psoralen used such that it crosslinks at a frequency of approximately one in every 150 bases in the human transcriptome (FIG. 8E; Experimental Procedures). Bio-psoralen can also enter and crosslink RNAs in yeast and *E. coli* in vivo, although a higher concentration is needed (FIG. 8F,G). We confirmed that bio-psoralen can crosslink and detect known RNA interactions in vivo by performing a northern blot assay to detect known RNA-RNA interactions, such as the U14-18S binding in yeast (FIG. 8H).

The reversibility of psoralen crosslinking is key to the success of our library preparation process, however complete reverse crosslinking typically takes about 30 min at UV 254 nm, dramatically damaging RNA in the process. We titrated the duration of UV 254 nm exposure to the crosslinked RNAs, and identified conditions that maximized the amount of reverse crosslinking while minimizing UV damage (FIG. 9A, B). As library preparation processes typically involve multiple steps with different biases, we tested two different library cloning protocols that utilized i) 3' adapter ligation followed by reverse transcription, cDNA circularization and PCR (circularization protocol, FIG. 9F), as well as ii) independent 5' and 3' adapter ligations followed by reverse transcription and PCR (RNA ligation protocol) (Table 1). We found that the circularization protocol resulted in less bottlenecking and more efficient capture of chimeric reads than the RNA ligation protocol, while maintaining similar accuracy in capturing real chimeras based on the human 80S ribosome crystal structure (Table 1). We also identified fragmentation conditions that enabled us to fragment cross-linked RNA to ~100 bases without losing the biotin group (FIG. 9C), and stringent ligation and wash conditions that enabled us to generate SPLASH libraries with low background noise (FIG. 9D,E; Experimental Procedures).

The SPLASH Computational Pipeline Identifies RNA Interactions with High Specificity We integrated SPLASH data with a robust computational pipeline that was developed to accurately identify RNA-RNA interactions in the transcriptome. The pipeline stringently removes PCR duplicates, merges paired-end reads and then split maps them along the human and yeast transcriptomes to identify chimeric reads that indicate an RNA-RNA interaction (Experimental Procedures; FIG. 9G). Chimeric reads were filtered for splicing artefacts and clustered to identify pairwise interactions (Experimental Procedures). Additionally, all pairwise interactions that are continuous or are spaced less than 50 bases apart were removed, to focus the analysis on the long-range intramolecular and intermolecular interactions that cannot currently be reliably predicted using computational Experimental Procedures (Experimental Procedures). Overall, our stringent filtering retained 4.6 million chimeric reads (0.4% of all sequenced reads) that identify RNA-RNA interactions across the different transcriptomes. The resulting interactions span a wide range of distances, from 50 to 5000 bases, with a median distance of 300 bases (FIG. 10A).

To evaluate sensitivity and precision, intramolecular interactions reported by SPLASH analysis were compared to the crystal structure of the human 80S ribosome. Assessing regions of close spatial proximity in the crystal structure showed that SPLASH predictions provide a good balance between precision (75%) and sensitivity (78%) (<30 Å; FIG. 1C; Experimental Procedures). Visualising these interactions on the known secondary structure of the large ribosomal subunit highlights the dense network of long-range RNA interactions that were captured by SPLASH data (FIG. 1B). To estimate false discovery rate in reported interactions, we mixed independently crosslinked human and yeast total RNAs in equal amounts to prepare SPLASH libraries. Based on the observed human-yeast pairwise interactions, we estimated a false discovery rate of <3.7%, confirming that SPLASH analysis provides good control over the fraction of false interactions reported overall (Experimental Procedures). To verify that the SPLASH interactions are mediated by psoralen/bio-psoralen crosslinking events, we performed libraries without crosslinking, with psoralen crosslinking and with bio-psoralen cross-linking (SPLASH). Libraries generated with bio-psoralen showed similar levels of high specificity and increased sensitivity as compared to psoralen libraries (FIG. 10B), as expected due to enrichment of crosslinking sites by streptavidin beads in SPLASH. In contrast, non-cross-linked libraries showed low overall specificity (17%), confirming that psoralen/bio-psoralen crosslinking is essential to keep interacting RNA partners in close proximity for correct ligations to occur preferentially (FIG. 10B).

To further confirm that SPLASH chimeras are enriched for ligation events between crosslinked fragments and not random background ligations, we generated libraries without ligase, with ligase and with $\frac{1}{10}^{th}$ of the amount of ligase used in SPLASH. Libraries without ligase show a low level of background ligation, indicating that most pairwise interactions are due to intended proximity ligation events enabled by bio-psoralen crosslinking (Table 1, FIG. 10C). Furthermore, correlation analysis between the frequency of crosslinking events and solvent accessibility of a region demonstrates that bio-psoralen crosslinking is largely independent of solvent accessibility (FIG. 10D). Finally, benchmarking SPLASH against a recently published proximity ligation based approach indicates that SPLASH has similar precision for detecting intramolecular interactions, while detecting significantly more intermolecular interactions (FIG. 10E,F).

Global Structure of the Yeast and Human RNA Interactomes

To study RNA interactomes and their dynamics in different organisms, SPLASH was performed on 2-4 biological replicates of human cells, including Hela cells, lymphoblastoid cells, human embryonic stem (ES) cells and retinoic acid (RA) differentiated cells, as well as in wild type and Prp43 helicase mutant S. cerevisiae (Table 1,2). In addition, we performed sequencing on total RNA, poly(A)+ enriched, and snoRNA enriched RNA populations in different cell lines to capture RNA-RNA interactions globally and comprehensively. Based on more than two billion Illumina sequencing reads all together, we identified >8,000 intermolecular and >4,000 intramolecular interactions across different cell types (Table 2). We observed a high correlation between biological replicates in the same cell line (R=0.75-0.9) confirming that SPLASH data is reproducible (FIG. 11A). Overall, 3,497 intramolecular mRNA interactions and 84 lncRNA interactions from 1,311 genes were captured in this study, providing a rich resource for studying human RNA structure and function (FIG. 2A). Intermolecular interactions were found to be notably diverse and common, including 990 mRNA-mRNA interactions identified in human cell lines alone (FIG. 2B). Similar diversity was captured in thousands of yeast intramolecular and intermolecular interactions, enabling the identification of conserved human-yeast interaction features (FIG. 11B, Table 3). The degree distributions of the intermolecular interaction networks were found to have a good fit to a power law distribution for degree less than 10, but were accompanied by a heavy tail with many nodes with large degrees (FIG. 11C).

Long-Range Intramolecular RNA Interactions Define Distinct Classes of Functional RNAs To determine if our identified intramolecular interactions are highly stable, we calculated the energy of interactions between true chimeric pairs versus randomly shuffled chimeras with dinucleotide content preserved. Indeed, internal pairwise interactions have lower base-pairing energy compared to the shuffled set ($p<10^{-6}$, KS test, FIG. 12A), indicating that the chimeras are likely to be real. Comparing SPLASH intramolecular interactions with RNAs of known secondary structures, including LSR1, SCR1 and snR86 RNAs in yeast, further confirmed that SPLASH interactions are consistent with known interactions previously found by either biochemical or crosslinking experiments (FIG. 12B-D). We also validated a long-range intramolecular interaction in a yeast mRNA, demonstrating the reproducibility of our method (FIG. 12E).

To determine if there are differences in the propensity of different classes of RNAs to form long-range pairwise interactions, we calculated a "circularization score", which is an average of interaction distances within a transcript normalized by its length (FIG. 2C). Classifying different groups of RNAs according to their circularization score revealed that rRNAs and lncRNAs tend to form more distant interactions than mRNAs (Wilcoxon rank sum test, p=0.0045 and p=0.028 respectively, FIG. 2D). Long-range interactions in rRNAs likely contribute to their complex and highly structured conformation. Similar interactions in a subset of lncRNAs may be indicative of structure-mediated functions, such as acting as a scaffold to recruit different protein factors for cellular function.

The structural organization of mRNAs inside cells can impact their regulation and function. Using long-range interactions inferred from SPLASH for the human transcriptome, we constructed two-dimensional heatmaps of enriched interaction sites along a transcript (FIG. 3A). The heatmaps bring to light the highly modular nature of an average mRNA in the human cell, with bases in 5' untranslated regions (UTRs), CDS, and 3' UTRs preferentially interacting with other bases in the same domain, and extensions beyond the domain boundaries occurring right at the start and end of the coding region. Sequence composition was found to not correlate with the observed patterns, with bases near the beginning of mRNAs having very low pyrimidine content, but high levels of psoralen crosslinking (psoralen preferentially crosslink pyrimidines; FIG. 12F). Metagene analysis on intramolecular interaction sites aligned along translation start and stop codons also confirmed enrichment for interactions near the start of the mRNA (FIG. 3B).

To characterize the impact of interaction domains on mRNA function, mRNAs were grouped according to their propensity to form long-range pairwise interactions (circularization score) and assessed for translation efficiency. This analysis revealed that on average, mRNAs with shorter pairwise interactions are translated less efficiently than mRNAs with longer interactions (FIG. 3C). Furthermore, classifying transcripts according to the location of their pairwise interactions revealed that mRNAs with pairwise interactions only in the 5' UTRs tend to be translated slowly, consistent with a model whereby 5' end blocking of mRNAs can reduce translation efficiency (FIG. 3D). Sorting transcripts by translation efficiency to detect associated interaction patterns revealed two additional features. Firstly, efficiently translated mRNAs tend to have chimeras that span a longer distance, often connecting the beginning and ends of transcripts (FIG. 3E), in support of a circularization model for ribosome recycling and efficient mRNA translation (Wells et al., 1998). Secondly, poorly translated mRNAs tend to contain short chimeras that are clustered near the beginning of the transcript (FIG. 3E), highlighting that mRNAs with 5' end interactions are poorly translated. Similar conclusions were obtained when mRNAs were clustered in an unbiased manner based on the location of their interactions (FIG. 12G,H). Taken together, our data suggests a transcriptome-wide role for translation inhibition by stable structures near the start codon, as well as increased translation efficiency by end-to-end circularization.

Analysis of mRNA decay information revealed a similar influence of mRNA structure on RNA stability (FIG. 3F). Genes with interactions that are confined to the 5' end exhibited the fastest decay rates as compared to control, suggesting that interactions at the 3' end could block the exosome complex during RNA degradation, and emphasizing the importance of structure in post-transcriptional gene regulation.

SPLASH Uncovers New rRNA-rRNA and snoRNA-RNA Interaction Sites

Psoralen intercalates into base-paired regions independent of whether they are formed by the same RNA strand, or between two different RNA strands, enabling SPLASH to interrogate both intra- and intermolecular RNA interactions. As expected, SPLASH captures well-characterized intermolecular interactions corresponding to 5.8S-28S rRNAs, as well as between U4-U6, and U2-U6 snRNAs. In addition, SPLASH analysis identified many known snoRNA-rRNA interactions in the literature, validating the high sensitivity of our approach (FIG. 4A, FIG. 13A).

SnoRNAs are an important class of non-coding RNAs that guide the maturation of pre-ribosomal RNAs to form the functional ribosome. While the binding regions of some snoRNAs have been identified, the location of many snoRNA-rRNA interactions in the human ribosome remains elusive. Recently, snoRNA-rRNA interactions have been hypothesized to be more widespread than previously appreciated. However, snoRNA target prediction, especially for H/ACA snoRNAs which binds to rRNAs with short complementary stretches, still remains challenging, and experimental strategies such as CLASH have been applied mainly to detecting CAD box snoRNAs with rRNAs in yeast.

To identify snoRNA-rRNA interactions genome-wide in humans, SPLASH was performed on lymphoblastoid cells. Analysis of the trimethylated snoRNA immunoprecipitation libraries, as well as the deeply sequenced total RNA libraries identified 211 human snoRNA-rRNA interactions, corresponding to 78 human snoRNAs (55 C/D box and 23 H/ACA snoRNAs) (Table 4, Experimental Procedures). Based on the human snoRNA database, 122 out of the 211 identified snoRNA-rRNA sites are new, and include target sites for orphan snoRNAs such as SNORA51 (ACA51) and SNORD83. We validated three new snoRNA-rRNA interactions that were captured at different abundances by performing pulldown of 5S, 18S and 28S rRNAs individually and qPCR of the snoRNAs. While SNORA32 was previously thought to only bind to 28S rRNA based on the human snoRNA database, we identified and validated that SNORA32 binds strongly to the 5S rRNA (FIG. 4B). SNORD83a is an orphan snoRNA which we identified and validated to bind to the 18S rRNA (FIG. 4B). We also validated the weak binding of the orphan snoRNA ACA51 to the 28S rRNA (FIG. 13B), suggesting that SPLASH data is accurate even at low chimeric read counts. Predicted snoRNA-rRNA interaction sites from SPLASH were also integrated with a snoRNA prediction program (PLEXY) to refine binding site predictions (FIG. 4C,D). Using PLEXY, we narrowed down a new potential U13-28S rRNA binding site to bases 4418-4424 along the 28S rRNA (FIG. 4D). Thus, combining high throughput experimental data with snoRNA prediction algorithms can facilitate systematic, high-resolution identification of new snoRNA-rRNA interactions to improve our understanding of ribosome biogenesis.

Beyond human snoRNA-rRNA interactions, SPLASH analysis on two biological replicates of wild-type and Prp43 mutant yeast identified 106 target sites for 39 snoRNAs, including 27 C/D Box and 12 H/ACA snoRNAs (Table 5). For example, we identified the known target site of snR61, a C/D Box snoRNA, as well as two new binding sites on the 25S rRNA (FIG. 5A). The snR61 crosslinking site at bases 2800-2900 on the 25S rRNA is also predicted by PLEXY, further refining the location of this new site (FIG. 5B). We also identified target sites for the snR4 C/D box snoRNA, which was previously thought to be inactive. snR4-25S interactions were previously reported in CLASH data as low confidence hits that were not reproducibly found in all replicates. Here, we independently identified the same three snR4-25S rRNA interactions sites as in CLASH data, in addition to a new snR4-18S rRNA site, to support the existence of snR4-rRNA interactions (FIG. 5C,D, FIG. 13C). We also identified a target site for the orphan C/D Box snoRNA snR45 on 25S rRNA, in all 4 biological replicates, indicating that snR45 may play a role in 25S rRNA maturation.

As snoRNA-rRNA interactions are destabilized by helicases upon binding to pre-rRNA, SPLASH analysis in yeast cells that over-express the helicase Prp43 mutant (prp43-T123 Å, FIG. 13D) was used to identify additional transient snoRNA-rRNA interactions that are important for rRNA biogenesis. The essential H/ACA box snR30 was previously found to be released from 18S rRNA by the Rok1 helicase and is required for 35S cleavage and release of the 18S rRNA precursor. In our analysis, we identified snR30-18S rRNA interactions in the Prp43 mutant but not in the wildtype (FIG. 5E), suggesting that either multiple helicases can work on the same snoRNA substrate(s) to facilitate their release from rRNA or that Prp43 is required for Rok1 to unwind snR30 from the pre-ribosome. This is consistent with previous reports that both the Dbp4p and Has1p RNA helicases are required for U14 release from the pre-ribosome. Our top interaction sites identified highly confident snoRNA-rRNA basepairs that preferentially accumulated in Prp43 mutant versus wildtype cells (FIG. 5F). Many of these accumulated snoRNAs, including snR59, snR60, snR41 and snR55, were previously found to bind directly to Prp43, supporting the hypothesis that Prp43 is important for their release. SPLASH also provides evidence for new rRNA target sites for snR189, snR59, snR40, and snR69 in Prp43 mutant yeast, significantly expanding the list of interactions involved in snoRNA targeting and recycling.

mRNA-mRNA Interactions Define Modules of Co-Regulated Genes

Beyond snoRNA-rRNA interactions, SPLASH analysis identified nearly a thousand mRNA-mRNA interactions. We calculated the folding energies of these intermolecular mRNA interactions to determine whether they are likely to be stable. Intermolecular pairwise interactions exhibit not only lower folding energies than randomly shuffled chimeras with dinucleotide content preserved (median=−27.2 vs −21.85 kcal/mol, KS test, $p<10^{-15}$), but also lower folding energies compared to intramolecular mRNA interactions (median=−19.7 kcal/mol), indicating that they are likely to be even more stable (FIG. 14B). To estimate the true positive rate in intermolecular RNA interaction predictions, we experimentally tested them by using qPCR to determine enrichment of interaction partners after psoralen crosslinking and oligo pulldown (FIG. 6A, B; FIG. 14A). Overall, 12 out of 13 interaction pairs were validated, indicating high reproducibility and precision (92%) for intermolecular mRNA-mRNA predictions from SPLASH analysis.

To study the distribution of intermolecular interactions along an mRNA, we plotted the interaction density along the length of human mRNAs after aligning the transcripts according to their translation start and stop codons. Interestingly, most intermolecular interactions also occur near the beginning of the transcript (FIG. 14C). However, unlike intramolecular interactions whereby RNA interactions tend to occur within the same domain, intermolecular interactions frequently involve the binding of the beginning of one mRNA to another distal region along the second mRNA (FIG. 6C).

As a result, intermolecular 2D interaction plots displayed a much more spread-out interaction pattern across the transcript domains, and appear to be less modular.

Network analysis of the human RNA interactome identified a major mRNA interaction cluster that is strongly enriched for genes with RNA binding, metabolic, and translation properties (FIG. 6D, Table 6). Hierarchical clustering of the human RNA interactome based on the density of pairwise interactions identified nine modules, showing distinct enrichment for genes with defined functions and subcellular localizations across modules (FIG. 6E, Table 6). We observe that mRNAs tend to interact with other mRNAs in the same cellular compartment (p<0.05, FIG. 6F), confirming that physical proximity is necessary to drive intermolecular interactions with each other. We also observed that transcripts in mRNA modules can be coordinated in their gene regulation. This was observed for example in module 3 (a large group of translation related genes) which exhibited enrichment for correlated translation efficiency, as well as in module 1 (a group of RNA binding genes) which showed an enrichment for coordinated decay rates compared to controls (FIG. 14D,E). These observations highlight the role of intermolecular mRNA interactions as a potential mechanism for coordinating post-transcriptional gene regulation inside cells, with interaction modules serving to refine cellular compartments in enriching for RNA interactions.

Beyond the static picture of the RNA interactome in human cells, the extent to which RNA interactomes are dynamic and rewired during different cellular states is unclear. To investigate the RNA regulatory network governing cellular pluripotency, we performed SPLASH in human ES cells as well as in retinoic acid (RA) differentiated cells. Globally, the intramolecular patterns of RNA interactions for ES and RA cells are highly modular (FIG. 14F,G), similar to lymphoblastoid cells, suggesting that the modular pattern of mRNA intramolecular interactions are representative of most RNAs in different human cell types. Based on our previous observation that transcripts with high circularization scores tend to be translated better than those with low circularization scores, we hypothesized that mRNAs that undergo conformational changes can have corresponding changes in translation efficiency. To test this, we calculated the circularization scores for all well expressed genes in both ES and RA cells and identified mRNAs with high circularization scores in ES cells and low circularization scores in RA cells, and vice versa. Interestingly, mRNAs that shift from having a high circularization score in ES to a low circularization score in RA cells showed a corresponding decrease in translation efficiency and vice versa (FIG. 7A). This reaffirms the hypothesis that conformational changes can serve as an underlying mechanism to control translation efficiency during changes in cellular states. One of the chromatin genes, high mobility group 1, HMGA1, exhibited a notable decrease in circularization score and translation efficiency during RA differentiation, consistent with its key role in maintaining ES cell pluripotency (Shah et al., 2012) (FIG. 7B). Protein and mRNA quantification using western blot and qPCR analysis showed that HMGA1 protein levels decrease after 5 days of differentiation, whereas its mRNA levels do not (FIG. 7C, D). Furthermore, translation efficiency measured by ribosome profiling in mouse ES and differentiated cells showed a corresponding decrease in HMGA1 translation efficiency upon cellular differentiation (FIG. 14H), reinforcing the association between structural rearrangement and translation.

Analysis of the intermolecular interactome network in ES and RA cells revealed that mRNAs are more highly interconnected to each other in ES versus RA cells, despite a similar number of detected mRNAs (ES, 277 genes and 402 interactions, RA, 193 genes and 180 interactions; FIG. 7E,F). Module analysis of interacting RNAs in ES and RA cells further demonstrated the higher degree of interconnectedness in RNA interactions between ES cell modules when compared to RA cell modules (FIG. 7G,H; Table 6). To determine which modules in the ES cell interactome are disrupted during differentiation, we calculated the number of genes that were dissociated from each module upon RA differentiation. We observed that module 3, which is enriched for chromatin remodeling processes, is disrupted during cellular differentiation (p=0.0088), consistent with the importance of chromatin remodeling in maintaining pluripotency.

Discussion

The advent of high throughput sequencing has enabled us to obtain a significant amount of sequence information across diverse transcriptomes. However, information in transcriptomes is not limited to their linear sequence and can be encoded in intra- and intermolecular RNA interactions. Studying how RNA molecules pair with themselves and with others is thus key to understanding their function. The development and application of SPLASH to map pairwise RNA interactions has enabled the generation of transcriptome-wide maps in multiple human and yeast cell types, providing a global view of how transcripts are organized inter- and intramolecularly to impact gene regulation. Its application in different cell states also provides a view of the dynamic interactome and the functional impact of its remodeling during human ES cell differentiation.

Analysis of SPLASH data identified several key features in human interactomes, including the propensity of non-coding RNAs to form longer range interactions than mRNAs, and for mRNAs to adopt a modular configuration where the UTRs tend to interact with themselves and with nearby coding sequences. Interestingly, we do not see this modular pattern in intermolecular mRNA-mRNA interactions, with interactions being spread across the entire transcript. Follow-up experiments are needed to test various hypotheses for this observation, including the role of translation in maintaining mRNA modularity. Additionally, the role of (i) dense RNA interactions near the start codon for inhibiting translation, (ii) long-range end-to-end interactions for promoting efficient translation, and (iii) dense interactions near the 3' end for inhibiting mRNA decay, deserve further investigation. Collectively, our results provide evidence that structural organization of transcripts can play an essential role in gene regulation, and that changes in structural organization to regulate gene expression could be more widespread than previously anticipated.

Intermolecularly, we identified thousands of RNA-RNA interactions in human and yeast cells, including mRNA-rRNA, snoRNA-rRNA, mRNA-mRNA, and mRNA-lncRNA interactions. The majority of our interactions are mRNA-rRNA interactions, which we suspect to be a result of capturing mRNAs during translation. snoRNA-rRNA interactions are critical for ribosome maturation and misregulation of snoRNA abundances has been implicated in diseases such as cancer (Mannoor et al., 2012). Predicting snoRNA-rRNA targets, particularly for H/ACA snoRNAs, can be challenging. In this work, we detected existing and new target sites for 78 human snoRNAs (55 C/D box and 23 H/ACA snoRNAs), as well as for 39 yeast snoRNAs (27 C/D box and 12 H/ACA snoRNAs). The overlap between human and yeast datasets, as well as between experimental and in silico predictions can thus be used to systematically refine and prioritize snoRNA-rRNA interactions for further validation and characterization. In yeast, at least 19 helicases are involved in recycling of snoRNAs after target binding. Our identification of snoRNA-rRNA interactions stabilized in the absence of the Prp43 helicase, highlights an avenue for obtaining additional mechanistic insights for other helicases involved in snoRNA release and ribosome biogenesis.

Mapping of genome-wide RNA interaction networks showed that mRNAs are organized in modules based on connectivity in the interaction network, and mRNAs in the same module are enriched for specific functions and sub-cellular localizations. These results suggest that RNA interaction modules containing genes of similar functions can be an organizing structure to coordinate translation and decay, and act as a mechanism for gene regulation. Human ES and RA interaction networks also showed that large RNA conformational changes in vivo are associated with corresponding changes in translation efficiency, indicating that (i) conformational changes are more widespread than previously appreciated, and (ii) that they could serve as underlying mechanisms for translation changes during ES differentiation. We also observed that the RNA interactome becomes sparser upon differentiation, with fewer mRNAs interacting with each other in differentiated cells, and that a chromatin remodeling associated module was additional lost during differentiation. Further functional studies disrupting individual interactions in these modules could help understand the robustness of these modules and the key interactions that are involved in the differentiation process.

SUMMARY

In summary, SPLASH expands our understanding of the structural organization of eukaryotic transcriptomes, and helps to define the principles of how RNAs interact with themselves and with other RNAs in gene regulation and ribosome biogenesis. Apart from yeast and human cells, SPLASH is applicable to other organisms (such as *E. coli*) to interrogate RNA interactions under different cellular conditions. Coupled with genome-wide secondary structure mapping and RNA structure modeling, SPLASH data can help refine our current models of RNA structure with in vivo information.

SPLASH can also be combined with intermolecular RNA interaction prediction tools, such as snoRNA prediction programs, to improve the accuracy of these predictions. Techniques to enrich specific RNA fractions can be combined with SPLASH to further study rare RNAs. We anticipate that future studies using SPLASH will continue to shed light on the complexity and dynamics of RNA interactions in cellular systems across diverse organisms.

TABLE 1

Evaluation of different protocols for SPLASH, related to FIG. 1.

| Condition | No. of reads (merged pairs) | No. of rRNA Chimeric_Dup_Removed | PPV |
|---|---|---|---|
| RNA ligation method | | | |
| No ligase | 1700874 | 85 | 0.4824 |
| 0.1X ligase | 1610716 | 143 | 0.5524 |
| 1X ligase | 1787607 | 225 | 0.4889 |
| Circligase method | | | |
| No ligase | 2310350 | 117 | 0.6068 |
| 0.1X ligase | 1671569 | 559 | 0.5510 |
| 1X ligase | 2386429 | 1261 | 0.5234 |
| Wash conditions | | | |
| Circligase with Wash buffer I (2X SSC) | 2210723 | 1921 | 0.5122 |
| Circligase with Wash buffer II (0.1x SSC with 15% formamide) | 2711055 | 3588 | 0.4961 |

TABLE 2

Information of sequenced SPLASH libraries, related to FIG. 1.

| Sample | Merged reads | Mapped reads | Mapped reads after PCR dups removal | No. of chimeric reads after filtering | Passed Intra Chimeras | Passed Inter Chimeras |
|---|---|---|---|---|---|---|
| Lymphoblastoid Cells Total RNA Replicate 1 | 53,747,987 | 53,309,764 | 3,228,021 | 311,079 | 147,850 | 163,229 |
| Lymphoblastoid Cells Total RNA Replicate 2 | 29,859,136 | 29,865,379 | 3,081,880 | 239,724 | 105,429 | 134,295 |
| Lymphoblastoid Cells Total RNA Replicate 3 | 60,332,939 | 59,565,659 | 3,482,737 | 208,630 | 99,687 | 108,943 |
| Lymphoblastoid Cells Total RNA Replicate 4 | 45,400,893 | 45,667,145 | 3,923,185 | 279,368 | 123,773 | 155,595 |
| Lymphoblastoid snoRNA IP | 149,071,830 | 148,389,870 | 2,218,555 | 174,295 | 68,603 | 105,692 |
| Lymphoblastoid Cells PolyA Replicate 1 | 183,913,864 | 175,803,028 | 59,637,038 | 160,800 | 97919 | 62881 |
| Lymphoblastoid Cells PolyA Replicate 2 | 115,234,808 | 110,846,796 | 43,847,439 | 109,274 | 58016 | 51258 |
| Lymphoblastoid Cells PolyA Replicate 3 | 3,963,881 | 3,814,459 | 2,751,106 | 7,211 | 3819 | 3392 |
| Lymphoblastoid Cells PolyA Replicate 4 | 53,371,012 | 50,589,091 | 15,197,222 | 82,921 | 64919 | 18002 |
| Human ES PolyA Replicate 1 | 159,412,735 | 153,023,928 | 72,028,001 | 73,407 | 34674 | 38733 |
| Human ES PolyA Replicate 2 | 68,290,966 | 66,046,593 | 21,635,588 | 42,109 | 14209 | 27900 |
| Human RA PolyA Replicate 1 | 153,884,298 | 144,714,995 | 60,325,593 | 77,245 | 41090 | 36155 |
| Human RA PolyA Replicate 2 | 87,849,979 | 82,593,496 | 24,842,241 | 26,661 | 12966 | 13695 |
| Yeast Total RNA replicate 1 | 12,705,039 | 12,419,256 | 2,224,683 | 26,520 | 4,063 | 22,457 |
| Yeast Total RNA replicate 2 | 29,292,969 | 28,655,555 | 5,854,878 | 39,665 | 13,635 | 26,030 |
| Yeast Prp43 mutant Total RNA replicate 1 | 8,260,248 | 8,134,607 | 1,872,711 | 25,794 | 8,555 | 17,239 |
| Yeast Prp43 mutant Total RNA replicate 2 | 31,719,541 | 31,194,218 | 2,609,303 | 34,530 | 5,877 | 28,653 |
| Yeast PolyA replicate 1 | 16,412,271 | 16,261,107 | 9,768,660 | 167,092 | 3,910 | 163,182 |
| Yeast PolyA replicate 2 | 13,414,403 | 13,255,714 | 8,636,175 | 225,395 | 3,700 | 221,695 |
| Biotinylated psoralen libraries replicate 1 | 12,207,150 | 11,689,548 | 2,150,196 | 36,846 | 17,080 | 19,766 |
| Biotinylated psoralen libraries replicate 2 | 9,114,009 | 8,876,983 | 2,052,463 | 86,823 | 34,450 | 52,373 |
| Psoralen libraries replicate 1 | 32,453,663 | 32,500,917 | 1,898,212 | 112,574 | 53,980 | 58,594 |
| Psoralen libraries replicate 2 | 8,176,811 | 8,123,956 | 818,852 | 18,368 | 7,681 | 10,687 |
| DMSO libraries replicate 1 | 43,587,340 | 43,411,408 | 3,446,432 | 255,787 | 110,459 | 145,328 |
| DMSO libraries replicate 2 | 35,095,430 | 34,981,150 | 2,951,955 | 205,083 | 92,172 | 112,911 |

TABLE 3

List of common human-human and human yeast interactions

| Organism | Type | Human Gene 1 | Human Gene 2 | Yeast gene1 | Yeast gene 2 | Region 1 | Region 2 |
|---|---|---|---|---|---|---|---|
| Human-yeast | Intermolecular | PKM | EEF1A1 | YAL038W | YBR118W | | |
| Human-yeast | Intermolecular | RPL29 | GAPDH | YFR032C-A | YGR192C | | |
| Human-yeast | Intermolecular | RPS6 | GAPDH | YBR181C | YGR192C | | |
| Human-yeast | Intermolecular | YWHAE | GAPDH | YER177W | YGR192C | | |
| Human-yeast | Intermolecular | TPI1 | GAPDH | YDR050C | YGR192C | | |
| Human-yeast | Intermolecular | GAPDH | TPT1 | YGR192C | YKL056C | | |
| Human-yeast | Intermolecular | GAPDH | RPL10 | YGR192C | YLR075W | | |
| Human-yeast | Intermolecular | RPL10 | RPS3 | YLR075W | YNL178W | | |
| Human-yeast | Intermolecular | GAPDH | RPL3 | YGR192C | YOR063W | | |
| Human-yeast | Intermolecular | GAPDH | RPS12 | YGR192C | YOR369C | | |
| Human-human | Intermolecular | ACTB | RPL4 | | | | |
| Human-human | Intermolecular | ATP1A1 | TPT1 | | | | |
| Human-human | Intermolecular | BTN2A2 | LINC01604 | | | | |
| Human-human | Intermolecular | COX4I1 | RPL10 | | | | |
| Human-human | Intermolecular | EDARADD | ENO1 | | | | |
| Human-human | Intermolecular | EEF1A1 | EEF1G | | | | |
| Human-human | Intermolecular | EEF1A1 | GAPDH | | | | |

TABLE 3-continued

List of common human-human and human yeast interactions

| Organism | Type | Human Gene 1 | Human Gene 2 | Yeast gene1 | Yeast gene2 | Region 1 | Region 2 |
|---|---|---|---|---|---|---|---|
| Human-human | Intermolecular | EEF1A1 | hsnrna-RNU1-1 | | | | |
| Human-human | Intermolecular | EEF1A1 | MTRNR2L8 | | | | |
| Human-human | Intermolecular | EEF1A1 | RPL10A | | | | |
| Human-human | Intermolecular | EEF1A1 | RPL13 | | | | |
| Human-human | Intermolecular | EEF1A1 | RPL18A | | | | |
| Human-human | Intermolecular | EEF1A1 | RPL22 | | | | |
| Human-human | Intermolecular | EEF1A1 | RPL3 | | | | |
| Human-human | Intermolecular | EEF1A1 | RPL31 | | | | |
| Human-human | Intermolecular | EEF1A1 | RPL32 | | | | |
| Human-human | Intermolecular | EEF1A1 | RPL35 | | | | |
| Human-human | Intermolecular | EEF1A1 | RPL37 | | | | |
| Human-human | Intermolecular | EEF1A1 | RPL37A | | | | |
| Human-human | Intermolecular | EEF1A1 | RPL41 | | | | |
| Human-human | Intermolecular | EEF1A1 | RPL6 | | | | |
| Human-human | Intermolecular | EEF1A1 | RPL7 | | | | |
| Human-human | Intermolecular | EEF1A1 | RPL7A | | | | |
| Human-human | Intermolecular | EEF1A1 | RPL9 | | | | |
| Human-human | Intermolecular | EEF1A1 | RPLP0 | | | | |
| Human-human | Intermolecular | EEF1A1 | RPS15A | | | | |
| Human-human | Intermolecular | EEF1A1 | RPS2 | | | | |
| Human-human | Intermolecular | EEF1A1 | RPS23 | | | | |
| Human-human | Intermolecular | EEF1A1 | RPS27A | | | | |
| Human-human | Intermolecular | EEF1A1 | RPS3 | | | | |
| Human-human | Intermolecular | EEF1A1 | RPS3A | | | | |
| Human-human | Intermolecular | EEF1A1 | RPS6 | | | | |
| Human-human | Intermolecular | EEF1A1 | RPS7 | | | | |
| Human-human | Intermolecular | EEF1A1 | RPS8 | | | | |
| Human-human | Intermolecular | EEF1A1 | TPT1 | | | | |
| Human-human | Intermolecular | EEF1A1 | TUBA1B | | | | |
| Human-human | Intermolecular | EIF5A | PTMA | | | | |
| Human-human | Intermolecular | ENO1 | GAPDH | | | | |
| Human-human | Intermolecular | FLJ44635 | TPT1 | | | | |
| Human-human | Intermolecular | GAPDH | RPL13 | | | | |
| Human-human | Intermolecular | GAS5 | U81 | | | | |
| Human-human | Intermolecular | GLTSCR2 | PTMA | | | | |
| Human-human | Intermolecular | GNB2L1 | RPS12 | | | | |
| Human-human | Intermolecular | GPX1 | RPL10 | | | | |
| Human- | Intermolecula | LRRC75AAS1ZNF485 | | | | | |
| Human- | Intermolecula | LYRM7 | NOL10 | | | | |
| Human- | Intermolecula | NPM1 | RPL18A | | | | |
| Human- | Intermolecula | PAGR1 | TRUB2 | | | | |
| Human- | Intermolecula | PIK3C2B | U80 | | | | |
| Human- | Intermolecula | RAB13 | RAB8B | | | | |
| Human- | Intermolecula | RPL10 | RPL35 | | | | |
| Human- | Intermolecula | RPL13A | RPL18A | | | | |
| Human- | Intermolecula | RPL35 | RPLP2 | | | | |
| Human- | Intermolecula | RPL35 | RPS28 | | | | |
| Human- | Intermolecula | RPL36AHNRNH2 | RPL36AL | | | | |
| Human- | Intermolecula | RPL37A | RPLP1 | | | | |
| Human- | Intermolecula | RPL3 | RPS3 | | | | |
| Human- | Intermolecula | RPL41 | hsnrna-RNU1-1 | | | | |
| Human- | Intermolecula | RPL41 | RPS17 | | | | |
| Human- | Intermolecula | RPL41 | RPS3 | | | | |
| Human- | Intermolecula | RPL5 | TMSB4X | | | | |
| Human- | Intermolecula | RPLP1 | RPS3 | | | | |
| Human- | Intermolecula | RPS11 | RPS15A | | | | |
| Human- | Intermolecula | RPS20 | TMEM70 | | | | |
| Human- | Intermolecula | RPS3 | RPS6 | | | | |
| Human- | Intermolecula | TPM3 | TRUB2 | | | | |
| Human- | Intermolecula | TPM3 | ZNF485 | | | | |
| Human- | Intramolecula | ABI1 | ABI1 | | | 1000-1100 | 1100-1200 |
| Human- | Intramolecula | ACTB | ACTB | | | 1400-1500 | 1700-1800 |
| Human- | Intramolecula | ACTG1 | ACTG1 | | | 0-100 | 1900-2000 |
| Human- | Intramolecula | ACTG1 | ACTG1 | | | 0-100 | 200-300 |
| Human- | Intramolecula | ACTG1 | ACTG1 | | | 100-200 | 200-300 |
| Human- | Intramolecula | ACTG1 | ACTG1 | | | 1500-1600 | 1900-2000 |
| Human- | Intramolecula | ACTG1 | ACTG1 | | | 1600-1700 | 1700-1800 |
| Human- | Intramolecula | AKR1A1 | AKR1A1 | | | 0-100 | 200-300 |
| Human- | Intramolecula | AKR1A1 | AKR1A1 | | | 300-400 | 500-600 |
| Human- | Intramolecula | ANAPC11 | ANAPC11 | | | 200-300 | 600-700 |
| Human- | Intramolecula | AP2M1 | AP2M1 | | | 200-300 | 300-400 |
| Human- | Intramolecula | APEX1 | APEX1 | | | 100-200 | 1200-1300 |
| Human- | Intramolecula | ARL6IP1 | ARL6IP1 | | | 1500-1600 | 1700-1800 |
| Human- | Intramolecula | ATF4 | ATF4 | | | 100-200 | 800-900 |
| Human- | Intramolecula | ATG13 | ATG13 | | | 1300-1400 | 1600-1700 |

TABLE 3-continued

List of common human-human and human yeast interactions

| Organism | Type | Human Gene 1 | Human Gene 2 | Yeast gene1 | Yeast gene 2 | Region 1 | Region 2 |
|---|---|---|---|---|---|---|---|
| Human- | Intramolecula | ATG3 | ATG3 | | | 1200-1300 | 2800-2900 |
| Human- | Intramolecula | ATP5A1 | ATP5A1 | | | 100-200 | 500-600 |
| Human- | Intramolecula | ATP5B | ATP5B | | | 1000-1100 | 1100-1200 |
| Human- | Intramolecula | ATP5D | ATP5D | | | 500-600 | 900-1000 |
| Human- | Intramolecula | ATP5G3 | ATP5G3 | | | 400-500 | 1100-1200 |
| Human- | Intramolecula | ATP6V0B | ATP6V0B | | | 900-1000 | 1700-1800 |
| Human- | Intramolecula | BSG | BSG | | | 200-300 | 600-700 |
| Human- | Intramolecula | BTF3 | BTF3 | | | 100-200 | 300-400 |
| Human- | Intramolecula | C12orf57 | C12orf57 | | | 300-400 | 400-500 |
| Human- | Intramolecula | C14orf2 | C14orf2 | | | 0-100 | 300-400 |
| Human- | Intramolecula | C19orf70 | C19orf70 | | | 400-500 | 600-700 |
| Human- | Intramolecula | CALM2 | CALM2 | | | 4000-4100 | 4200-4300 |
| Human- | Intramolecula | CALM2 | CALM2 | | | 4100-4200 | 4300-4400 |
| Human- | Intramolecula | CCNB1IP1 | CCNB1IP1 | | | 400-500 | 600-700 |
| Human- | Intramolecula | CCNG1 | CCNC1 | | | 1400-1500 | 2100-2200 |
| Human- | Intramolecula | CCT2 | CCT2 | | | 1400-1500 | 1500-1600 |
| Human- | Intramolecula | CCT8 | CCT8 | | | 1400-1500 | 1800-1900 |
| Human- | Intramolecula | CCT8 | CCT8 | | | 800-900 | 900-1000 |
| Human- | Intramolecula | CD55 | CD55 | | | 1300-1400 | 1500-1600 |
| Human- | Intramolecula | CIRBP | CIRBP | | | 600-700 | 1000-1100 |
| Human- | Intramolecula | CNN2 | CNN2 | | | 700-800 | 800-900 |
| Human- | Intramolecula | COPZ1 | COPZ1 | | | 0-100 | 200-300 |
| Human- | Intramolecula | COX4I1 | COX4I1 | | | 200-300 | 700-800 |
| Human- | Intramolecula | COX7C | COX7C | | | 0-100 | 100-200 |
| Human- | Intramolecula | CTNNB1 | CTNNB1 | | | 2600-2700 | 3100-3200 |
| Human- | Intramolecula | DNPH1 | DNPH1 | | | 300-400 | 500-600 |
| Human- | Intramolecula | DYNC1I2 | DYNC1I2 | | | 500-600 | 600-700 |
| Human- | Intramolecula | EDF1 | EDF1 | | | 400-500 | 600-700 |
| Human- | Intramolecula | EEF1A1 | EEF1A1 | | | 0-100 | 100-200 |
| Human- | Intramolecula | EEF1A1 | EEF1A1 | | | 0-100 | 1100-1200 |
| Human- | Intramolecula | EEF1A1 | EEF1A1 | | | 0-100 | 1200-1300 |
| Human- | Intramolecula | EEF1A1 | EEF1A1 | | | 0-100 | 1300-1400 |
| Human- | Intramolecula | EEF1A1 | EEF1A1 | | | 0-100 | 1600-1700 |
| Human- | Intramolecula | EEF1A1 | EEF1A1 | | | 0-100 | 800-900 |
| Human- | Intramolecula | EEF1A1 | EEF1A1 | | | 1000-1100 | 1100-1200 |
| Human- | Intramolecula | EEF1A1 | EEF1A1 | | | 1000-1100 | 1200-1300 |
| Human- | Intramolecula | EEF1A1 | EEF1A1 | | | 1000-1100 | 1300-1400 |
| Human- | Intramolecula | EEF1A1 | EEF1A1 | | | 100-200 | 1100-1200 |
| Human- | Intramolecula | EEF1A1 | EEF1A1 | | | 100-200 | 1200-1300 |
| Human- | Intramolecula | EEF1A1 | EEF1A1 | | | 100-200 | 1400-1500 |
| Human- | Intramolecula | EEF1A1 | EEF1A1 | | | 100-200 | 1500-1600 |
| Human- | Intramolecula | EEF1A1 | EEF1A1 | | | 100-200 | 200-300 |
| Human- | Intramolecula | EEF1A1 | EEF1A1 | | | 100-200 | 400-500 |
| Human- | Intramolecula | EEF1A1 | EEF1A1 | | | 100-200 | 700-800 |
| Human- | Intramolecula | EEF1A1 | EEF1A1 | | | 100-200 | 800-900 |
| Human- | Intramolecula | EEF1A1 | EEF1A1 | | | 100-200 | 900-1000 |
| Human- | Intramolecula | EEF1A1 | EEF1A1 | | | 1100-1200 | 1200-1300 |
| Human- | Intramolecula | EEF1A1 | EEF1A1 | | | 1100-1200 | 1300-1400 |
| Human- | Intramolecula | EEF1A1 | EEF1A1 | | | 1100-1200 | 1400-1500 |
| Human- | Intramolecula | EEF1A1 | EEF1A1 | | | 1100-1200 | 1600-1700 |
| Human- | Intramolecula | EEF1A1 | EEF1A1 | | | 1200-1300 | 1300-1400 |
| Human- | Intramolecula | EEF1A1 | EEF1A1 | | | 1200-1300 | 1400-1500 |
| Human- | Intramolecula | EEF1A1 | EEF1A1 | | | 1200-1300 | 1500-1600 |
| Human- | Intramolecula | EEF1A1 | EEF1A1 | | | 1200-1300 | 1600-1700 |
| Human- | Intramolecula | EEF1A1 | EEF1A1 | | | 1300-1400 | 1400-1500 |
| Human- | Intramolecula | EEF1A1 | EEF1A1 | | | 1300-1400 | 1500-1600 |
| Human- | Intramolecula | EEF1A1 | EEF1A1 | | | 1300-1400 | 1700-1800 |
| Human- | Intramolecula | EEF1A1 | EEF1A1 | | | 1400-1500 | 1600-1700 |
| Human- | Intramolecula | EEF1A1 | EEF1A1 | | | 1400-1500 | 1700-1800 |
| Human- | Intramolecula | EEF1A1 | EEF1A1 | | | 1500-1600 | 1600-1700 |
| Human- | Intramolecula | EEF1A1 | EEF1A1 | | | 1500-1600 | 1700-1800 |
| Human- | Intramolecula | EEF1A1 | EEF1A1 | | | 1600-1700 | 1700-1800 |
| Human- | Intramolecula | EEF1A1 | EEF1A1 | | | 200-300 | 1000-1100 |
| Human- | Intramolecula | EEF1A1 | EEF1A1 | | | 200-300 | 1100-1200 |
| Human- | Intramolecula | EEF1A1 | EEF1A1 | | | 200-300 | 1200-1300 |
| Human- | Intramolecula | EEF1A1 | EEF1A1 | | | 200-300 | 1600-1700 |
| Human- | Intramolecula | EEF1A1 | EEF1A1 | | | 200-300 | 300-400 |
| Human- | Intramolecula | EEF1A1 | EEF1A1 | | | 200-300 | 400-500 |
| Human- | Intramolecula | EEF1A1 | EEF1A1 | | | 200-300 | 500-600 |
| Human- | Intramolecula | EEF1A1 | EEF1A1 | | | 200-300 | 900-1000 |
| Human- | Intramolecula | EEF1A1 | EEF1A1 | | | 300-400 | 1000-1100 |
| Human- | Intramolecula | EEF1A1 | EEF1A1 | | | 300-400 | 1100-1200 |
| Human- | Intramolecula | EEF1A1 | EEF1A1 | | | 300-400 | 1200-1300 |
| Human- | Intramolecula | EEF1A1 | EEF1A1 | | | 300-400 | 1400-1500 |
| Human- | Intramolecula | EEF1A1 | EEF1A1 | | | 300-400 | 1500-1600 |

TABLE 3-continued

List of common human-human and human yeast interactions

| Organism | Type | Human Gene 1 | Human Gene 2 | Yeast gene1 | Yeast gene 2 | Region 1 | Region 2 |
|---|---|---|---|---|---|---|---|
| Human- | Intramolecula | EEF1A1 | EEF1A1 | | | 300-400 | 400-500 |
| Human- | Intramolecula | EEF1A1 | EEF1A1 | | | 300-400 | 600-700 |
| Human- | Intramolecula | EEF1A1 | EEF1A1 | | | 300-400 | 900-1000 |
| Human- | Intramolecula | EEF1A1 | EEF1A1 | | | 400-500 | 1000-1100 |
| Human- | Intramolecula | EEF1A1 | EEF1A1 | | | 400-500 | 1100-1200 |
| Human- | Intramolecula | EEF1A1 | EEF1A1 | | | 400-500 | 1200-1300 |
| Human- | Intramolecula | EEF1A1 | EEF1A1 | | | 400-500 | 1300-1400 |
| Human- | Intramolecula | EEF1A1 | EEF1A1 | | | 400-500 | 1400-1500 |
| Human- | Intramolecula | EEF1A1 | EEF1A1 | | | 400-500 | 500-600 |
| Human- | Intramolecula | EEF1A1 | EEF1A1 | | | 400-500 | 600-700 |
| Human- | Intramolecula | EEF1A1 | EEF1A1 | | | 400-500 | 900-1000 |
| Human- | Intramolecula | EEF1A1 | EEF1A1 | | | 500-600 | 1100-1200 |
| Human- | Intramolecula | EEF1A1 | EEF1A1 | | | 500-600 | 1200-1300 |
| Human- | Intramolecula | EEF1A1 | EEF1A1 | | | 500-600 | 600-700 |
| Human- | Intramolecula | EEF1A1 | EEF1A1 | | | 500-600 | 700-800 |
| Human- | Intramolecula | EEF1A1 | EEF1A1 | | | 500-600 | 800-900 |
| Human- | Intramolecula | EEF1A1 | EEF1A1 | | | 600-700 | 1100-1200 |
| Human- | Intramolecula | EEF1A1 | EEF1A1 | | | 600-700 | 1200-1300 |
| Human- | Intramolecula | EEF1A1 | EEF1A1 | | | 600-700 | 700-800 |
| Human- | Intramolecula | EEF1A1 | EEF1A1 | | | 600-700 | 800-900 |
| Human- | Intramolecula | EEF1A1 | EEF1A1 | | | 600-700 | 900-1000 |
| Human | Intramolecula | EEF1A1 | EEF1A1 | | | 700-800 | 1000-1100 |
| Human- | Intramolecula | EEF1A1 | EEF1A1 | | | 700-800 | 1100-1200 |
| Human- | Intramolecula | EEF1A1 | EEF1A1 | | | 700-800 | 1200-1300 |
| Human- | Intramolecula | EEF1A1 | EEF1A1 | | | 700-800 | 800-900 |
| Human- | Intramolecula | EEF1A1 | EEF1A1 | | | 700-800 | 900-1000 |
| Human- | Intramolecula | EEF1A1 | EEF1A1 | | | 800-900 | 1000-1100 |
| Human- | Intramolecula | EEF1A1 | EEF1A1 | | | 800-900 | 1100-1200 |
| Human- | Intramolecula | EEF1A1 | EEF1A1 | | | 800-900 | 1200-1300 |
| Human- | Intramolecula | EEF1A1 | EEF1A1 | | | 800-900 | 900-1000 |
| Human- | Intramolecula | EEF1A1 | EEF1A1 | | | 900-1000 | 1000-1100 |
| Human- | Intramolecula | EEF1A1 | EEF1A1 | | | 900-1000 | 1100-1200 |
| Human- | Intramolecula | EEF1A1 | EEF1A1 | | | 900-1000 | 1200-1300 |
| Human- | Intramolecula | EEF1A1 | EEF1A1 | | | 900-1000 | 1300-1400 |
| Human- | Intramolecula | EEF1B2 | EEF1B2 | | | 0-100 | 300-400 |
| Human- | Intramolecula | EEF1B2 | EEF1B2 | | | 300-400 | 1000-1100 |
| Human- | Intramolecula | EEF1B2 | EEF1B2 | | | 300-400 | 900-1000 |
| Human- | Intramolecula | EEF1B2 | EEF1B2 | | | 500-600 | 800-900 |
| Human- | Intramolecula | EEF1D | EEF1D | | | 1600-1700 | 1700-1800 |
| Human- | Intramolecula | EEF1D | EEF1D | | | 200-300 | 2000-2100 |
| Human- | Intramolecula | EEF1G | EEF1G | | | 1000-1100 | 1200-1300 |
| Human- | Intramolecula | EEF1G | EEF1G | | | 100-200 | 300-400 |
| Human- | Intramolecula | EEF1G | EEF1G | | | 1100-1200 | 1200-1300 |
| Human- | Intramolecula | EEF1G | EEF1G | | | 1200-1300 | 1300-1400 |
| Human- | Intramolecula | EEF1G | EEF1G | | | 1200-1300 | 1400-1500 |
| Human- | Intramolecula | EEF1G | EEF1G | | | 300-400 | 1100-1200 |
| Human- | Intramolecula | EEF1G | EEF1G | | | 300-400 | 1400-1500 |
| Human- | Intramolecula | EEF1G | EEF1G | | | 300-400 | 600-700 |
| Human- | Intramolecula | EEF1G | EEF1G | | | 400-500 | 1200-1300 |
| Human- | Intramolecula | EEF1G | EEF1G | | | 400-500 | 1400-1500 |
| Human- | Intramolecula | EEF1G | EEF1G | | | 500-600 | 700-800 |
| Human- | Intramolecula | EEF2 | EEF2 | | | 1200-1300 | 2500-2600 |
| Human- | Intramolecula | EEF2 | EEF2 | | | 1200-1300 | 3000-3100 |
| Human- | Intramolecula | EEF2 | EEF2 | | | 1300-1400 | 1400-1500 |
| Human- | Intramolecula | EEF2 | EEF2 | | | 1400-1500 | 2800-2900 |
| Human- | Intramolecula | EEF2 | EEF2 | | | 200-300 | 400-500 |
| Human- | Intramolecula | EEF2 | EEF2 | | | 2700-2800 | 3000-3100 |
| Human- | Intramolecula | EEF2 | EEF2 | | | 2800-2900 | 3000-3100 |
| Human- | Intramolecula | EIF2B2 | EIF2B2 | | | 1300-1400 | 1400-1500 |
| Human- | Intramolecula | EIF4A2 | EIF4A2 | | | 1200-1300 | 1300-1400 |
| Human- | Intramolecula | EIF4A2 | EIF4A2 | | | 400-500 | 500-600 |
| Human- | Intramolecula | EIF4B | EIF4B | | | 2800-2900 | 3200-3300 |
| Human- | Intramolecula | EIF4B | EIF4B | | | 3000-3100 | 3100-3200 |
| Human- | Intramolecula | EIF4E | EIF4E | | | 1800-1900 | 2000-2100 |
| Human- | Intramolecula | EIF4E | EIF4E | | | 1900-2000 | 2000-2100 |
| Human- | Intramolecula | EIF4H | EIF4H | | | 1200-1300 | 2200-2300 |
| Human- | Intramolecula | ELP5 | ELP5 | | | 1100-1200 | 1800-1900 |
| Human- | Intramolecula | ENO1 | ENO1 | | | 1500-1600 | 1600-1700 |
| Human- | Intramolecula | ENO1 | ENO1 | | | 2000-2100 | 2200-2300 |
| Human- | Intramolecula | ENO1 | ENO1 | | | 2300-2400 | 2400-2500 |
| Human- | Intramolecula | FAM195B | FAM195B | | | 400-500 | 700-800 |
| Human- | Intramolecula | FTH1 | FTH1 | | | 700-800 | 800-900 |
| Human- | Intramolecula | FTL | FTL | | | 100-200 | 300-400 |
| Human- | Intramolecula | FTL | FTL | | | 500-600 | 700-800 |
| Human- | Intramolecula | FXR1 | FXR1 | | | 200-300 | 600-700 |

TABLE 3-continued

List of common human-human and human yeast interactions

| Organism | Type | Human Gene 1 | Human Gene 2 | Yeast gene1 | Yeast gene 2 | Region 1 | Region 2 |
|---|---|---|---|---|---|---|---|
| Human- | Intramolecula | FXYD5 | FXYD5 | | | 0-100 | 100-200 |
| Human- | Intramolecula | GAPDH | GAPDH | | | 100-200 | 200-300 |
| Human- | Intramolecula | GAPDH | GAPDH | | | 1100-1200 | 1300-1400 |
| Human- | Intramolecula | GAPDH | GAPDH | | | 1200-1300 | 1400-1500 |
| Human- | Intramolecula | GAPDH | GAPDH | | | 300-400 | 400-500 |
| Human- | Intramolecula | GAPDH | GAPDH | | | 500-600 | 1100-1200 |
| Human- | Intramolecula | GAPDH | GAPDH | | | 500-600 | 1200-1300 |
| Human- | Intramolecula | GAPDH | GAPDH | | | 700-800 | 1000-1100 |
| Human- | Intramolecula | GLUL | GLUL | | | 2700-2800 | 2900-3000 |
| Human- | Intramolecula | GLUL | GLUL | | | 500-600 | 900-1000 |
| Human- | Intramolecula | GMPR2 | GMPR2 | | | 500-600 | 700-800 |
| Human- | Intramolecula | GNB2L1 | GNB2L1 | | | 300-400 | 400-500 |
| Human- | Intramolecula | GNB2L1 | GNB2L1 | | | 500-600 | 1000-1100 |
| Human- | Intramolecula | GPX1 | GPX1 | | | 300-400 | 600-700 |
| Human- | Intramolecula | H3F3B | H3F3B | | | 1100-1200 | 1300-1400 |
| Human- | Intramolecula | HMGA1 | HMGA1 | | | 0-100 | 300-400 |
| Human- | Intramolecula | HMGA1 | HMGA1 | | | 0-100 | 400-500 |
| Human- | Intramolecula | HMGB1 | HMGB1 | | | 1700-1800 | 2100-2200 |
| Human- | Intramolecula | HMGN2 | HMGN2 | | | 600-700 | 800-900 |
| Human- | Intramolecula | HN1L | HN1L | | | 2800-2900 | 2900-3000 |
| Human- | Intramolecula | HNRNPA1 | HNRNPA1 | | | 1600-1700 | 1800-1900 |
| Human- | Intramolecula | HNRNPA2B1 | HNRNPA2B1 | | | 2500-2600 | 3200-3300 |
| Human- | Intramolecula | HNRNPC | HNRNPC | | | 1000-1100 | 1300-1400 |
| Human- | Intramolecula | HNRNPD | HNRNPD | | | 1100-1200 | 1300-1400 |
| Human- | Intramolecula | HNRNPK | HNRNPK | | | 2300-2400 | 2600-2700 |
| Human- | Intramolecula | HNRNPU | HNRNPU | | | 3100-3200 | 3300-3400 |
| Human- | Intramolecula | HSD17B4 | HSD17B4 | | | 100-200 | 300-400 |
| Human- | Intramolecula | HSD17B4 | HSD17B4 | | | 300-400 | 400-500 |
| Human- | Intramolecula | | hsnma-RNU1-1hsnma-RNU1-1 | | | 0-100 | 100-200 |
| Human- | Intramolecula | HSP90AA1 | HSP90AA1 | | | 3000-3100 | 3500-3600 |
| Human- | Intramolecula | HSPA8 | HSPA8 | | | 2200-2300 | 2300-2400 |
| Human- | Intramolecula | | HSU13369-5ETSHSU13369-5ETS | | | 1800-1900 | 2700-2800 |
| Human- | Intramolecula | | HSU13369-ITS2HSU13369-ITS2 | | | 200-300 | 700-800 |
| Human- | Intramolecula | | HSU13369-ITS2HSU13369-ITS2 | | | 300-400 | 700-800 |
| Human- | Intramolecula | | HSU13369-ITS2HSU13369-ITS2 | | | 400-500 | 700-800 |
| Human- | Intramolecula | IDH3B | IDH3B | | | 1200-1300 | 1400-1500 |
| Human- | Intramolecula | INTS6 | INTS6 | | | 1000-1100 | 1300-1400 |
| Human- | Intramolecula | IP6K2 | IP6K2 | | | 0-100 | 300-400 |
| Human- | Intramolecula | ISCU | ISCU | | | 1500-1600 | 1600-1700 |
| Human- | Intramolecula | LDHA | LDHA | | | 1400-1500 | 1900-2000 |
| Human- | Intramolecula | LDHB | LDHB | | | 0-100 | 300-400 |
| Human- | Intramolecula | LDHB | LDHB | | | 1300-1400 | 1400-1500 |
| Human- | Intramolecula | | LRRC75A-AS1LRRC75A-AS1 | | | 0-100 | 300-400 |
| Human- | Intramolecula | | LRRC75A-AS1LRRC75A-AS1 | | | 1000-1100 | 1100-1200 |
| Human- | Intramolecula | | LRRC75A-AS1LRRC75A-AS1 | | | 1000-1100 | 1200-1300 |
| Human- | Intramolecula | | LRRC75A-AS1LRRC75A-AS1 | | | 300-400 | 600-700 |
| Human- | Intramolecula | | LRRC75A-AS1LRRC75A-AS1 | | | 400-500 | 600-700 |
| Human- | Intramolecula | MCM4 | MCM4 | | | 3800-3900 | 4300-4400 |
| Human- | Intramolecula | METTL17 | METTL17 | | | 1400-1500 | 1500-1600 |
| Human- | Intramolecula | MINOS1 | MINOS1 | | | 200-300 | 500-600 |
| Human- | Intramolecula | MORF4L1 | MORF4L1 | | | 300-400 | 500-600 |
| Human- | Intramolecula | MRFAP1 | MRFAP1 | | | 1300-1400 | 2000-2100 |
| Human- | Intramolecula | MRFAP1 | MRFAP1 | | | 1300-1400 | 2100-2200 |
| Human- | Intramolecula | MRFAP1 | MRFAP1 | | | 600-700 | 700-800 |
| Human- | Intramolecula | MRPL11 | MRPL11 | | | 500-600 | 600-700 |
| Human- | Intramolecula | MTCH1 | MTCH1 | | | 1200-1300 | 1300-1400 |
| Human- | Intramolecula | MYL12A | MYL12A | | | 300-400 | 400-500 |
| Human- | Intramolecula | MYL6 | MYL6 | | | 500-600 | 600-700 |
| Human- | Intramolecula | NAP1L1 | NAP1L1 | | | 1600-1700 | 2300-2400 |
| Human- | Intramolecula | NAP1L1 | NAP1L1 | | | 1600-1700 | 2400-2500 |
| Human- | Intramolecula | NDUFS2 | NDUFS2 | | | 1500-1600 | 1800-1900 |
| Human- | Intramolecula | NIPA2 | NIPA2 | | | 200-300 | 700-800 |
| Human- | Intramolecula | NONO | NONO | | | 2200-2300 | 2700-2800 |
| Human- | Intramolecula | NONO | NONO | | | 500-600 | 700-800 |
| Human- | Intramolecula | OAZ1 | OAZ1 | | | 700-800 | 800-900 |

TABLE 3-continued

List of common human-human and human yeast interactions

| Organism | Type | Human Gene 1 | Human Gene 2 | Yeast gene1 | Yeast gene 2 | Region 1 | Region 2 |
|---|---|---|---|---|---|---|---|
| Human- | Intramolecula | PAICS | PAICS | | | 2000-2100 | 2700-2800 |
| Human- | Intramolecula | PAICS | PAICS | | | 2100-2200 | 2700-2800 |
| Human- | Intramolecula | PDK1 | PDK1 | | | 500-600 | 600-700 |
| Human- | Intramolecula | PFN1 | PFN1 | | | 900-1000 | 1100-1200 |
| Human- | Intramolecula | PGAM1 | PGAM1 | | | 1100-1200 | 1200-1300 |
| Human- | Intramolecula | PGK1 | PGK1 | | | 1600-1700 | 1700-1800 |
| Human- | Intramolecula | PHPT1 | PHPT1 | | | 800-900 | 900-1000 |
| Human- | Intramolecula | PKM | PKM | | | 200-300 | 600-700 |
| Human- | Intramolecula | PKM | PKM | | | 2200-2300 | 2600-2700 |
| Human- | Intramolecula | PKM | PKM | | | 2300-2400 | 2600-2700 |
| Human- | Intramolecula | POLR2F | POLR2F | | | 100-200 | 300-400 |
| Human- | Intramolecula | PPIA | PPIA | | | 100-200 | 300-400 |
| Human- | Intramolecula | PPIA | PPIA | | | 600-700 | 800-900 |
| Human- | Intramolecula | PPP1CC | PPP1CC | | | 400-500 | 500-600 |
| Human- | Intramolecula | PRDX1 | PRDX1 | | | 0-100 | 300-400 |
| Human- | Intramolecula | PRMT1 | PRMT1 | | | 100-200 | 200-300 |
| Human- | Intramolecula | PSMB5 | PSMB5 | | | 700-800 | 800-900 |
| Human- | Intramolecula | PSMD13 | PSMD13 | | | 300-400 | 400-500 |
| Human- | Intramolecula | PTGES3 | PTGES3 | | | 1100-1200 | 1500-1600 |
| Human- | Intramolecula | PTMA | PTMA | | | 600-700 | 900-1000 |
| Human- | Intramolecula | RAC1 | RAC1 | | | 400-500 | 500-600 |
| Human- | Intramolecula | RAN | RAN | | | 600-700 | 900-1000 |
| Human- | Intramolecula | RAP1B | RAP1B | | | 1700-1800 | 1900-2000 |
| Human- | Intramolecula | RHOA | RHOA | | | 1200-1300 | 1300-1400 |
| Human- | Intramolecula | RPA2 | RPA2 | | | 400-500 | 600-700 |
| Human- | Intramolecula | RPL10A | RPL10A | | | 0-100 | 200-300 |
| Human- | Intramolecula | RPL10 | RPL10 | | | 500-600 | 700-800 |
| Human- | Intramolecula | RPL10 | RPL10 | | | 600-700 | 800-900 |
| Human- | Intramolecula | RPL11 | RPL11 | | | 300-400 | 500-600 |
| Human- | Intramolecula | RPL11 | RPL11 | | | 300-400 | 600-700 |
| Human- | Intramolecula | RPL11 | RPL11 | | | 400-500 | 500-600 |
| Human- | Intramolecula | RPL12 | RPL12 | | | 400-500 | 500-600 |
| Human- | Intramolecula | RPL13A | RPL13A | | | 0-100 | 300-400 |
| Human- | Intramolecula | RPL13A | RPL13A | | | 1000-1100 | 1100-1200 |
| Human- | Intramolecula | RPL13A | RPL13A | | | 900-1000 | 1100-1200 |
| Human- | Intramolecula | RPL13 | RPL13 | | | 200-300 | 400-500 |
| Human- | Intramolecula | RPL13 | RPL13 | | | 200-300 | 700-800 |
| Human- | Intramolecula | RPL13 | RPL13 | | | 200-300 | 800-900 |
| Human- | Intramolecula | RPL13 | RPL13 | | | 300-400 | 400-500 |
| Human- | Intramolecula | RPL13 | RPL13 | | | 300-400 | 500-600 |
| Human- | Intramolecula | RPL14 | RPL14 | | | 0-100 | 100-200 |
| Human- | Intramolecula | RPL14 | RPL14 | | | 100-200 | 300-400 |
| Human- | Intramolecula | RPL15 | RPL15 | | | 500-600 | 600-700 |
| Human- | Intramolecula | RPL15 | RPL15 | | | 500-600 | 700-800 |
| Human- | Intramolecula | RPL18A | RPL18A | | | 0-100 | 100-200 |
| Human- | Intramolecula | RPL18A | RPL18A | | | 0-100 | 200-300 |
| Human- | Intramolecula | RPL18A | RPL18A | | | 0-100 | 400-500 |
| Human- | Intramolecula | RPL18A | RPL18A | | | 100-200 | 300-400 |
| Human- | Intramolecula | RPL18A | RPL18A | | | 200-300 | 300-400 |
| Human- | Intramolecula | RPL18A | RPL18A | | | 200-300 | 400-500 |
| Human- | Intramolecula | RPL18A | RPL18A | | | 200-300 | 500-600 |
| Human- | Intramolecula | RPL18A | RPL18A | | | 300-400 | 500-600 |
| Human- | Intramolecula | RPL18 | RPL18 | | | 400-500 | 500-600 |
| Human- | Intramolecula | RPL18 | RPL18 | | | 500-600 | 700-800 |
| Human- | Intramolecula | RPL19 | RPL19 | | | 0-100 | 500-600 |
| Human- | Intramolecula | RPL19 | RPL19 | | | 400-500 | 600-700 |
| Human- | Intramolecula | RPL19 | RPL19 | | | 400-500 | 700-800 |
| Human- | Intramolecula | RPL24 | RPL24 | | | 0-100 | 400-500 |
| Human- | Intramolecula | RPL24 | RPL24 | | | 0-100 | 500-600 |
| Human- | Intramolecula | RPL26 | RPL26 | | | 100-200 | 300-400 |
| Human- | Intramolecula | RPL27A | RPL27A | | | 500-600 | 700-800 |
| Human- | Intramolecula | RPL27A | RPL27A | | | 500-600 | 800-900 |
| Human- | Intramolecula | RPL27A | RPL27A | | | 600-700 | 700-800 |
| Human- | Intramolecula | RPL27 | RPL27 | | | 0-100 | 100-200 |
| Human- | Intramolecula | RPL27 | RPL27 | | | 0-100 | 300-400 |
| Human- | Intramolecula | RPL27 | RPL27 | | | 300-400 | 400-500 |
| Human- | Intramolecula | RPL28 | RPL28 | | | 300-400 | 500-600 |
| Human- | Intramolecula | RPL29 | RPL29 | | | 0-100 | 300-400 |
| Human- | Intramolecula | RPL29 | RPL29 | | | 0-100 | 400-500 |
| Human- | Intramolecula | RPL29 | RPL29 | | | 0-100 | 500-600 |
| Human- | Intramolecula | RPL29 | RPL29 | | | 400-500 | 500-600 |
| Human- | Intramolecula | RPL32 | RPL32 | | | 200-300 | 300-400 |
| Human- | Intramolecula | RPL34 | RPL34 | | | 100-200 | 300-400 |
| Human- | Intramolecula | RPL37A | RPL37A | | | 0-100 | 300-400 |
| Human- | Intramolecula | RPL37 | RPL37 | | | 200-300 | 300-400 |

TABLE 3-continued

List of common human-human and human yeast interactions

| Organism | Type | Human Gene 1 | Human Gene 2 | Yeast gene1 | Yeast gene 2 | Region 1 | Region 2 |
|---|---|---|---|---|---|---|---|
| Human- | Intramolecula | RPL37 | RPL37 | | | 200-300 | 400-500 |
| Human- | Intramolecula | RPL38 | RPL38 | | | 0-100 | 100-200 |
| Human- | Intramolecula | RPL39 | RPL39 | | | 0-100 | 300-400 |
| Human- | Intramolecula | RPL39 | RPL39 | | | 200-300 | 300-400 |
| Human- | Intramolecula | RPL39 | RPL39 | | | 200-300 | 400-500 |
| Human- | Intramolecula | RPL3 | RPL3 | | | 1000-1100 | 1100-1200 |
| Human- | Intramolecula | RPL3 | RPL3 | | | 1000-1100 | 1200-1300 |
| Human- | Intramolecula | RPL3 | RPL3 | | | 100-200 | 600-700 |
| Human- | Intramolecula | RPL3 | RPL3 | | | 200-300 | 500-600 |
| Human- | Intramolecula | RPL3 | RPL3 | | | 300-400 | 1000-1100 |
| Human- | Intramolecula | RPL3 | RPL3 | | | 300-400 | 500-600 |
| Human- | Intramolecula | RPL3 | RPL3 | | | 300-400 | 700-800 |
| Human- | Intramolecula | RPL3 | RPL3 | | | 600-700 | 1000-1100 |
| Human- | Intramolecula | RPL3 | RPL3 | | | 600-700 | 800-900 |
| Human- | Intramolecula | RPL3 | RPL3 | | | 900-1000 | 1000-1100 |
| Human- | Intramolecula | RPL3 | RPL3 | | | 900-1000 | 1200-1300 |
| Human- | Intramolecula | RPL41 | RPL41 | | | 0-100 | 200-300 |
| Human- | Intramolecula | RPL41 | RPL41 | | | 200-300 | 400-500 |
| Human- | Intramolecula | RPL41 | RPL41 | | | 200-300 | 500-600 |
| Human- | Intramolecula | RPL41 | RPL41 | | | 300-400 | 400-500 |
| Human- | Intramolecula | RPL41 | RPL41 | | | 300-400 | 500-600 |
| Human- | Intramolecula | RPL4 | RPL4 | | | 200-300 | 400-500 |
| Human- | Intramolecula | RPL4 | RPL4 | | | 300-400 | 400-500 |
| Human- | Intramolecula | RPL4 | RPL4 | | | 500-600 | 1300-1400 |
| Human- | Intramolecula | RPL4 | RPL4 | | | 600-700 | 1000-1100 |
| Human- | Intramolecula | RPL4 | RPL4 | | | 600-700 | 1300-1400 |
| Human- | Intramolecula | RPL4 | RPL4 | | | 500-700 | 800-900 |
| Human- | Intramolecula | RPL4 | RPL4 | | | 700-800 | 800-900 |
| Human- | Intramolecula | RPL4 | RPL4 | | | 700-800 | 900-1000 |
| Human- | Intramolecula | RPL4 | RPL4 | | | 800-900 | 1000-1100 |
| Human- | Intramolecula | RPL4 | RPL4 | | | 800-900 | 900-1000 |
| Human- | Intramolecula | RPL5 | RPL5 | | | 100-200 | 300-400 |
| Human- | Intramolecula | RPL5 | RPL5 | | | 300-400 | 400-500 |
| Human- | Intramolecula | RPL5 | RPL5 | | | 300-400 | 500-600 |
| Human- | Intramolecula | RPL5 | RPL5 | | | 500-600 | 900-1000 |
| Human- | Intramolecula | RPL5 | RPL5 | | | 600-700 | 900-1000 |
| Human- | Intramolecula | RPL6 | RPL6 | | | 500-600 | 600-700 |
| Human- | Intramolecula | RPL6 | RPL6 | | | 900-1000 | 1000-1100 |
| Human- | Intramolecula | RPL7A | RPL7A | | | 100-200 | 700-800 |
| Human- | Intramolecula | RPL7A | RPL7A | | | 400-500 | 500-600 |
| Human- | Intramolecula | RPL7A | RPL7A | | | 500-600 | 700-800 |
| Human- | Intramolecula | RPL7 | RPL7 | | | 100-200 | 500-600 |
| Human- | Intramolecula | RPL7 | RPL7 | | | 200-300 | 300-400 |
| Human- | Intramolecula | RPL7 | RPL7 | | | 400-500 | 500-600 |
| Human- | Intramolecula | RPL9 | RPL9 | | | 200-300 | 500-600 |
| Human- | Intramolecula | RPL9 | RPL9 | | | 300-400 | 400-500 |
| Human- | Intramolecula | RPL9 | RPL9 | | | 500-600 | 600-700 |
| Human- | Intramolecula | RPL9 | RPL9 | | | 500-600 | 700-800 |
| Human- | Intramolecula | RPLP0 | RPLP0 | | | 1000-1100 | 1100-1200 |
| Human- | Intramolecula | RPLP0 | RPLP0 | | | 100-200 | 200-300 |
| Human- | Intramolecula | RPLP0 | RPLP0 | | | 300-400 | 1000-1100 |
| Human- | Intramolecula | RPLP0 | RPLP0 | | | 300-400 | 500-600 |
| Human- | Intramolecula | RPLP0 | RPLP0 | | | 300-400 | 800-900 |
| Human- | Intramolecula | RPLP0 | RPLP0 | | | 300-400 | 900-1000 |
| Human- | Intramolecula | RPLP0 | RPLP0 | | | 400-500 | 600-700 |
| Human- | Intramolecula | RPLP0 | RPLP0 | | | 400-500 | 700-800 |
| Human- | Intramolecula | RPLP0 | RPLP0 | | | 400-500 | 800-900 |
| Human- | Intramolecula | RPLP0 | RPLP0 | | | 500-600 | 700-800 |
| Human- | Intramolecula | RPLP0 | RPLP0 | | | 600-700 | 900-1000 |
| Human- | Intramolecula | RPLP0 | RPLP0 | | | 800-900 | 900-1000 |
| Human- | Intramolecula | RPLP1 | RPLP1 | | | 0-100 | 200-300 |
| Human- | Intramolecula | RPLP1 | RPLP1 | | | 100-200 | 200-300 |
| Human- | Intramolecula | RPLP1 | RPLP1 | | | 100-200 | 300-400 |
| Human- | Intramolecula | RPLP1 | RPLP1 | | | 100-200 | 400-500 |
| Human- | Intramolecula | RPLP1 | RPLP1 | | | 200-300 | 400-500 |
| Human- | Intramolecula | RPLP2 | RPLP2 | | | 100-200 | 200-300 |
| Human- | Intramolecula | RPS11 | RPS11 | | | 0-100 | 400-500 |
| Human- | Intramolecula | RPS11 | RPS11 | | | 0-100 | 500-600 |
| Human- | Intramolecula | RPS12 | RPS12 | | | 0-100 | 400-500 |
| Human- | Intramolecula | RPS12 | RPS12 | | | 100-200 | 300-400 |
| Human- | Intramolecula | RPS12 | RPS12 | | | 100-200 | 400-500 |
| Human- | Intramolecula | RPS12 | RPS12 | | | 200-300 | 300-400 |
| Human- | Intramolecula | RPS12 | RPS12 | | | 200-300 | 400-500 |
| Human- | Intramolecula | RPS13 | RPS13 | | | 0-100 | 200-300 |
| Human- | Intramolecula | RPS13 | RPS13 | | | 200-300 | 400-500 |

TABLE 3-continued

List of common human-human and human yeast interactions

| Organism | Type | Human Gene 1 | Human Gene 2 | Yeast gene1 | Yeast gene 2 | Region 1 | Region 2 |
|---|---|---|---|---|---|---|---|
| Human- | Intramolecula | RPS13 | RPS13 | | | 200-300 | 500-600 |
| Human- | Intramolecula | RPS13 | RPS13 | | | 300-400 | 400-500 |
| Human- | Intramolecula | RPS14 | RPS14 | | | 300-400 | 400-500 |
| Human- | Intramolecula | RPS14 | RPS14 | | | 300-400 | 500-600 |
| Human- | Intramolecula | RPS15A | RPS15A | | | 0-100 | 100-200 |
| Human- | Intramolecula | RPS15A | RPS15A | | | 0-100 | 300-400 |
| Human- | Intramolecula | RPS15A | RPS15A | | | 100-200 | 200-300 |
| Human- | Intramolecula | RPS15A | RPS15A | | | 200-300 | 400-500 |
| Human- | Intramolecula | RPS16 | RPS16 | | | 0-100 | 100-200 |
| Human- | Intramolecula | RPS16 | RPS16 | | | 0-100 | 200-300 |
| Human- | Intramolecula | RPS16 | RPS16 | | | 0-100 | 400-500 |
| Human- | Intramolecula | RPS16 | RPS16 | | | 0-100 | 500-600 |
| Human- | Intramolecula | RPS16 | RPS16 | | | 200-300 | 300-400 |
| Human- | Intramolecula | RPS16 | RPS16 | | | 200-300 | 500-600 |
| Human- | Intramolecula | RPS17 | RPS17 | | | 200-300 | 500-600 |
| Human- | Intramolecula | RPS17 | RPS17 | | | 300-400 | 500-600 |
| Human- | Intramolecula | RPS19 | RPS19 | | | 400-500 | 600-700 |
| Human- | Intramolecula | RPS19 | RPS19 | | | 400-500 | 700-800 |
| Human- | Intramolecula | RPS19 | RPS19 | | | 500-600 | 600-700 |
| Human- | Intramolecula | RPS20 | RPS20 | | | 100-200 | 200-300 |
| Human- | Intramolecula | RPS20 | RPS20 | | | 300-400 | 400-500 |
| Human- | Intramolecula | RPS21 | RPS21 | | | 200-300 | 300-400 |
| Human- | Intramolecula | RPS23 | RPS23 | | | 200-300 | 400-500 |
| Human- | Intramolecula | RPS24 | RPS24 | | | 200-300 | 300-400 |
| Human- | Intramolecula | RPS25 | RPS25 | | | 0-100 | 100-200 |
| Human- | Intramolecula | RPS25 | RPS25 | | | 0-100 | 200-300 |
| Human- | Intramolecula | RPS27A | RPS27A | | | 500-600 | 600-700 |
| Human- | Intramolecula | RPS27A | RPS27A | | | 600-700 | 700-800 |
| Human- | Intramolecula | RPS27 | RPS27 | | | 0-100 | 100-200 |
| Human- | Intramolecula | RPS28 | RPS28 | | | 0-100 | 200-300 |
| Human- | Intramolecula | RPS29 | RPS29 | | | 0-100 | 100-200 |
| Human- | Intramolecula | RPS29 | RPS29 | | | 0-100 | 200-300 |
| Human- | Intramolecula | RPS2 | RPS2 | | | 0-100 | 600-700 |
| Human- | Intramolecula | RPS2 | RPS2 | | | 0-100 | 800-900 |
| Human- | Intramolecula | RPS2 | RPS2 | | | 100-200 | 600-700 |
| Human- | Intramolecula | RPS2 | RPS2 | | | 200-300 | 600-700 |
| Human- | Intramolecula | RPS2 | RPS2 | | | 200-300 | 700-800 |
| Human- | Intramolecula | RPS2 | RPS2 | | | 300-400 | 500-600 |
| Human- | Intramolecula | RPS2 | RPS2 | | | 300-400 | 600-700 |
| Human- | Intramolecula | RPS2 | RPS2 | | | 300-400 | 700-800 |
| Human- | Intramolecula | RPS2 | RPS2 | | | 400-500 | 500-600 |
| Human- | Intramolecula | RPS2 | RPS2 | | | 600-700 | 700-800 |
| Human- | Intramolecula | RPS2 | RPS2 | | | 600-700 | 800-900 |
| Human- | Intramolecula | RPS2 | RPS2 | | | 700-800 | 800-900 |
| Human- | Intramolecula | RPS2 | RPS2 | | | 700-800 | 900-1000 |
| Human- | Intramolecula | RPS3A | RPS3A | | | 400-500 | 1500-1600 |
| Human- | Intramolecula | RPS3 | RPS3 | | | 0-100 | 900-1000 |
| Human- | Intramolecula | RPS3 | RPS3 | | | 100-200 | 800-900 |
| Human- | Intramolecula | RPS3 | RPS3 | | | 200-300 | 300-400 |
| Human- | Intramolecula | RPS3 | RPS3 | | | 200-300 | 400-500 |
| Human- | Intramolecula | RPS3 | RPS3 | | | 300-400 | 700-800 |
| Human- | Intramolecula | RPS3 | RPS3 | | | 400-500 | 600-700 |
| Human- | Intramolecula | RPS3 | RPS3 | | | 400-500 | 800-900 |
| Human- | Intramolecula | RPS3 | RPS3 | | | 500-600 | 600-700 |
| Human- | Intramolecula | RPS4X | RPS4X | | | 100-200 | 700-800 |
| Human- | Intramolecula | RPS4X | RPS4X | | | 200-300 | 600-700 |
| Human- | Intramolecula | RPS5 | RPS5 | | | 400-500 | 500-600 |
| Human- | Intramolecula | RPS6 | RPS6 | | | 0-100 | 100-200 |
| Human- | Intramolecula | RPS6 | RPS6 | | | 0-100 | 700-800 |
| Human- | Intramolecula | RPS6 | RPS6 | | | 100-200 | 500-600 |
| Human- | Intramolecula | RPS6 | RPS6 | | | 100-200 | 600-700 |
| Human- | Intramolecula | RPS6 | RPS6 | | | 200-300 | 400-500 |
| Human- | Intramolecula | RPS6 | RPS6 | | | 200-300 | 500-600 |
| Human- | Intramolecula | RPS7 | RPS7 | | | 200-300 | 300-400 |
| Human- | Intramolecula | RPS7 | RPS7 | | | 200-300 | 400-500 |
| Human- | Intramolecula | RPS8 | RPS8 | | | 0-100 | 500-600 |
| Human- | Intramolecula | RPS8 | RPS8 | | | 200-300 | 300-400 |
| Human- | Intramolecula | RPS8 | RPS8 | | | 200-300 | 600-700 |
| Human- | Intramolecula | RPS8 | RPS8 | | | 300-400 | 500-600 |
| Human- | Intramolecula | RPS8 | RPS8 | | | 300-400 | 600-700 |
| Human- | Intramolecula | RPS9 | RPS9 | | | 0-100 | 600-700 |
| Human- | Intramolecula | RPS9 | RPS9 | | | 400-500 | 600-700 |
| Human- | Intramolecula | RSL24D1 | RSL24D1 | | | 700-800 | 900-1000 |
| Human- | Intramolecula | SDHC | SDHC | | | 0-100 | 200-300 |
| Human- | Intramolecula | SDHD | SDHD | | | 300-400 | 500-600 |

TABLE 3-continued

List of common human-human and human yeast interactions

| Organism | Type | Human Gene 1 | Human Gene 2 | Yeast gene1 | Yeast gene 2 | Region 1 | Region 2 |
|---|---|---|---|---|---|---|---|
| Human- | Intramolecula | SEC11A | SEC11A | | | 400-500 | 500-600 |
| Human- | Intramolecula | SEC11A | SEC11A | | | 400-500 | 600-700 |
| Human- | Intramolecula | SEC61G | SEC61G | | | 300-400 | 400-500 |
| Human- | Intramolecula | SEPT7 | SEPT7 | | | 1500-1600 | 1800-1900 |
| Human- | Intramolecula | SKP1 | SKP1 | | | 600-700 | 1300-1400 |
| Human- | Intramolecula | SLC25A3 | SLC25A3 | | | 0-100 | 300-400 |
| Human- | Intramolecula | SLC25A3 | SLC25A3 | | | 500-600 | 600-700 |
| Human- | Intramolecula | SLC25A6 | SLC25A6 | | | 500-600 | 700-800 |
| Human- | Intramolecula | SLC41A3 | SLC41A3 | | | 1500-1600 | 2100-2200 |
| Human- | Intramolecula | SNHG16 | SNHG16 | | | 0-100 | 200-300 |
| Human- | Intramolecula | SNRPB | SNRPB | | | 800-900 | 1000-1100 |
| Human- | Intramolecula | SNRPD2 | SNRPD2 | | | 200-300 | 400-500 |
| Human- | Intramolecula | SNX3 | SNX3 | | | 800-900 | 1100-1200 |
| Human- | Intramolecula | SNX5 | SNX5 | | | 0-100 | 300-400 |
| Human- | Intramolecula | SRSF3 | SRSF3 | | | 800-900 | 1300-1400 |
| Human- | Intramolecula | STUB1 | STUB1 | | | 500-600 | 600-700 |
| Human- | Intramolecula | TCP1 | TCP1 | | | 900-1000 | 1100-1200 |
| Human- | Intramolecula | TKT | TKT | | | 400-500 | 500-600 |
| Human- | Intramolecula | TMBIM6 | TMBIM6 | | | 1700-1800 | 2100-2200 |
| Human- | Intramolecula | TMEM147 | TMEM147 | | | 100-200 | 300-400 |
| Human- | Intramolecula | TMEM147 | TMEM147 | | | 200-300 | 300-400 |
| Human- | Intramolecula | TMEM9 | TMEM9 | | | 100-200 | 600-700 |
| Human- | Intramolecula | TMPO | TMPO | | | 1600-1700 | 1800-1900 |
| Human- | Intramolecula | TMSB4X | TMSB4X | | | 200-300 | 400-500 |
| Human- | Intramolecula | TMSB4X | TMSB4X | | | 200-300 | 500-600 |
| Human- | Intramolecula | TMSB4X | TMSB4X | | | 300-400 | 500-600 |
| Human- | Intramolecula | TOMM20 | TOMM20 | | | 400-500 | 500-600 |
| Human- | Intramolecula | TOMM7 | TOMM7 | | | 0-100 | 100-200 |
| Human- | Intramolecula | TPI1 | TPI1 | | | 1200-1300 | 1300-1400 |
| Human- | Intramolecula | TPT1 | TPT1 | | | 300-400 | 1000-1100 |
| Human- | Intramolecula | TPT1 | TPT1 | | | 400-500 | 1000-1100 |
| Human- | Intramolecula | TPT1 | TPT1 | | | 500-600 | 900-1000 |
| Human- | Intramolecula | TPT1 | TPT1 | | | 600-700 | 900-1000 |
| Human- | Intramolecula | TRAPPC5 | TRAPPC5 | | | 0-100 | 200-300 |
| Human- | Intramolecula | TRMT112 | TRMT112 | | | 800-900 | 900-1000 |
| Human- | Intramolecula | TSFM | TSFM | | | 500-600 | 600-700 |
| Human- | Intramolecula | UBA52 | UBA52 | | | 100-200 | 400-500 |
| Human- | Intramolecula | UBA52 | UBA52 | | | 200-300 | 400-500 |
| Human- | Intramolecula | UBB | UBB | | | 300-400 | 1100-1200 |
| Human- | Intramolecula | UBE2D3 | UBE2D3 | | | 1400-1500 | 1600-1700 |
| Human- | Intramolecula | UBL5 | UBL5 | | | 0-100 | 100-200 |
| Human- | Intramolecula | UBXN1 | UBXN1 | | | 1000-1100 | 1200-1300 |
| Human- | Intramolecula | UFM1 | UFM1 | | | 300-400 | 1000-1100 |
| Human- | Intramolecula | USMG5 | USMG5 | | | 0-100 | 400-500 |
| Human- | Intramolecula | VDAC2 | VDAC2 | | | 400-500 | 600-700 |
| Human- | Intramolecula | VKORC1 | VKORC1 | | | 500-600 | 600-700 |
| Human- | Intramolecula | VPS11 | VPS11 | | | 200-300 | 400-500 |
| Human- | Intramolecula | YBX1 | YBX1 | | | 1300-1400 | 1400-1500 |
| Human- | Intramolecula | YBX1 | YBX1 | | | 300-400 | 1000-1100 |
| Human- | Intramolecula | YIF1B | YIF1B | | | 800-900 | 900-1000 |
| Human- | Intramolecula | YWHAQ | YWHAQ | | | 1000-1100 | 1800-1900 |
| Human- | Intramolecula | YWHAQ | YWHAQ | | | 1100-1200 | 1800-1900 |
| Human- | Intramolecula | ZFAND6 | ZFAND6 | | | 200-300 | 400-500 |
| Human- | Intramolecula | ZFAS1 | ZFAS1 | | | 700-800 | 800-900 |
| Human- | Intramolecula | ZFAS1 | ZFAS1 | | | 700-800 | 900-1000 |
| Human- | Intramolecula | ZNF207 | ZNF207 | | | 900-1000 | 1000-1100 |
| Human- | Intramolecula | ZNHIT1 | ZNHIT1 | | | 800-900 | 900-1000 |

TABLE 4

List of lymphoblastoid cells snoRNA target sites

| SnoRNA | Start position | End position | Target RNA | Start position | End position | Read count | Notes |
|---|---|---|---|---|---|---|---|
| ACA13 | 0 | 100 | human-4V6X-18S | 1100 | 1200 | 4.25 | |
| ACA22 | 0 | 100 | human-4V6X-28S | 0 | 100 | 2.25 | |
| ACA40 | 0 | 100 | human-4V6X-18S | 1100 | 1200 | 2.25 | |
| ACA40 | 0 | 100 | human-4V6X-28S | 4500 | 4600 | 3.5 | |
| ACA51 | 0 | 100 | human-4V6X-28S | 4600 | 4700 | 2.25 | |
| ACA6 | 0 | 100 | human-4V6X-18S | 0 | 100 | 4 | |
| HBI-43 | 0 | 100 | human-4V6X-18S | 0 | 100 | 2.5 | |

TABLE 4-continued

List of lymphoblastoid cells snoRNA target sites

| SnoRNA | Start position | End position | Target RNA | Start position | End position | Read count | Notes |
|---|---|---|---|---|---|---|---|
| HBI-43 | 0 | 100 | human-4V6X-28S | 3800 | 3900 | 2 | |
| HBII-55 | 0 | 100 | human-4V6X-18S | 1200 | 1300 | 2.25 | |
| hTR | 400 | 500 | human-4V6X-28S | 2200 | 2300 | 9 | |
| hTR | 200 | 300 | hsnrna-RNU1-1 | 0 | 100 | 5 | |
| mgU12-22/U4-8 | 200 | 300 | human-4V6X-28S | 2200 | 2300 | 2 | |
| SNORA1 | 0 | 100 | human-4V6X-18S | 0 | 100 | 25.25 | |
| SNORA1 | 0 | 100 | human-4V6X-18S | 1300 | 1400 | 6 | |
| SNORA1 | 0 | 100 | human-4V6X-28S | 4500 | 4600 | 2.5 | |
| SNORA10 | 0 | 100 | hsnrna-RNU1-1 | 0 | 100 | 2 | |
| SNORA21 | 0 | 100 | human-4V6X-28S | 4400 | 4500 | 2.75 | |
| SNORA28 | 0 | 100 | human-4V6X-5S | 0 | 100 | 4.25 | |
| SNORA32 | 0 | 100 | human-4V6X-5S | 0 | 100 | 15.25 | |
| SNORA32 | 0 | 100 | human-4V6X-5S | 0 | 100 | 4 | |
| SNORA33 | 100 | 200 | hsnrna-RNU6-1 | 0 | 100 | 3 | |
| SNORA44 | 0 | 100 | hsnrna-RNU1-1 | 0 | 100 | 2 | |
| SNORA45A | 0 | 100 | human-4V6X-18S | 0 | 100 | 2.25 | |
| SNORA45A | 0 | 100 | human-4V6X-18S | 400 | 500 | 2.25 | |
| SNORA45A | 0 | 100 | human-4V6X-18S | 800 | 900 | 2.25 | |
| SNORA45A | 0 | 100 | human-4V6X-18S | 1300 | 1400 | 6.5 | |
| SNORA45A | 100 | 200 | human-4V6X-18S | 1300 | 1400 | 2 | |
| SNORA45A | 100 | 200 | human-4V6X-18S | 1400 | 1500 | 2 | |
| SNORA45A | 0 | 100 | human-4V6X-18S | 1400 | 1500 | 2 | |
| SNORA45A | 0 | 100 | human-4V6X-28S | 2400 | 2500 | 2.25 | |
| SNORA45A | 0 | 100 | human-4V6X-28S | 3800 | 3900 | 2.5 | |
| SNORA45B | 0 | 100 | human-4V6X-18S | 1300 | 1400 | 4.75 | |
| SNORA58 | 0 | 100 | human-4V6X-28S | 3000 | 3100 | 3 | |
| SNORA63 | 0 | 100 | human-4V6X-28S | 4300 | 4400 | 3.5 | |
| SNORA63 | 0 | 100 | human-4V6X-28S | 4500 | 4600 | 2 | |
| SNORA81 | 100 | 200 | hsnrna-RNU2-1 | 0 | 100 | 2 | |
| SNORD104 | 0 | 100 | human-4V6X-28S | 1300 | 1400 | 3 | |
| SNORD111B | 0 | 100 | human-4V6X-28S | 3900 | 4000 | 3 | |
| SNORD119 | 0 | 100 | human-4V6X-18S | 0 | 100 | 2.5 | |
| SNORD11B | 0 | 100 | hsnrna-RNU2-1 | 0 | 100 | 3 | |
| SNORD124 | 0 | 100 | hsnrna-RNU4ATAC | 0 | 100 | 2 | |
| SNORD12B | 0 | 100 | human-4V6X-28S | 2900 | 3000 | 2 | |
| SNORD15A | 100 | 200 | human-4V6X-28S | 4600 | 4700 | 5.25 | |
| SNORD15A | 100 | 200 | human-4V6X-28S | 4700 | 4800 | 5 | |
| SNORD15B | 0 | 100 | human-4V6X-18S | 900 | 1000 | 2 | |
| SNORD20 | 0 | 100 | human-4V6X-18S | 1700 | 1800 | 2 | |
| SNORD21 | 0 | 100 | human-4V6X-18S | 1500 | 1600 | 2 | |
| SNORD21 | 0 | 100 | hsnrna-RNU1-1 | 100 | 200 | 3 | |
| SNORD24 | 0 | 100 | human-4V6X-28S | 2300 | 2400 | 2.25 | |
| SNORD24 | 0 | 100 | human-4V6X-28S | 2300 | 2400 | 4 | |
| SNORD25 | 0 | 100 | human-4V6X-18S | 1400 | 1500 | 2.75 | |
| SNORD25 | 0 | 100 | human-4V6X-18S | 1500 | 1600 | 2.75 | |
| SNORD26 | 0 | 100 | human-4V6X-28S | 400 | 500 | 5.75 | |
| SNORD26 | 0 | 100 | human-4V6X-28S | 400 | 500 | 5 | |
| SNORD26 | 0 | 100 | human-4V6X-28S | 300 | 400 | 2 | |
| SNORD26 | 0 | 100 | human-4V6X-28S | 400 | 500 | 3 | |
| SNORD27 | 0 | 100 | human-4V6X-18S | 0 | 100 | 13 | |
| SNORD27 | 0 | 100 | human-4V6X-18S | 0 | 100 | 7 | |
| SNORD28 | 0 | 100 | human-4V6X-18S | 1300 | 1400 | 3.75 | |
| SNORD28 | 0 | 100 | human-4V6X-18S | 1400 | 1500 | 2 | |
| SNORD32A | 0 | 100 | human-4V6X-28S | 1500 | 1600 | 4 | |
| SNORD32A | 0 | 100 | human-4V6X-28S | 1500 | 1600 | 15 | |
| SNORD45A | 0 | 100 | human-4V6X-18S | 100 | 200 | 16.75 | |
| SNORD45A | 0 | 100 | human-4V6X-18S | 100 | 200 | 7 | |
| SNORD45A | 0 | 100 | human-4V6X-18S | 100 | 200 | 2 | |
| SNORD49A | 0 | 100 | human-4V6X-28S | 4400 | 4500 | 5 | |
| SNORD50A | 0 | 100 | human-4V6X-28S | 2800 | 2900 | 2 | |
| SNORD68 | 0 | 100 | human-4V6X-28S | 2300 | 2400 | 2 | |
| SNORD68 | 0 | 100 | human-4V6X-28S | 2700 | 2800 | 2 | |
| SNORD76 | 0 | 100 | human-4V6X-18S | 0 | 100 | 5.75 | |
| SNORD76 | 0 | 100 | human-4V6X-28S | 2300 | 2400 | 4.75 | |
| SNORD83A | 0 | 100 | human-4V6X-18S | 500 | 600 | 2 | |
| SNORD83A | 0 | 100 | U16 | 0 | 100 | 2 | |
| SNORD87 | 0 | 100 | human-4V6X-28S | 3700 | 3800 | 2.25 | |
| SNORD87 | 0 | 100 | human-4V6X-28S | 3700 | 3800 | 3 | |
| SNORD87 | 0 | 100 | human-4V6X-28S | 3700 | 3800 | 2 | |
| SNORD91A | 0 | 100 | human-4V6X-28S | 4600 | 4700 | 2 | |
| SNORD91B | 0 | 100 | human-4V6X-28S | 4600 | 4700 | 2.75 | |
| SNORD91B | 0 | 100 | human-4V6X-28S | 1500 | 1600 | 2 | |
| SNORD91B | 0 | 100 | human-4V6X-28S | 4600 | 4700 | 2 | |
| SNORD99 | 0 | 100 | human-4V6X-28S | 2700 | 2800 | 2 | |
| SNORD99 | 0 | 100 | human-4V6X-28S | 2800 | 2900 | 2 | |

TABLE 4-continued

List of lymphoblastoid cells snoRNA target sites

| SnoRNA | Start position | End position | Target RNA | Start position | End position | Read count | Notes |
|---|---|---|---|---|---|---|---|
| snR38C | 0 | 100 | human-4V6X-28S | 5000 | 5100 | 2 | |
| U13 | 0 | 100 | human-4V6X-18S | 0 | 100 | 2 | |
| U13 | 0 | 100 | human-4V6X-18S | 1700 | 1800 | 9 | |
| U13 | 0 | 100 | human-4V6X-18S | 1800 | 1900 | 13 | |
| U13 | 0 | 100 | human-4V6X-28S | 4400 | 4500 | 12 | |
| U13 | 0 | 100 | human-4V6X-28S | 4500 | 4600 | 5.25 | |
| U13 | 0 | 100 | human-4V6X-18S | 0 | 100 | 11 | |
| U13 | 0 | 100 | human-4V6X-18S | 100 | 200 | 9 | |
| U13 | 0 | 100 | human-4V6X-18S | 400 | 500 | 9 | |
| U13 | 0 | 100 | human-4V6X-18S | 600 | 700 | 2 | |
| U13 | 0 | 100 | human-4V6X-18S | 700 | 800 | 4 | |
| U13 | 0 | 100 | human-4V6X-18S | 900 | 1000 | 7 | |
| U13 | 0 | 100 | human-4V6X-18S | 1100 | 1200 | 12 | |
| U13 | 0 | 100 | human-4V6X-18S | 1200 | 1300 | 5 | |
| U13 | 0 | 100 | human-4V6X-18S | 1300 | 1400 | 6 | |
| U13 | 0 | 100 | human-4V6X-18S | 1400 | 1500 | 2 | |
| U13 | 0 | 100 | human-4V6X-18S | 1500 | 1600 | 5 | |
| U13 | 0 | 100 | human-4V6X-18S | 1600 | 1700 | 2 | |
| U13 | 0 | 100 | human-4V6X-18S | 1700 | 1800 | 9 | |
| U13 | 0 | 100 | human-4V6X-18S | 1800 | 1900 | 16 | |
| U13 | 0 | 100 | human-4V6X-28S | 0 | 100 | 7 | |
| U13 | 0 | 100 | human-4V6X-28S | 100 | 200 | 2 | |
| U13 | 0 | 100 | human-4V6X-28S | 300 | 400 | 4 | |
| U13 | 0 | 100 | human-4V6X-28S | 400 | 500 | 14 | |
| U13 | 0 | 100 | human-4V6X-28S | 1300 | 1400 | 2 | |
| U13 | 0 | 100 | human-4V6X-28S | 1600 | 1700 | 4 | |
| U13 | 0 | 100 | human-4V6X-28S | 1900 | 2000 | 2 | |
| U13 | 0 | 100 | human-4V6X-28S | 2400 | 2500 | 3 | |
| U13 | 0 | 100 | human-4V6X-28S | 2700 | 2800 | 3 | |
| U13 | 0 | 100 | human-4V6X-28S | 2800 | 2900 | 8 | |
| U13 | 0 | 100 | human-4V6X-28S | 2900 | 3000 | 2 | |
| U13 | 0 | 100 | human-4V6X-28S | 3600 | 3700 | 2 | |
| U13 | 0 | 100 | human-4V6X-28S | 3700 | 3800 | 3 | |
| U13 | 0 | 100 | human-4V6X-28S | 3800 | 3900 | 3 | |
| U13 | 0 | 100 | human-4V6X-28S | 4400 | 4500 | 76 | |
| U13 | 0 | 100 | human-4V6X-28S | 4500 | 4600 | 10 | |
| U13 | 0 | 100 | human-4V6X-5.8S | 0 | 100 | 3 | |
| U13 | 0 | 100 | U19-2 | 0 | 100 | 2 | |
| U13 | 0 | 100 | hsnrna-RNU1-1 | 0 | 100 | 88 | |
| U13 | 0 | 100 | hsnrna-RNU1-1 | 100 | 200 | 17 | |
| U13 | 0 | 100 | hsnrna-RNU12 | 100 | 200 | 2 | |
| U13 | 0 | 100 | hsnrna-RNU2-1 | 0 | 100 | 5 | |
| U13 | 0 | 100 | hsnrna-RNU2-1 | 100 | 200 | 4 | |
| U13 | 0 | 100 | hsnrna-RNU4-1 | 0 | 100 | 21 | |
| U13 | 0 | 100 | hsnrna-RNU6-1 | 0 | 100 | 2 | |
| U14A | 0 | 100 | human-4V6X-18S | 0 | 100 | 12.25 | |
| U14A | 0 | 100 | human-4V6X-18S | 100 | 200 | 3.75 | |
| U14A | 0 | 100 | human-4V6X-18S | 400 | 500 | 8.25 | |
| U14A | 0 | 100 | human-4V6X-18S | 0 | 100 | 7 | |
| U14A | 0 | 100 | human-4V6X-18S | 400 | 500 | 5 | |
| U14A | 0 | 100 | human-4V6X-18S | 500 | 600 | 2 | |
| U14B | 0 | 100 | human-4V6X-18S | 400 | 500 | 4 | |
| U14B | 0 | 100 | human-4V6X-18S | 1300 | 1400 | 3.75 | |
| U14B | 0 | 100 | human-4V6X-28S | 4400 | 4500 | 2.25 | |
| U14B | 0 | 100 | human-4V6X-18S | 400 | 500 | 2 | |
| U16 | 0 | 100 | human-4V6X-18S | 500 | 600 | 2 | |
| U16 | 0 | 100 | human-4V6X-18S | 400 | 500 | 2 | |
| U17a | 0 | 100 | human-4V6X-18S | 100 | 200 | 2.25 | |
| U17a | 100 | 200 | human-4V6X-18S | 500 | 600 | 4.5 | Homolog, snR30, found in yeast by SPLASH |
| U17a | 100 | 200 | human-4V6X-18S | 1500 | 1600 | 2.25 | |
| U17a | 100 | 200 | human-4V6X-28S | 2800 | 2900 | 2.5 | |
| U17a | 100 | 200 | human-4V6X-28S | 4600 | 4700 | 3 | Homolog, snR30, found in yeast by SPLASH |
| U17b | 100 | 200 | human-4V6X-18S | 400 | 500 | 2.5 | Homolog, snR30, found in yeast by SPLASH |
| U17b | 100 | 200 | human-4V6X-18S | 500 | 600 | 4.5 | Homolog, snR30, found in yeast by SPLASH |

TABLE 4-continued

List of lymphoblastoid cells snoRNA target sites

| SnoRNA | Start position | End position | Target RNA | Start position | End position | Read count | Notes |
|---|---|---|---|---|---|---|---|
| U17b | 0 | 100 | human-4V6X-18S | 900 | 1000 | 2.5 | |
| U17b | 100 | 200 | human-4V6X-28S | 2300 | 2400 | 2.5 | |
| U17b | 100 | 200 | human-4V6X-28S | 4600 | 4700 | 3 | Homolog, snR30, found in yeast by SPLASH |
| U17b | 100 | 200 | hsnrna-RNU1-1 | 0 | 100 | 2 | |
| U19-2 | 0 | 100 | hsnrna-RNU1-1 | 0 | 100 | 2 | |
| U3 | 0 | 100 | human-4V6X-18S | 100 | 200 | 12 | |
| U3 | 0 | 100 | human-4V6X-18S | 1300 | 1400 | 6 | |
| U3 | 0 | 100 | human-4V6X-28S | 3700 | 3800 | 3 | |
| U3 | 0 | 100 | HSU13369-5ETS | 400 | 500 | 2 | |
| U3 | 0 | 100 | hsnrna-RNU1-1 | 0 | 100 | 15 | |
| U3 | 0 | 100 | hsnrna-RNU1-1 | 100 | 200 | 5 | |
| U31 | 0 | 100 | human-4V6X-28S | 2800 | 2900 | 2.25 | |
| U31 | 0 | 100 | human-4V6X-28S | 4100 | 4200 | 12.25 | |
| U31 | 0 | 100 | human-4V6X-28S | 4200 | 4300 | 17.5 | |
| U31 | 0 | 100 | human-4V6X-5.8S | 0 | 100 | 4 | |
| U31 | 0 | 100 | human-4V6X-5.8S | 100 | 200 | 4 | |
| U31 | 0 | 100 | human-4V6X-28S | 4200 | 4300 | 2 | |
| U3-2 | 0 | 100 | human-4V6X-18S | 1300 | 1400 | 8 | |
| U3-2 | 0 | 100 | human-4V6X-28S | 2800 | 2900 | 2 | |
| U3-2 | 0 | 100 | hsnrna-RNU1-1 | 0 | 100 | 3 | |
| U33 | 0 | 100 | human-4V6X-18S | 1300 | 1400 | 8.25 | |
| U33 | 0 | 100 | human-4V6X-18S | 1300 | 1400 | 10 | |
| U34 | 0 | 100 | human-4V6X-28S | 2800 | 2900 | 5.25 | |
| U35A | 0 | 100 | human-4V6X-28S | 4500 | 4600 | 3.25 | |
| U35A | 0 | 100 | human-4V6X-28S | 2700 | 2800 | 2 | |
| U35A | 0 | 100 | human-4V6X-28S | 4500 | 4600 | 3 | |
| U37 | 0 | 100 | human-4V6X-28S | 3700 | 3800 | 2.5 | |
| U42B | 0 | 100 | human-4V6X-18S | 100 | 200 | 3 | |
| U45B | 0 | 100 | human-4V6X-18S | 100 | 200 | 2 | |
| U45C | 0 | 100 | human-4V6X-18S | 100 | 200 | 7 | |
| U45C | 0 | 100 | human-4V6X-18S | 100 | 200 | 4 | |
| U45C | 0 | 100 | human-4V6X-18S | 100 | 200 | 2 | |
| U54 | 0 | 100 | human-4V6X-18S | 600 | 700 | 2 | |
| U55 | 0 | 100 | human-4V6X-18S | 400 | 500 | 2 | |
| U55 | 0 | 100 | human-4V6X-28S | 500 | 600 | 2 | |
| U55 | 0 | 100 | human-4V6X-28S | 1400 | 1500 | 2 | |
| U55 | 0 | 100 | human-4V6X-28S | 1700 | 1800 | 4 | |
| U55 | 0 | 100 | human-4V6X-28S | 4400 | 4500 | 4 | |
| U55 | 0 | 100 | HSU13369-5ETS | 2200 | 2300 | 2 | |
| U55 | 0 | 100 | human-4V6X-28S | 1400 | 1500 | 3 | |
| U55 | 0 | 100 | human-4V6X-28S | 1500 | 1600 | 3 | |
| U55 | 0 | 100 | hsnrna-RNU1-1 | 0 | 100 | 6 | |
| U57 | 0 | 100 | human-4V6X-18S | 0 | 100 | 4.5 | |
| U57 | 0 | 100 | human-4V6X-18S | 0 | 100 | 4 | |
| U57 | 0 | 100 | human-4V6X-18S | 100 | 200 | 4 | |
| U60 | 0 | 100 | human-4V6X-28S | 4300 | 4400 | 2 | |
| U60 | 0 | 100 | human-4V6X-28S | 4300 | 4400 | 3 | |
| U61 | 0 | 100 | human-4V6X-18S | 1400 | 1500 | 2 | |
| U64 | 0 | 100 | human-4V6X-28S | 1500 | 1600 | 2 | |
| U64 | 0 | 100 | human-4V6X-28S | 2400 | 2500 | 2.5 | |
| U74 | 0 | 100 | human-4V6X-28S | 3800 | 3900 | 2.75 | |
| U74 | 0 | 100 | human-4V6X-28S | 3800 | 3900 | 6 | |
| U74 | 0 | 100 | human-4V6X-28S | 3800 | 3900 | 3 | |
| U80 | 0 | 100 | human-4V6X-28S | 1600 | 1700 | 15.25 | |
| U80 | 0 | 100 | human-4V6X-28S | 1600 | 1700 | 13 | |
| U80 | 0 | 100 | human-4V6X-28S | 1600 | 1700 | 3 | |
| U81 | 0 | 100 | human-4V6X-28S | 300 | 400 | 5.5 | |
| U81 | 0 | 100 | human-4V6X-28S | 400 | 500 | 9 | |
| U81 | 0 | 100 | human-4V6X-28S | 300 | 400 | 7 | |
| U81 | 0 | 100 | human-4V6X-28S | 400 | 500 | 6 | |
| U83B | 0 | 100 | human-4V6X-18S | 400 | 500 | 3.25 | |
| U83B | 0 | 100 | human-4V6X-28S | 2800 | 2900 | 3 | |
| U94 | 0 | 100 | hsnrna-RNU1-1 | 100 | 200 | 2 | |
| U96a | 0 | 100 | human-4V6X-5.8S | 0 | 100 | 3 | |
| U99 | 0 | 100 | human-4V6X-18S | 700 | 800 | 3.25 | |

TABLE 5

List of yeast snoRNA target sites

| SnoRNA | Start position | End position | Target RNA | Start position | End position | Read count | Notes |
|---|---|---|---|---|---|---|---|
| snR11 | 0 | 100 | RDN25-2 | 2900 | 3000 | 2 | |
| snR128 | 0 | 100 | RDN18-1 | 0 | 100 | 95.5 | |
| snR128 | 0 | 100 | RDN18-1 | 100 | 200 | 33 | Known homolog, U14, found in human |
| snR128 | 0 | 100 | RDN25-2 | 1000 | 1100 | 2.5 | |
| snR17a | 200 | 300 | RDN18-1 | 400 | 500 | 2.5 | |
| snR17a | 200 | 300 | RDN18-1 | 500 | 600 | 4 | |
| snR17a | 100 | 200 | RDN18-1 | 1000 | 1100 | 2.5 | |
| snR17a | 100 | 200 | RDN25-2 | 1200 | 1300 | 7 | |
| snR17a | 200 | 300 | RDN25-2 | 2800 | 2900 | 2.5 | |
| snR17a | 300 | 400 | RDN25-2 | 2900 | 3000 | 4.5 | |
| snR18 | 0 | 100 | RDN18-1 | 800 | 900 | 2 | |
| snR18 | 0 | 100 | RDN18-1 | 1000 | 1100 | 5.5 | |
| snR18 | 0 | 100 | RDN25-2 | 600 | 700 | 8.5 | |
| snR189 | 100 | 200 | RDN25-2 | 1700 | 1800 | 23.5 | |
| snR189 | 100 | 200 | RDN25-2 | 2800 | 2900 | 3 | |
| snR24 | 0 | 100 | RDN18-1 | 500 | 600 | 4 | |
| snR24 | 0 | 100 | RDN25-2 | 1300 | 1400 | 4 | |
| snR24 | 0 | 100 | RDN25-2 | 1400 | 1500 | 575 | |
| snR24 | 0 | 100 | RDN25-2 | 3000 | 3100 | 2 | |
| snR30 | 500 | 600 | RDN18-1 | 400 | 500 | 2.5 | Homolog, U17, found in human by SPLASH |
| snR30 | 300 | 400 | RDN18-1 | 700 | 800 | 5 | |
| snR30 | 400 | 500 | RDN18-1 | 1000 | 1100 | 7.5 | |
| snR30 | 500 | 600 | RDN25-2 | 1100 | 1200 | 3 | |
| snR30 | 400 | 500 | RDN25-2 | 2900 | 3000 | 3 | Homolog, U17, found in human by SPLASH |
| snR30 | 0 | 100 | RDN25-2 | 3000 | 3100 | 2.5 | Homolog, U17, found in human by SPLASH |
| snR31 | 0 | 100 | RDN25-2 | 1100 | 1200 | 4.5 | |
| snR32 | 0 | 100 | RDN25-2 | 1500 | 1600 | 2.5 | |
| snR32 | 0 | 100 | RDN25-2 | 2900 | 3000 | 3 | |
| snR34 | 0 | 100 | RDN18-1 | 800 | 900 | 2.5 | |
| snR34 | 100 | 200 | RDN25-2 | 2800 | 2900 | 6.5 | |
| snR36 | 0 | 100 | RDN18-1 | 400 | 500 | 3.5 | |
| snR37 | 0 | 100 | RDN25-2 | 2900 | 3000 | 28 | |
| snR37 | 0 | 100 | RDN25-2 | 3000 | 3100 | 4.5 | |
| snR38 | 0 | 100 | RDN18-1 | 800 | 900 | 2 | |
| snR38 | 0 | 100 | RDN25-2 | 1300 | 1400 | 2.5 | |
| snR38 | 0 | 100 | RDN25-2 | 2700 | 2800 | 8 | |
| snR38 | 0 | 100 | RDN25-2 | 2800 | 2900 | 48 | |
| snR38 | 0 | 100 | RDN25-2 | 2900 | 3000 | 3 | |
| snR39 | 0 | 100 | RDN25-2 | 900 | 1000 | 3.5 | Known homolog, SNORD32A, found in human |
| snR39B | 0 | 100 | RDN18-1 | 500 | 600 | 2.5 | |
| snR39B | 0 | 100 | RDN25-2 | 1200 | 1300 | 2.5 | |
| snR39B | 0 | 100 | RDN25-2 | 1300 | 1400 | 3.5 | |
| snR39B | 0 | 100 | RDN25-2 | 1700 | 1800 | 10 | |
| snR4 | 100 | 200 | RDN18-1 | 400 | 500 | 6.5 | |
| snR4 | 0 | 100 | RDN25-2 | 1000 | 1100 | 4.5 | |
| snR4 | 0 | 100 | RDN25-2 | 1600 | 1700 | 2.5 | |
| snR4 | 0 | 100 | RDN25-2 | 1800 | 1900 | 3.5 | |
| snR40 | 0 | 100 | RDN18-1 | 500 | 600 | 15.5 | |
| snR40 | 0 | 100 | RDN18-1 | 700 | 800 | 4 | |
| snR40 | 0 | 100 | RDN18-1 | 800 | 900 | 2 | |
| snR40 | 0 | 100 | RDN18-1 | 1200 | 1300 | 19 | |
| snR40 | 0 | 100 | RDN25-2 | 900 | 1000 | 10 | |
| snR40 | 0 | 100 | RDN25-2 | 2800 | 2900 | 4 | |
| snR40 | 0 | 100 | RDN25-2 | 3100 | 3200 | 2.5 | |
| snR40 | 0 | 100 | RDN25-2 | 3200 | 3300 | 11 | |
| snR41 | 0 | 100 | RDN18-1 | 500 | 600 | 15 | |
| snR41 | 0 | 100 | RDN18-1 | 1100 | 1200 | 65.5 | |
| snR41 | 0 | 100 | RDN25-2 | 1800 | 1900 | 2 | |
| snR45 | 100 | 200 | RDN25-2 | 3100 | 3200 | 5.5 | |
| snR47 | 0 | 100 | RDN18-1 | 600 | 700 | 9 | |
| snR47 | 0 | 100 | RDN18-1 | 800 | 900 | 2.5 | |
| snR48 | 0 | 100 | RDN25-2 | 2700 | 2800 | 70 | |
| snR48 | 0 | 100 | RDN25-2 | 2800 | 2900 | 101 | |
| snR52 | 0 | 100 | RDN18-1 | 300 | 400 | 9 | |
| snR52 | 0 | 100 | RDN18-1 | 400 | 500 | 323.5 | |

TABLE 5-continued

List of yeast snoRNA target sites

| SnoRNA | Start position | End position | Target RNA | Start position | End position | Read count | Notes |
|---|---|---|---|---|---|---|---|
| snR52 | 0 | 100 | RDN18-1 | 500 | 600 | 2.5 | |
| snR52 | 0 | 100 | RDN18-1 | 800 | 900 | 4.5 | |
| snR52 | 0 | 100 | RDN25-2 | 1800 | 1900 | 5.5 | |
| snR52 | 0 | 100 | RDN25-2 | 2800 | 2900 | 5.5 | |
| snR52 | 0 | 100 | RDN25-2 | 2900 | 3000 | 6.5 | |
| snR53 | 0 | 100 | RDN18-1 | 700 | 800 | 4 | |
| snR54 | 0 | 100 | RDN18-1 | 900 | 1000 | 6 | |
| snR55 | 0 | 100 | RDN18-1 | 1200 | 1300 | 199 | |
| snR55 | 0 | 100 | RDN18-1 | 1300 | 1400 | 2 | |
| snR59 | 0 | 100 | RDN25-2 | 1800 | 1900 | 14.5 | |
| snR60 | 0 | 100 | RDN25-2 | 900 | 1000 | 57.5 | |
| snR61 | 0 | 100 | Q0158 | 800 | 900 | 2.5 | |
| snR61 | 0 | 100 | RDN25-2 | 1100 | 1200 | 13.5 | |
| snR61 | 0 | 100 | RDN25-2 | 1600 | 1700 | 4.5 | |
| snR61 | 0 | 100 | RDN25-2 | 2800 | 2900 | 5 | |
| snR61 | 0 | 100 | RDN25-2 | 2900 | 3000 | 2 | |
| snR62 | 0 | 100 | RDN25-2 | 1800 | 1900 | 19.5 | |
| snR62 | 0 | 100 | RDN25-2 | 1900 | 2000 | 7 | |
| snR69 | 0 | 100 | RDN25-2 | 2900 | 3000 | 36.5 | |
| snR69 | 0 | 100 | RDN25-2 | 3200 | 3300 | 2 | |
| snR71 | 0 | 100 | RDN25-2 | 1600 | 1700 | 4 | |
| snR71 | 0 | 100 | RDN25-2 | 2900 | 3000 | 16.5 | |
| snR74 | 0 | 100 | RDN18-1 | 0 | 100 | 11 | |
| snR75 | 0 | 100 | Q0158 | 3200 | 3300 | 3.5 | |
| snR75 | 0 | 100 | RDN18-1 | 400 | 500 | 2.5 | |
| snR75 | 0 | 100 | RDN18-1 | 500 | 600 | 3 | |
| snR77 | 0 | 100 | RDN18-1 | 500 | 600 | 86 | |
| snR77 | 0 | 100 | RDN18-1 | 600 | 700 | 5.5 | |
| snR77 | 0 | 100 | RDN25-2 | 900 | 1000 | 15 | |
| snR77 | 0 | 100 | RDN25-2 | 1300 | 1400 | 8 | |
| snR79 | 0 | 100 | RDN18-1 | 900 | 1000 | 103.5 | |
| snR79 | 0 | 100 | RDN18-1 | 1000 | 1100 | 367.5 | |
| snR80 | 0 | 100 | RDN18-1 | 500 | 600 | 2.5 | |
| snR80 | 0 | 100 | RDN25-2 | 2900 | 3000 | 2.5 | |
| snR80 | 0 | 100 | RDN25-2 | 3000 | 3100 | 7.5 | |
| snR81 | 100 | 200 | RDN25-2 | 1900 | 2000 | 2 | |
| snR81 | 0 | 100 | RDN25-2 | 2900 | 3000 | 4.5 | |
| snR83 | 0 | 100 | RDN18-1 | 1200 | 1300 | 4 | |
| snR86 | 600 | 700 | RDN18-1 | 400 | 500 | 9 | |
| snR86 | 600 | 700 | RDN18-1 | 500 | 600 | 2.5 | |
| Y-NME1 | 200 | 300 | RDN25-2 | 1500 | 1600 | 3.5 | |

TABLE 6

Go term analysis of network interactions in lymphblastoid, ES and RA cells

| Cell type | ModID | GO.ID | Term | Annotated | Significant | Expected | P-value | GOType | EnrichFold |
|---|---|---|---|---|---|---|---|---|---|
| Lymphoblastoid | central cluster | 00:0006414 | translational elongation | 69 | 69 | 62.15 | 5.50E−05 | BP | 1.11 |
| Lymphoblastoid | central cluster | 00:0006413 | translational initiation | 66 | 66 | 59.44 | 1.00E−04 | BP | 1.11 |
| Lymphoblastoid | central cluster | 00:0006415 | translational termination | 66 | 66 | 59.44 | 1.00E−04 | BP | 1.11 |
| Lymphoblastoid | central cluster | 00:0006614 | SRP-dependent cotranslational protein targeting to membrane | 66 | 66 | 59.44 | 1.00E−04 | BP | 1.11 |
| Lymphoblastoid | central cluster | 00:0000184 | nuclear-transcribed mRNA catabolic process, nonsense-mediated decay | 65 | 65 | 58.54 | 0.00012 | BP | 1.11 |
| Lymphoblastoid | central cluster | 00:0032991 | macromolecular complex | 107 | 106 | 95.49 | 0.00032 | CC | 1.11 |
| Lymphoblastoid | central cluster | 00:0070062 | extracellular vesicular exosome | 91 | 88 | 81.21 | 0.00049 | CC | 1.08 |
| Lymphoblastoid | central cluster | 00:0016020 | membrane | 102 | 97 | 91.03 | 0.00203 | CC | 1.07 |
| Lymphoblastoid | central cluster | 00:0005829 | cytosol | 99 | 96 | 88.35 | 0.00404 | CC | 1.09 |
| Lymphoblastoid | central cluster | 00:0022625 | cytosolic large ribosomal subunit | 41 | 41 | 36.59 | 0.00436 | CC | 1.12 |
| Lymphoblastoid | central cluster | 00:0003735 | structural constituent of ribosome | 66 | 66 | 58.13 | 1.30E−05 | MF | 1.14 |

TABLE 6-continued

Go term analysis of network interactions in lymphblastoid, ES and RA cells

| Cell type | ModID | GO.ID | Term | Annotated | Significant | Expected | P-value | GOType | EnrichFold |
|---|---|---|---|---|---|---|---|---|---|
| Lymphoblastoid | central cluster | 00:0044822 | poly(A) RNA binding | 79 | 76 | 69.58 | 0.0012 | MF | 1.09 |
| Lymphoblastoid | central cluster | 00:0005515 | protein binding | 102 | 93 | 89.84 | 0.0794 | MF | 1.04 |
| Lymphoblastoid | central cluster | 00:0003723 | RNA binding | 89 | 86 | 78.39 | 0.0805 | MF | 1.10 |
| Lymphoblastoid | central cluster | 00:0033218 | amide binding | 14 | 14 | 12.33 | 0.155 | MF | 1.14 |
| Lymphoblastoid | 1 | 00:0019843 | rRNA binding | 9 | 5 | 1.49 | 0.0067 | MF | 3.36 |
| Lymphoblastoid | 1 | 00:0030168 | platelet activation | 8 | 4 | 1.38 | 0.03 | BP | 2.90 |
| Lymphoblastoid | 1 | 00:0002576 | platelet degranulation | 5 | 3 | 0.86 | 0.036 | BP | 3.49 |
| Lymphoblastoid | 1 | 00:0006887 | exocytosis | 5 | 3 | 0.86 | 0.036 | BP | 3.49 |
| Lymphoblastoid | 1 | 00:0016020 | membrane | 102 | 21 | 16.78 | 0.044 | CC | 1.25 |
| Lymphoblastoid | 2 | 00:1901575 | organic substance catabolic process | 89 | 17 | 12.38 | 0.022 | BP | 1.37 |
| Lymphoblastoid | 2 | 00:0009056 | catabolic process | 90 | 17 | 12.52 | 0.025 | BP | 1.36 |
| Lymphoblastoid | 2 | 00:0016052 | carbohydrate catabolic process | 10 | 4 | 1.39 | 0.034 | BP | 2.88 |
| Lymphoblastoid | 2 | 00:0044724 | single-organism carbohydrate catabolic process | 10 | 4 | 1.39 | 0.034 | BP | 2.88 |
| Lymphoblastoid | 2 | 00:0097285 | cell-type specific apoptotic process | 6 | 3 | 0.83 | 0.036 | BP | 3.61 |
| Lymphoblastoid | 3 | 00:0006614 | SRP-dependent cotranslational protein targeting to membrane | 66 | 23 | 13.11 | 5.10E−05 | BP | 1.75 |
| Lymphoblastoid | 3 | 00:0003735 | structural constituent of ribosome | 66 | 23 | 13.11 | 5.10E−05 | MF | 1.75 |
| Lymphoblastoid | 3 | 00:0006414 | translational elongation | 69 | 23 | 13.71 | 0.00014 | BP | 1.68 |
| Lymphoblastoid | 3 | 00:0000184 | nuclear-transcribed mRNA catabolic process, nonsense-mediated decay | 65 | 22 | 12.91 | 2.00E−04 | BP | 1.70 |
| Lymphoblastoid | 3 | 00:0019083 | viral transcription | 65 | 22 | 12.91 | 2.00E−04 | BP | 1.70 |
| Lymphoblastoid | 3 | 00:0006413 | translational initiation | 66 | 22 | 13.11 | 0.00027 | BP | 1.68 |
| Lymphoblastoid | 3 | 00:0022626 | cytosolic ribosome | 65 | 22 | 12.34 | 0.0031 | CC | 1.78 |
| Lymphoblastoid | 3 | 00:0044391 | ribosomal subunit | 66 | 22 | 12.53 | 0.004 | CC | 1.76 |
| Lymphoblastoid | 3 | 00:0022627 | cytosolic small ribosomal subunit | 24 | 10 | 4.56 | 0.0044 | CC | 2.19 |
| Lymphoblastoid | 3 | 00:0003723 | RNA binding | 89 | 24 | 17.68 | 0.0066 | MF | 1.36 |
| Lymphoblastoid | 3 | 00:0043232 | intracellular non-membrane-bounded organelle | 95 | 28 | 18.04 | 0.0111 | CC | 1.55 |
| Lymphoblastoid | 3 | 00:0043228 | non-membrane-bounded organelle | 95 | 28 | 18.04 | 0.0111 | CC | 1.55 |
| Lymphoblastoid | 4 | 00:0042605 | peptide antigen binding | 9 | 8 | 0.6 | 7.20E−11 | MF | 13.33 |
| Lymphoblastoid | 4 | 00:0071556 | integral component of lumenal side of endoplasmic reticulum membrane | 10 | 8 | 0.63 | 2.50E−10 | CC | 12.70 |
| Lymphoblastoid | 4 | 00:0012507 | ER to Golgi transport vesicle membrane | 11 | 8 | 0.7 | 8.90E−10 | CC | 11.43 |
| Lymphoblastoid | 4 | 00:0000139 | Golgi membrane | 12 | 8 | 0.76 | 2.60E−09 | CC | 10.53 |
| Lymphoblastoid | 4 | 00:0060333 | interferon-gamma-mediated signaling pathway | 12 | 8 | 0.79 | 3.80E−09 | BP | 10.13 |
| Lymphoblastoid | 4 | 00:0016045 | detection of bacterium | 5 | 5 | 0.33 | 4.10E−07 | BP | 15.15 |
| Lymphoblastoid | 4 | 00:0031901 | early endosome membrane | 6 | 5 | 0.38 | 1.90E−06 | CC | 13.16 |
| Lymphoblastoid | 4 | 00:0042612 | MHC class I protein complex | 6 | 5 | 0.38 | 1.90E−06 | CC | 13.16 |
| Lymphoblastoid | 4 | 00:0001916 | positive regulation of T cell mediated cytotoxicity | 6 | 5 | 0.4 | 2.40E−06 | BP | 12.50 |

TABLE 6-continued

Go term analysis of network interactions in lymphblastoid, ES and RA cells

| Cell type | ModID | GO.ID | Term | Annotated | Significant | Expected | P-value | GOType | EnrichFold |
|---|---|---|---|---|---|---|---|---|---|
| Lymphoblastoid | 4 | 00:0002480 | antigen processing and presentation of exogenous peptide antigen via MHC class I, TAP-independent | 6 | 5 | 0.4 | 2.40E−06 | BP | 12.50 |
| Lymphoblastoid | 4 | 00:0002479 | antigen processing and presentation of exogenous peptide antigen via MHC class I, TAP-dependent | 7 | 5 | 0.46 | 8.20E−06 | BP | 10.87 |
| Lymphoblastoid | 4 | 00:0005102 | receptor binding | 9 | 4 | 0.6 | 0.0011 | MF | 6.67 |
| Lymphoblastoid | 4 | 00:0004872 | receptor activity | 5 | 2 | 0.33 | 0.0356 | MF | 6.06 |
| Lymphoblastoid | 5 | 00:0044429 | mitochondrial part | 9 | 3 | 0.51 | 0.0092 | CC | 5.88 |
| Lymphoblastoid | 5 | 00:0031975 | envelope | 10 | 3 | 0.57 | 0.0127 | CC | 5.26 |
| Lymphoblastoid | 5 | 00:0031967 | organelle envelope | 10 | 3 | 0.57 | 0.0127 | CC | 5.26 |
| Lymphoblastoid | 5 | 00:0097193 | intrinsic apoptotic signaling pathway | 10 | 3 | 0.6 | 0.014 | BP | 5.00 |
| Lymphoblastoid | 5 | 00:0010035 | response to inorganic substance | 5 | 2 | 0.3 | 0.029 | BP | 6.67 |
| Lymphoblastoid | 5 | 00:0009991 | response to extracellular stimulus | 5 | 2 | 0.3 | 0.029 | BP | 6.67 |
| Lymphoblastoid | 5 | 00:0061061 | muscle structure development | 5 | 2 | 0.3 | 0.029 | BP | 6.67 |
| Lymphoblastoid | 5 | 00:0016491 | oxidoreductase activity | 5 | 2 | 0.3 | 0.029 | MF | 6.67 |
| Lymphoblastoid | 5 | 00:0097190 | apoptotic signaling pathway | 14 | 3 | 0.83 | 0.038 | BP | 3.61 |
| Lymphoblastoid | 5 | 00:0031966 | mitochondrial membrane | 6 | 2 | 0.34 | 0.0386 | CC | 5.88 |
| Lymphoblastoid | 5 | 00:0019866 | organelle inner membrane | 6 | 2 | 0.34 | 0.0386 | CC | 5.88 |
| Lymphoblastoid | 5 | 00:0022857 | transmembrane transporter activity | 6 | 2 | 0.36 | 0.042 | MF | 5.56 |
| Lymphoblastoid | 5 | 00:0015075 | ion transmembrane transporter activity | 6 | 2 | 0.36 | 0.042 | MF | 5.56 |
| Lymphoblastoid | 5 | 00:0022891 | substrate-specific transmembrane transporter activity | 6 | 2 | 0.36 | 0.042 | MF | 5.56 |
| Lymphoblastoid | 6 | 00:0010628 | positive regulation of gene expression | 5 | 4 | 0.53 | 0.00041 | BP | 7.55 |
| Lymphoblastoid | 6 | 00:2001233 | regulation of apoptotic signaling pathway | 12 | 5 | 1.27 | 0.00357 | BP | 3.94 |
| Lymphoblastoid | 6 | 00:0045892 | negative regulation of transcription, DNA-templated | 8 | 4 | 0.85 | 0.00467 | BP | 4.71 |
| Lymphoblastoid | 6 | 00:0051347 | positive regulation of transferase activity | 5 | 3 | 0.53 | 0.00869 | BP | 5.66 |
| Lymphoblastoid | 6 | 00:0043410 | positive regulation of MAPK cascade | 5 | 3 | 0.53 | 0.00869 | BP | 5.66 |
| Lymphoblastoid | 7 | 00:0044430 | cytoskeletal part | 12 | 4 | 1.22 | 0.021 | CC | 3.28 |
| Lymphoblastoid | 7 | 00:0015630 | microtubule cytoskeleton | 7 | 3 | 0.71 | 0.023 | CC | 4.23 |
| Lymphoblastoid | 7 | 00:0044428 | nuclear part | 41 | 8 | 4.15 | 0.026 | CC | 1.93 |
| Lymphoblastoid | 8 | 00:0006812 | cation transport | 6 | 2 | 0.2 | 0.013 | BP | 10.00 |
| Lymphoblastoid | 8 | 00:0050801 | ion homeostasis | 6 | 2 | 0.2 | 0.013 | BP | 10.00 |
| Lymphoblastoid | 8 | 00:0055082 | cellular chemical homeostasis | 7 | 2 | 0.23 | 0.017 | BP | 8.70 |
| Lymphoblastoid | 8 | 00:0046872 | metal ion binding | 21 | 3 | 0.7 | 0.02 | MF | 4.29 |
| Lymphoblastoid | 8 | 00:0043169 | cation binding | 21 | 3 | 0.7 | 0.02 | MF | 4.29 |
| Lymphoblastoid | 8 | 00:0005887 | integral component of plasma membrane | 8 | 2 | 0.3 | 0.031 | CC | 6.67 |
| Lymphoblastoid | 8 | 00:0031226 | intrinsic component of plasma membrane | 8 | 2 | 0.3 | 0.031 | CC | 6.67 |
| Lymphoblastoid | 8 | 00:0019725 | cellular homeostasis | 10 | 2 | 0.33 | 0.036 | BP | 6.06 |
| Lymphoblastoid | 8 | 00:0048878 | chemical homeostasis | 10 | 2 | 0.33 | 0.036 | BP | 6.06 |
| Lymphoblastoid | 9 | 00:0044085 | cellular component biogenesis | 41 | 4 | 1.36 | 0.019 | BP | 2.94 |

TABLE 6-continued

Go term analysis of network interactions in lymphblastoid, ES and RA cells

| Cell type | ModID | GO.ID | Term | Annotated | Significant | Expected | P-value | GOType | EnrichFold |
|---|---|---|---|---|---|---|---|---|---|
| Lymphoblastoid | 9 | 00:0005198 | structural molecule activity | 72 | 5 | 2.38 | 0.023 | MF | 2.10 |
| Lymphoblastoid | 9 | 00:0061024 | membrane organization | 75 | 5 | 2.48 | 0.028 | BP | 2.02 |
| Lymphoblastoid | 9 | 00:0015935 | small ribosomal subunit | 25 | 3 | 0.79 | 0.028 | CC | 3.80 |
| Lymphoblastoid | 9 | 00:0016192 | vesicle-mediated transport | 10 | 2 | 0.33 | 0.036 | BP | 6.06 |
| ES | central cluster | 00:0006413 | translational initiation | 69 | 67 | 58.38 | 0.00021 | BP | 1.15 |
| ES | central cluster | 00:0006614 | SRP-dependent cotranslational protein targeting to membrane | 65 | 63 | 55 | 0.00045 | BP | 1.15 |
| ES | central cluster | 00:0000184 | nuclear-transcribed m RNA catabolic process, nonsense-mediated decay | 64 | 62 | 54.15 | 0.00054 | BP | 1.14 |
| ES | central cluster | 00:0019083 | viral transcription | 63 | 61 | 53.31 | 0.00065 | BP | 1.14 |
| ES | central cluster | 00:0006415 | translational termination | 63 | 61 | 53.31 | 0.00065 | BP | 1.14 |
| ES | central cluster | 00:0070062 | extracellular vesicular exosome | 132 | 122 | 110.59 | 9.30E−05 | CC | 1.10 |
| ES | central cluster | 00:0022625 | cytosolic large ribosomal subunit | 37 | 37 | 31 | 0.00082 | CC | 1.19 |
| ES | central cluster | 00:0005829 | cytosol | 138 | 127 | 115.62 | 0.0039 | CC | 1.10 |
| ES | central cluster | 00:0030529 | ribonucleoprotein complex | 93 | 89 | 77.92 | 0.00536 | CC | 1.14 |
| ES | central cluster | 00:0005925 | focal adhesion | 54 | 51 | 45.24 | 0.00973 | CC | 1.13 |
| ES | central cluster | 00:0044822 | poly(A) RNA binding | 121 | 114 | 102.08 | 1.70E−05 | MF | 1.12 |
| ES | central cluster | 00:0003735 | structural constituent of ribosome | 65 | 62 | 54.84 | 0.002 | MF | 1.13 |
| ES | central cluster | 00:1901265 | nucleoside phosphate binding | 56 | 52 | 47.24 | 0.031 | MF | 1.10 |
| ES | central cluster | 00:0000166 | nucleotide binding | 56 | 52 | 47.24 | 0.031 | MF | 1.10 |
| ES | central cluster | 00:0036094 | small molecule binding | 61 | 56 | 51.46 | 0.045 | MF | 1.09 |
| ES | 1 | 00:0006413 | translational initiation | 69 | 29 | 16.2 | 3.30E−05 | BP | 1.79 |
| ES | 1 | 00:0006614 | SRP-dependent cotranslational protein targeting to membrane | 65 | 27 | 15.26 | 0.00011 | BP | 1.77 |
| ES | 1 | 00:0000184 | nuclear-transcribed mRNA catabolic process, nonsense-mediated decay | 64 | 26 | 15.03 | 0.00026 | BP | 1.73 |
| ES | 1 | 00:0006414 | translational elongation | 68 | 27 | 15.97 | 0.00029 | BP | 1.69 |
| ES | 1 | 00:0022626 | cytosolic ribosome | 62 | 25 | 14.6 | 0.00051 | CC | 1.71 |
| ES | 1 | 00:0019083 | viral transcription | 63 | 25 | 14.79 | 6.00E−04 | BP | 1.69 |
| ES | 1 | 00:0003735 | structural constituent of ribosome | 65 | 25 | 15.51 | 0.0015 | MF | 1.61 |
| ES | 1 | 00:0015935 | small ribosomal subunit | 27 | 12 | 6.36 | 0.00943 | CC | 1.89 |
| ES | 1 | 00:0044822 | poly(A) RNA binding | 121 | 37 | 28.88 | 0.0107 | ME | 1.28 |
| ES | 1 | 00:0044391 | ribosomal subunit | 65 | 26 | 15.31 | 0.01116 | CC | 1.70 |
| ES | 1 | 00:0005576 | extracellular region | 136 | 40 | 32.03 | 0.01382 | CC | 1.25 |
| ES | 1 | 00:0022627 | cytosolic small ribosomal subunit | 25 | 11 | 5.89 | 0.01446 | CC | 1.87 |
| ES | 1 | 00:0003723 | RNA binding | 136 | 40 | 32.46 | 0.0157 | MF | 1.23 |
| ES | 1 | 00:0003676 | nucleic acid binding | 154 | 43 | 36.76 | 0.0348 | MF | 1.17 |
| ES | 2 | 00:0006096 | glycolytic process | 9 | 5 | 1.28 | 0.0036 | BP | 3.91 |
| ES | 2 | 00:0046364 | monosaccharide biosynthetic process | 6 | 4 | 0.85 | 0.0042 | BP | 4.71 |
| ES | 2 | 00:0006952 | defense response | 27 | 9 | 3.83 | 0.006 | BP | 2.35 |
| ES | 2 | 00:0019318 | hexose metabolic process | 11 | 5 | 1.56 | 0.0106 | BP | 3.21 |
| ES | 2 | 00:0006006 | glucose metabolic process | 11 | 5 | 1.56 | 0.0106 | BP | 3.21 |
| ES | 2 | 00:0005615 | extracellular space | 16 | 6 | 2.16 | 0.012 | CC | 2.78 |
| ES | 2 | 00:0005737 | cytoplasm | 218 | 34 | 29.46 | 0.013 | CC | 1.15 |
| ES | 2 | 00:0044444 | cytoplasmic part | 188 | 31 | 25.41 | 0.014 | CC | 1.22 |
| ES | 2 | 00:0072562 | blood microparticle | 5 | 3 | 0.68 | 0.019 | CC | 4.41 |
| ES | 2 | 00:0023023 | MHC protein complex binding | 5 | 3 | 0.7 | 0.021 | MF | 4.29 |
| ES | 2 | 00:0023026 | MHC class II protein complex binding | 5 | 3 | 0.7 | 0.021 | MF | 4.29 |
| ES | 2 | 00:0016491 | oxidoreductase activity | 13 | 5 | 1.82 | 0.022 | MF | 2.75 |
| ES | 2 | 00:0030554 | adenyl nucleotide binding | 24 | 7 | 3.36 | 0.033 | ME | 2.08 |
| ES | 2 | 00:0005829 | cytosol | 138 | 24 | 18.65 | 0.037 | CC | 1.29 |
| ES | 2 | 00:0048037 | cofactor binding | 6 | 3 | 0.84 | 0.037 | MF | 3.57 |
| ES | 3 | 00:0005925 | focal adhesion | 54 | 10 | 4.17 | 0.0024 | CC | 2.40 |
| ES | 3 | 00:0006338 | chromatin remodeling | 6 | 3 | 0.49 | 0.0078 | BP | 6.12 |
| ES | 3 | 00:0010628 | positive regulation of gene expression | 18 | 5 | 1.46 | 0.009 | BP | 3.42 |
| ES | 3 | 00:0031966 | mitochondrial membrane | 14 | 4 | 1.08 | 0.0158 | CC | 3.70 |
| ES | 3 | 00:0008285 | negative regulation of cell proliferation | 8 | 3 | 0.65 | 0.0197 | BP | 4.62 |

TABLE 6-continued

Go term analysis of network interactions in lymphblastoid, ES and RA cells

| Cell type | ModID | GO.ID | Term | Annotated | Significant | Expected | P-value | GOType | EnrichFold |
|---|---|---|---|---|---|---|---|---|---|
| ES | 3 | 00:0005740 | mitochondrial envelope | 15 | 4 | 1.16 | 0.0204 | CC | 3.45 |
| ES | 3 | 00:0010557 | positive regulation of macromolecule biosynthetic process | 23 | 5 | 1.86 | 0.0269 | BP | 2.69 |
| ES | 3 | 00:0016020 | membrane | 149 | 16 | 11.51 | 0.0269 | CC | 1.39 |
| ES | 3 | 00:0045893 | positive regulation of transcription, DNA-templated | 16 | 4 | 1.3 | 0.0303 | BP | 3.08 |
| ES | 4 | 00:0042273 | ribosomal large subunit biogenesis | 5 | 2 | 0.28 | 0.027 | BP | 7.14 |
| ES | 4 | 00:0001890 | placenta development | 5 | 2 | 0.28 | 0.027 | BP | 7.14 |
| ES | 4 | 00:0006364 | rRNA processing | 13 | 3 | 0.74 | 0.03 | BP | 4.05 |
| ES | 4 | 00:0016072 | rRNA metabolic process | 13 | 3 | 0.74 | 0.03 | BP | 4.05 |
| ES | 4 | 00:0034470 | ncRNA processing | 14 | 3 | 0.79 | 0.037 | BP | 3.80 |
| ES | 4 | 00:0044822 | poly(A) RNA binding | 121 | 10 | 6.47 | 0.04 | MF | 1.55 |
| ES | 5 | 00:0033674 | positive regulation of kinase activity | 10 | 3 | 0.69 | 0.024 | BP | 4.35 |
| ES | 5 | 00:0045860 | positive regulation of protein kinase activity | 10 | 3 | 0.69 | 0.024 | BP | 4.35 |
| ES | 5 | 00:0000165 | MAPK cascade | 11 | 3 | 0.76 | 0.032 | BP | 3.95 |
| ES | 5 | 00:0023014 | signal transduction by phosphorylation | 11 | 3 | 0.76 | 0.032 | BP | 3.95 |
| ES | 5 | 00:0043408 | regulation of MAPK cascade | 11 | 3 | 0.76 | 0.032 | BP | 3.95 |
| ES | 5 | 00:0030017 | sarcomere | 5 | 2 | 0.39 | 0.049 | CC | 5.13 |
| ES | 5 | 00:0044449 | contractile fiber part | 5 | 2 | 0.39 | 0.049 | CC | 5.13 |
| ES | 6 | 00:0007600 | sensory perception | 7 | 4 | 0.91 | 0.0062 | BP | 4.40 |
| ES | 6 | 00:0043009 | chordate embryonic development | 13 | 5 | 1.68 | 0.0161 | BP | 2.98 |
| ES | 6 | 00:0009792 | embryo development ending in birth or egg hatching | 13 | 5 | 1.68 | 0.0161 | BP | 2.98 |
| ES | 6 | 00:0030031 | cell projection assembly | 5 | 3 | 0.65 | 0.0166 | BP | 4.62 |
| ES | 6 | 00:0048568 | embryonic organ development | 5 | 3 | 0.65 | 0.0166 | BP | 4.62 |
| ES | 6 | 00:0003697 | single-stranded DNA binding | 6 | 3 | 0.77 | 0.029 | MF | 3.90 |
| ES | 6 | 00:0031252 | cell leading edge | 7 | 3 | 0.89 | 0.046 | CC | 3.37 |
| ES | 7 | 00:0043234 | protein complex | 79 | 9 | 3.36 | 5.00E−04 | CC | 2.68 |
| ES | 7 | 00:0030001 | metal ion transport | 7 | 3 | 0.28 | 0.0016 | BP | 10.71 |
| ES | 7 | 00:0051049 | regulation of transport | 23 | 4 | 0.93 | 0.0083 | BP | 4.30 |
| ES | 7 | 00:0019904 | protein domain specific binding | 13 | 3 | 0.53 | 0.012 | ME | 5.66 |
| ES | 7 | 00:0012505 | endomembrane system | 38 | 5 | 1.61 | 0.0125 | CC | 3.11 |
| ES | 7 | 00:0005794 | Golgi apparatus | 13 | 3 | 0.55 | 0.013 | CC | 5.45 |
| ES | 7 | 00:0003013 | circulatory system process | 5 | 2 | 0.2 | 0.0139 | BP | 10.00 |
| ES | 7 | 00:0008015 | blood circulation | 5 | 2 | 0.2 | 0.0139 | BP | 10.00 |
| ES | 7 | 00:0006308 | DNA catabolic process | 5 | 2 | 0.2 | 0.0139 | BP | 10.00 |
| ES | 7 | 00:0005667 | transcription factor complex | 6 | 2 | 0.25 | 0.0225 | CC | 8.00 |
| ES | 7 | 00:0005515 | protein binding | 170 | 10 | 7 | 0.026 | MF | 1.43 |
| ES | 7 | 00:0005654 | nucleoplasm | 48 | 5 | 2.04 | 0.0341 | CC | 2.45 |
| ES | 7 | 00:0019899 | enzyme binding | 34 | 4 | 1.4 | 0.037 | MF | 2.86 |
| ES | 7 | 00:0008134 | transcription factor binding | 9 | 2 | 0.37 | 0.047 | MF | 5.41 |
| ES | 8 | 00:0009986 | cell surface | 10 | 3 | 0.23 | 0.00079 | CC | 13.04 |
| ES | 8 | 00:0015711 | organic anion transport | 6 | 2 | 0.15 | 0.0071 | BP | 13.33 |
| ES | 8 | 00:0040011 | locomotion | 27 | 3 | 0.66 | 0.0187 | BP | 4.55 |
| ES | 8 | 00:0035770 | ribonucleoprotein granule | 11 | 2 | 0.25 | 0.02247 | CC | 8.00 |
| ES | 8 | 00:0036464 | cytoplasmic ribonucleoprotein granule | 11 | 2 | 0.25 | 0.02247 | CC | 8.00 |
| ES | 8 | 00:0042330 | taxis | 12 | 2 | 0.29 | 0.0292 | BP | 6.90 |
| ES | 8 | 00:0006935 | chemotaxis | 12 | 2 | 0.29 | 0.0292 | BP | 6.90 |
| ES | 8 | 00:0065008 | regulation of biological quality | 59 | 4 | 1.43 | 0.0303 | BP | 2.80 |
| ES | 8 | 00:0030054 | cell junction | 62 | 4 | 1.44 | 0.03061 | CC | 2.78 |
| ES | 8 | 00:0005615 | extracellular space | 16 | 2 | 0.37 | 0.04648 | CC | 5.41 |
| ES | 9 | 00:0003729 | mRNA binding | 9 | 2 | 0.33 | 0.038 | ME | 6.06 |
| ES | 10 | 00:0031124 | mRNA 3'-end processing | 6 | 2 | 0.15 | 0.0071 | BP | 13.33 |
| ES | 10 | 00:0006366 | transcription from RNA polymerase II promoter | 21 | 3 | 0.51 | 0.009 | BP | 5.88 |
| ES | 10 | 00:0003723 | RNA binding | 136 | 6 | 3.36 | 0.029 | MF | 1.79 |
| ES | 10 | 00:0008283 | cell proliferation | 32 | 3 | 0.78 | 0.0302 | BP | 3.85 |
| ES | 10 | 00:0008284 | positive regulation of cell proliferation | 13 | 2 | 0.32 | 0.0341 | BP | 6.25 |
| ES | 10 | 00:0006325 | chromatin organization | 15 | 2 | 0.36 | 0.0449 | BP | 5.56 |
| ES-RA | central cluster | 00:0006414 | translational elongation | 52 | 48 | 35.2 | 1.10E−06 | BP | 1.36 |
| ES-RA | central cluster | 00:0006413 | translational initiation | 55 | 50 | 37.23 | 2.10E−06 | BP | 1.34 |
| ES-RA | central cluster | 00:0000184 | nuclear-transcribed mRNA catabolic process, nonsense-mediated decay | 50 | 46 | 33.84 | 3.00E−06 | BP | 1.36 |
| ES-RA | central cluster | 00:0006415 | translational termination | 50 | 46 | 33.84 | 3.00E−06 | BP | 1.36 |
| ES-RA | central cluster | 00:0019083 | viral transcription | 49 | 45 | 33.16 | 4.80E−06 | BP | 1.36 |
| ES-RA | central cluster | 00:0070062 | extracellular vesicular exosome | 79 | 66 | 52.37 | 8.20E−06 | CC | 1.26 |
| ES-RA | central cluster | 00:0005829 | cytosol | 79 | 70 | 52.37 | 0.00046 | CC | 1.34 |

TABLE 6-continued

Go term analysis of network interactions in lymphblastoid, ES and RA cells

| Cell type | ModID | GO.ID | Term | Annotated | Significant | Expected | P-value | GOType | EnrichFold |
|---|---|---|---|---|---|---|---|---|---|
| ES-RA | central cluster | 00:0022627 | cytosolic small ribosomal subunit | 20 | 19 | 13.26 | 0.00192 | CC | 1.43 |
| ES-RA | central cluster | 00:0022625 | cytosolic large ribosomal subunit | 29 | 26 | 19.22 | 0.00203 | CC | 1.35 |
| ES-RA | central cluster | 00:0005925 | focal adhesion | 37 | 32 | 24.53 | 0.00211 | CC | 1.30 |
| ES-RA | central cluster | 00:0044822 | poly(A) RNA binding | 75 | 65 | 49.54 | 1.50E−07 | MF | 1.31 |
| ES-RA | central cluster | 00:0003735 | structural constituent of ribosome | 50 | 45 | 33.02 | 6.30E−06 | MF | 1.36 |
| ES-RA | central cluster | 00:0005515 | protein binding | 104 | 79 | 68.69 | 0.00037 | MF | 1.15 |
| ES-RA | central cluster | GO:0003723 | RNA binding | 85 | 73 | 56.14 | 0.03459 | MF | 1.30 |
| ES-RA | central cluster | 00:0019843 | rRNA binding | 7 | 7 | 4.62 | 0.05118 | MF | 1.52 |
| ES-RA | 1 | 00:0070062 | extracellular vesicular exosome | 79 | 20 | 12.19 | 0.00099 | CC | 1.64 |
| ES-RA | 1 | GO:0006414 | translational elongation | 52 | 16 | 8.56 | 0.0012 | BP | 1.87 |
| ES-RA | 1 | 00:0022626 | cytosolic ribosome | 49 | 14 | 7.56 | 0.00382 | CC | 1.85 |
| ES-RA | 1 | 00:0016071 | mRNA metabolic process | 62 | 10 | 10.21 | 0.0044 | BP | 1.86 |
| ES-RA | 1 | 00:0044391 | ribosomal subunit | 50 | 14 | 7.71 | 0.00481 | CC | 1.82 |
| ES-RA | 1 | 00:0044822 | poly(A) RNA binding | 75 | 19 | 12.5 | 0.0054 | MF | 1.52 |
| ES-RA | 1 | 00:0019083 | viral transcription | 49 | 14 | 8.07 | 0.0076 | BP | 1.73 |
| ES-RA | 1 | 00:0006614 | SRP-dependent cotranslational protein targeting to membrane | 49 | 14 | 8.07 | 0.0076 | BP | 1.73 |
| ES-RA | 1 | 00:0046907 | intracellular transport | 68 | 20 | 11.2 | 0.0077 | BP | 1.79 |
| ES-RA | 1 | 00:0003735 | structural constituent of ribosome | 50 | 14 | 8.33 | 0.0107 | MF | 1.68 |
| ES-RA | 1 | 00:0022625 | cytosolic large ribosomal subunit | 29 | 9 | 4.47 | 0.01599 | CC | 2.01 |
| ES-RA | 1 | 00:0015934 | large ribosomal subunit | 29 | 9 | 4.47 | 0.01599 | CC | 2.01 |
| ES-RA | 1 | 00:0005198 | structural molecule activity | 58 | 15 | 9.67 | 0.0181 | MF | 1.55 |
| ES-RA | 2 | 00:0043412 | macromolecule modification | 26 | 5 | 1.59 | 0.0099 | BP | 3.14 |
| ES-RA | 2 | 00:0003824 | catalytic activity | 31 | 5 | 1.91 | 0.023 | MF | 2.62 |
| ES-RA | 2 | 00:0006464 | cellular protein modification process | 24 | 4 | 1.46 | 0.0408 | BP | 2.74 |
| ES-RA | 2 | 00:0036211 | protein modification process | 24 | 4 | 1.46 | 0.0408 | BP | 2.74 |
| ES-RA | 2 | 00:0045892 | negative regulation of transcription, DNA-templated | 14 | 3 | 0.85 | 0.0418 | BP | 3.53 |
| ES-RA | 2 | 00:1902679 | negative regulation of RNA biosynthetic process | 14 | 3 | 0.85 | 0.0418 | BP | 3.53 |
| ES-RA | 3 | 00:0042060 | wound healing | 8 | 4 | 0.88 | 0.0055 | BP | 4.55 |
| ES-RA | 3 | 00:0042383 | sarcolemma | 5 | 3 | 0.51 | 0.0081 | CC | 5.88 |
| ES-RA | 3 | 00:0048646 | anatomical structure formation involved in morphogenesis | 9 | 4 | 0.99 | 0.0092 | BP | 4.04 |
| ES-RA | 3 | 00:0051146 | striated muscle cell differentiation | 5 | 3 | 0.55 | 0.0098 | BP | 5.45 |
| ES-RA | 3 | 00:0001101 | response to acid chemical | 5 | 3 | 0.55 | 0.0098 | BP | 5.45 |
| ES-RA | 3 | 00:0010035 | response to inorganic substance | 5 | 3 | 0.55 | 0.0098 | BP | 5.45 |
| ES-RA | 3 | 00:0065010 | extracellular membrane-bounded organelle | 79 | 13 | 8.13 | 0.0141 | CC | 1.60 |
| ES-RA | 3 | 00:0043230 | extracellular organelle | 79 | 13 | 8.13 | 0.0141 | CC | 1.60 |
| ES-RA | 3 | 00:0070062 | extracellular vesicular exosome | 79 | 13 | 8.13 | 0.0141 | CC | 1.60 |
| ES-RA | 3 | 00:0044421 | extracellular region part | 80 | 13 | 8.23 | 0.0161 | CC | 1.58 |
| ES-RA | 4 | 00:0044391 | ribosomal subunit | 50 | 11 | 4.57 | 0.00055 | CC | 2.41 |
| ES-RA | 4 | 00:0022626 | cytosolic ribosome | 49 | 10 | 4.48 | 0.00266 | CC | 2.23 |
| ES-RA | 4 | 00:0006413 | translational initiation | 55 | 11 | 5.37 | 0.0027 | BP | 2.05 |
| ES-RA | 4 | 00:0006614 | SRP-dependent cotranslational protein targeting to membrane | 49 | 10 | 4.78 | 0.0046 | BP | 2.09 |
| ES-RA | 4 | 00:0019083 | viral transcription | 49 | 10 | 4.78 | 0.0046 | BP | 2.09 |
| ES-RA | 4 | 00:0006415 | translational termination | 50 | 10 | 4.88 | 0.0055 | BP | 2.05 |
| ES-RA | 4 | 00:0000184 | nuclear-transcribed mRNA catabolic process, nonsense-mediated decay | 50 | 10 | 4.88 | 0.0055 | BP | 2.05 |
| ES-RA | 4 | 00:0003735 | structural constituent of ribosome | 50 | 10 | 4.94 | 0.0061 | MF | 2.02 |
| ES-RA | 4 | 00:0003723 | RNA binding | 85 | 13 | 8.4 | 0.0133 | MF | 1.55 |
| ES-RA | 4 | 00:0015935 | small ribosomal subunit | 21 | 5 | 1.92 | 0.02772 | CC | 2.60 |
| ES-RA | 4 | 00:0005829 | cytosol | 79 | 14 | 7.22 | 0.02827 | CC | 1.94 |
| ES-RA | 4 | 00:0030055 | cell-substrate junction | 37 | 7 | 3.38 | 0.02854 | CC | 2.07 |
| ES-RA | 4 | 00:0003676 | nucleic acid binding | 104 | 14 | 10.27 | 0.0323 | MF | 1.36 |
| ES-RA | 5 | 00:0006413 | translational initiation | 55 | 8 | 2.68 | 0.00011 | BP | 2.99 |
| ES-RA | 5 | 00:0022627 | cytosolic small ribosomal subunit | 20 | 5 | 0.91 | 0.00053 | CC | 5.49 |
| ES-RA | 5 | 00:0019083 | viral transcription | 49 | 7 | 2.39 | 0.00095 | BP | 2.93 |
| ES-RA | 5 | 00:0006614 | SRP-dependent cotranslational protein targeting to membrane | 49 | 7 | 2.39 | 0.00095 | BP | 2.93 |
| ES-RA | 5 | 00:0000184 | nuclear-transcribed mRNA catabolic process, nonsense-mediated decay | 50 | 7 | 2.44 | 0.00109 | BP | 2.87 |
| ES-RA | 5 | 00:0006415 | translational termination | 50 | 7 | 2.44 | 0.00109 | BP | 2.87 |
| ES-RA | 5 | 00:0003735 | structural constituent of ribosome | 50 | 7 | 2.47 | 0.0012 | MF | 2.83 |
| ES-RA | 5 | 00:0044822 | poly(A) RNA binding | 75 | 8 | 3.7 | 0.0017 | MF | 2.16 |

TABLE 6-continued

Go term analysis of network interactions in lymphblastoid, ES and RA cells

| Cell type | ModID | GO.ID | Term | Anno-tated | Signif-icant | Ex-pected | P-value | GOType | EnrichFold |
|---|---|---|---|---|---|---|---|---|---|
| ES-RA | 5 | 00:0030529 | ribonucleoprotein complex | 68 | 8 | 3.11 | 0.02842 | CC | 2.57 |
| ES-RA | 5 | 00:0003729 | mRNA binding | 6 | 2 | 0.3 | 0.0291 | MF | 6.67 |
| ES-RA | 6 | 00:0003723 | RNA binding | 85 | 5 | 2.62 | 0.038 | MF | 1.91 |
| ES-RA | 8 | 00:0006006 | glucose metabolic process | 5 | 3 | 0.18 | 0.00027 | BP | 16.67 |
| ES-RA | 8 | 00:0016051 | carbohydrate biosynthetic process | 5 | 3 | 0.18 | 0.00027 | BP | 16.67 |
| ES-RA | 8 | 00:0006091 | generation of precursor metabolites and energy | 7 | 3 | 0.26 | 0.00092 | BP | 11.54 |
| ES-RA | 8 | 00:0005886 | plasma membrane | 28 | 4 | 0.96 | 0.0064 | CC | 4.17 |
| ES-RA | 8 | 00:0044712 | single-organism catabolic process | 13 | 3 | 0.48 | 0.00687 | BP | 6.25 |
| ES-RA | 8 | 00:0044281 | small molecule metabolic process | 27 | 4 | 0.99 | 0.0071 | BP | 4.04 |
| ES-RA | 8 | 00:0015629 | actin cytoskeleton | 5 | 2 | 0.17 | 0.0094 | CC | 11.76 |
| ES-RA | 8 | 00:0008092 | cytoskeletal protein binding | 12 | 2 | 0.37 | 0.045 | ME | 5.41 |
| ES-RA | 8 | 00:0003824 | catalytic activity | 31 | 3 | 0.96 | 0.049 | MF | 3.13 |
| ES-RA | 9 | 00:0019843 | rRNA binding | 7 | 2 | 0.26 | 0.022 | MF | 7.69 |
| ES-RA | 9 | 00:0048518 | positive regulation of biological process | 44 | 4 | 1.61 | 0.045 | BP | 2.48 |
| ES-RA | 10 | 00:0010608 | posttranscriptional regulation of gene expression | 17 | 3 | 0.52 | 0.0082 | BP | 5.77 |
| ES-RA | 10 | 00:0006446 | regulation of translational initiation | 6 | 2 | 0.18 | 0.0107 | BP | 11.11 |
| ES-RA | 10 | 00:0051248 | negative regulation of protein metabolic process | 10 | 2 | 0.3 | 0.0304 | BP | 6.67 |
| ES-RA | 10 | 00:0032269 | negative regulation of cellular protein metabolic process | 10 | 2 | 0.3 | 0.0304 | BP | 6.67 |
| ES-RA | 10 | 00:0051129 | negative regulation of cellular component organization | 10 | 2 | 0.3 | 0.0304 | BP | 6.67 |
| ES-RA | 10 | 00:0019901 | protein kinase binding | 11 | 2 | 0.34 | 0.038 | MF | 5.88 |
| ES-RA | 10 | 00:0019900 | kinase binding | 12 | 2 | 0.37 | 0.045 | MF | 5.41 |
| ES-RA | 11 | 00:0010557 | positive regulation of macromolecule biosynthetic process | 14 | 2 | 0.34 | 0.037 | BP | 5.88 |
| ES-RA | 12 | 00:0030001 | metal ion transport | 5 | 2 | 0.09 | 0.0022 | BP | 22.22 |
| ES-RA | 12 | 00:0006875 | cellular metal ion homeostasis | 6 | 2 | 0.11 | 0.0033 | BP | 18.18 |
| ES-RA | 12 | 00:0046872 | metal ion binding | 30 | 3 | 0.56 | 0.0058 | MF | 5.36 |
| ES-RA | 12 | 00:0019904 | protein domain specific binding | 9 | 2 | 0.17 | 0.008 | MF | 11.76 |
| ES-RA | 12 | 00:0012505 | endomembrane system | 25 | 3 | 0.57 | 0.0095 | CC | 5.26 |
| ES-RA | 12 | 00:0022892 | substrate-specific transporter activity | 10 | 2 | 0.19 | 0.01 | MF | 10.53 |
| ES-RA | 12 | 00:0005768 | endosome | 8 | 2 | 0.18 | 0.0105 | CC | 11.11 |
| ES-RA | 12 | 00:0007154 | cell communication | 40 | 3 | 0.73 | 0.0137 | BP | 4.11 |
| ES-RA | 12 | 00:0044700 | single organism signaling | 40 | 3 | 0.73 | 0.0137 | BP | 4.11 |
| ES-RA | 12 | 00:0023052 | signaling | 40 | 3 | 0.73 | 0.0137 | BP | 4.11 |
| ES-RA | 12 | 00:0005783 | endoplasmic reticulum | 10 | 2 | 0.23 | 0.0167 | CC | 8.70 |
| ES-RA | 12 | 00:0005215 | transporter activity | 13 | 2 | 0.24 | 0.0171 | MF | 8.33 |
| ES-RA | 12 | 00:0065010 | extracellular membrane-bounded organelle | 79 | 4 | 1.81 | 0.0398 | CC | 2.21 |
| ES-RA | 12 | 00:0043230 | extracellular organelle | 79 | 4 | 1.81 | 0.0398 | CC | 2.21 |

TABLE 7

Probes and qPCR primers used in validation

| Type | Gene | Position | |
|---|---|---|---|
| Probe | Human 18S | R1 | /5Biosg/ CTGGCAGGATCAACCAGGTA (SEQ ID NO: 3) |
| | | R711 | /5Biosg/GGGCGGTGGCTCGCCTCGCG (SEQ ID NO: 4) |
| | | R1661 | /5Biosg/TGACCCGCACTTACTGGGAA (SEQ ID NO: 5) |
| | | R1868 | /5Biosg/AATGATCCTTCCGCAGGTTCA (SEQ ID NO: 6) |
| Probe | Human 28S | R1 | /5Biosg/ ACGTCTGATCTGAGGTCGCG (SEQ ID NO: 7) |
| | | R1311 | /5Biosg/TGGTCCGTGTTTCAAGACGGGT (SEQ ID NO: 8) |
| | | R1737 | /5Biosg/CAAGACCTCTAATCATTCGCTT (SEQ ID NO: 9) |
| | | R5058 | /5Biosg/TGTCGAGGGCTGACTTTCAAT (SEQ ID NO: 10) |
| Probe | Human 5S | R58 | /5Biosg/TGCTTAGCTTCCGAGATCAGA (SEQ ID NO: 11) |
| | | R120 | /5Biosg/AAGCCTACAGCACCCGGTATT (SEQ ID NO: 12) |
| Probe | ACA51 | R13 | /5Biosg/GTAAGAACACAGCCTGTGGTAAG (SEQ ID NO: 13) |
| | | R37 | /5Biosg/ TCCTCTTTCTATACAGTCAG (SEQ ID NO: 14) |
| | | R60 | /5Biosg/ ATATGGGGTAGGTTTACTCT (SEQ ID NO: 15) |
| Probe | TMSB4X | R52 | /5Biosg/GAGGAAAAGCGAAGCGAGGC (SEQ ID NO: 16) |
| | | R241 | /5Biosg/GCGAATGCTTGTGGAATGTA (SEQ ID NO: 17) |
| | | R302 | /5Biosg/AACTTGATCCAACCTCTTTG (SEQ ID NO: 18) |

TABLE 7-continued

Probes and qPCR primers used in validation

| Type | Gene | Position | | |
|---|---|---|---|---|
| Probe | EEF1A1 | R2 | /5Biosg/GGCAAACCCGTTGCGAAAAA | (SEQ ID NO: 19) |
|  |  | R29 | /5Biosg/TAGTTTTCACGACACCTGTG | (SEQ ID NO: 20) |
|  |  | R1547 | /5Biosg/ACCACTGATTAAGAGTGGGG | (SEQ ID NO: 21) |
| Probe | Actin | R435 | /5Biosg/ACATGATCTGGGTCATCTTC | (SEQ ID NO: 22) |
|  |  | R488 | /5Biosg/GGATAGCACAGCCTGGATAG | (SEQ ID NO: 23) |
|  |  | R745 | /5Biosg/ATCTCTTGCTCGAAGTCCAG | (SEQ ID NO: 24) |
|  |  | R823 | /5Biosg/TCATTGCCAATGGTGATGAC | (SEQ ID NO: 25) |
|  |  | R1067 | /5Biosg/CTCAGGAGGAGCAATGATCT | (SEQ ID NO: 26) |
|  |  | R1400 | /5Biosg/CACATTGTGAACTTTGGGGG | (SEQ ID NO: 27) |
|  |  | R1475 | /5Biosg/GACTTCCTGTAACAACGCAT | (SEQ ID NO: 28) |
|  |  | R1761 | /5Biosg/GTCTCAAGTCAGTGTACAGG | (SEQ ID NO: 29) |
| Probe | Yeast YBR118W | R1 | /5Biosg/ACCCATGTTTAGTTAATTAT | (SEQ ID NO: 30) |
|  |  | R45 | /5Bi0sg/TCGACATGACCGATAACGAC | (SEQ ID NO: 31) |
|  |  | R97 | /5Biosg/ACCACCACACTTGTAAATCA | (SEQ ID NO: 32) |
| Probe | GFP Bio control 1 |  | /5Biosg/CACGGATTATTTGCCTGATT | (SEQ ID NO: 33) |
| Probe | GFP Bio control 2 |  | /5Biosg/ATTTTGCGTAACCTATTCGC | (SEQ ID NO: 34) |
| QPCR primer | Human 18S | F1443 | TTAGAGGGACAAGTGGCGTT | (SEQ ID NO: 35) |
|  |  | R1513 | GGACATCTAAGGGCATCACA | (SEQ ID NO: 36) |
| QPCR primer | Human 28S | F2377 | GAGAACTTTGAAGGCCGAAG | (SEQ ID NO: 37) |
|  |  | R2455 | CATCTCTCAGGACCGACTGA | (SEQ ID NO: 38) |
| QPCR primer | Human 5S | F25 | GCGCCCGATCTCGTCTGATCTC | (SEQ ID NO: 39) |
|  |  | R77 | CAGGCGGTCTCCCATCCAAGT | (SEQ ID NO: 40) |
| QPCR primer | ACA51 | F20 | CAGGCTGTGTTCTTACACTGAC | (SEQ ID NO: 41) |
|  |  | R109 | ATGTTCCCCATTCACAATACA | (SEQ ID NO: 42) |
| QPCR primer | SNORA32 | F2 | GGTCATTACCAAGGCTTTTAG | (SEQ ID NO: 43) |
|  |  | R67 | GCAGATAGAAAACCTACTGGG | (SEQ ID NO: 44) |
| QPCR primer | SNORD83a | F19 | TCAGAGTGAGCGCTGGGTACAG | (SEQ ID NO: 45) |
|  |  | R63 | GGAAGGCAGTAGAGAATGGT | (SEQ ID NO: 46) |
| QPCR primer | TMSB4X | F95 | CGATATGGCTGAGATCGAGA | (SEQ ID NO: 47) |
|  |  | R158 | CTTTGGAAGGCAGTGGATTT | (SEQ ID NO: 48) |
| QPCR primer | EEF1A1 | F1010 | CTGTCAAGGATGTTCGTCGT | (SEQ ID NO: 49) |
|  |  | R1105 | CTTATTTGGCCTGGATGGTT | (SEQ ID NO: 50) |
| QPCR primer | RPS27 | F42 | TCGCAAAGGATCTCCTTCAT | (SEQ ID NO: 51) |
|  |  | R89 | CCAGGCGTTTCTTCTTGTG | (SEQ ID NO: 52) |
| QPCR primer | RPLP0 | F865 | ACTCTGCATTCTCGCTTCCT | (SEQ ID NO: 53) |
|  |  | R960 | CTCGTTTGTACCCGTTGATG | (SEQ ID NO: 54) |
| QPCR primer | GAPDH | F787 | TGGTATCGTGGAAGGACTCA | (SEQ ID NO: 55) |
|  |  | R899 | CCAGTAGAGGCAGGGATGAT | (SEQ ID NO: 56) |
| QPCR primer | Actin | F266 | AGAGAGGCATCCTCACCCT | (SEQ ID NO: 57) |
|  |  | R353 | CACACGCAGCTCATTGTAGA | (SEQ ID NO: 58) |
| QPCR primer | RPL35 | F89 | GAAGGAGGAGCTGCTGAAAC | (SEQ ID NO: 59) |
|  |  | R174 | TCGGATCTTAGAGAGCTTGGA | (SEQ ID NO: 60) |
| QPCR primer | B2M | F376 | GACTTTGTCACAGCCCAAGA | (SEQ ID NO: 61) |
|  |  | R467 | CAAGCAAGCAGAATTTGGAA | (SEQ ID NO: 62) |
| QPCR primer | EIF5A | F1033 | GAATCAGAAAGCGGTGGATT | (SEQ ID NO: 63) |
|  |  | R1079 | ACCAGACCAGGGATGAGTG | (SEQ ID NO: 64) |
| QPCR primer | Yeast YBR118W | F14 | CATGGGTAAAGAGAAGTCTCACA | (SEQ ID NO: 65) |
|  |  | R107 | GGTTCTCTTGTCAATACCACCA | (SEQ ID NO: 66) |
|  |  | F1276 | GATTCGCTGTCAGAGACATGA | (SEQ ID NO: 67) |
|  |  | R1349 | CAGCCTTGGTAACCTTAGCG | (SEQ ID NO: 68) |
| QPCR primer | OCT4 | F1764 | GAGAAGGATGTGGTCCGAGT | (SEQ ID NO: 69) |
|  |  | R1836 | GTGCATAGTCGCTGCTTGAT | (SEQ ID NO: 70) |

TABLE 7-continued

Probes and qPCR primers used in validation

| Type | Gene | Position | |
|---|---|---|---|
| QPCR primer | HMGA1 | F609 | GCTGGTAGGGAGTCAGAAGG (SEQ ID NO: 71) |
| | | R739 | TTGGTTTCCTTCCTGGAGTT (SEQ ID NO:72) |
| QPCR primer | GAPDH | F1056 | TCAAGAAGGTGGTGAAGCAG (SEQ ID NO: 73) |
| | | R1129 | CGCTGTTGAAGTCAGAGGAG (SEQ ID NO: 74) |

The invention claimed is:

1. A method of analysing ribonucleic acid-ribonucleic acid (RNA-RNA) interactions comprising:
   a. cross-linking base-paired nucleotides within at least one RNA molecule and/or base-paired nucleotides between at least one pair of RNA molecules using a reversible cross-linking agent comprising a tag to produce at least one cross-linked RNA molecule and/or at least one pair of cross-linked RNA molecules comprising said tag;
   b. fragmenting the said cross-linked RNA molecule and/or pair of cross-linked RNA molecules using metal ion hydrolysis to produce a plurality of fragments of cross-linked RNA molecule and/or pair of cross-linked RNA molecules
   c. using said tag to extract said cross-linked RNA molecule and/or pair of cross-linked RNA molecules obtained from the preceding step;
   d. ligating together ends of said cross-linked RNA fragment(s) to produce cross-linked ligated RNA chimera(s) wherein the ligating does not comprise the use of a linker between the RNA fragment(s);
   e. reversing the cross-linking of the said RNA molecule and/or pair of RNA molecules to produce a ligated RNA chimera molecule(s) and/or RNA chimera pair(s);
   f. sequencing the ligated RNA chimera molecule(s) or pair(s) to generate a sequence library; and
   g. analysing the sequence library to determine RNA-RNA interactions wherein the method does not comprise analysing RNA-RNA interactions through their association with an RNA binding protein.

2. The method according to claim 1 wherein said at least one RNA molecule and/or at least one pair of RNA molecules is present in a cell and said cross-linking using said reversible cross-linking agent involves the use of a cellular uptake agent, such as a detergent, optionally wherein the cell is mammalian, human, bacterial or yeast.

3. The method according to claim 1 wherein part c is undertaken before part b.

4. The method according to claim 1 wherein said cross-linking agent comprises a furocoumarin compound, optionally wherein the cross-linking agent comprises psoralen.

5. The method according to claim 1 wherein said tag comprises a first member of a binding pair selected from the group comprising: biotin/streptavidin, antigen/antibody, protein/protein, polypeptide/protein and polypeptide/polypeptide.

6. The method according to claim 1 wherein the step of cross-linking said RNA molecule(s) with a cross-linking agent to produce cross-linked RNA molecule(s) is carried out using ultraviolet irradiation at wavelengths in the range of about 300 nm to about 400 nm.

7. The method according claim 1 wherein the step of reversing the cross-linking of the cross-linked ligated RNA molecule(s) is carried out using ultraviolet irradiation at wavelengths in the range of about 200 nm to no more than about 300 nm.

8. The method according to claim 1 wherein the step of sequencing the ligated RNA chimera molecule or pairs to generate a sequence library comprises attaching an adaptor sequence to the ligated RNA chimera molecule or pairs.

9. The method according to claim 1 wherein the step of fragmenting the cross-linked RNA molecule and/or pair of RNA molecules to produce a plurality of fragments comprises producing fragments having an average size in the range of 100 to 500 base pairs in length.

10. The method according to claim 1 wherein the cross-linking agent is used at a concentration for crosslinking at approximately one in every 150 bases.

11. The method according to claim 1 wherein the method further comprises removing continuous pairwise interactions or those spaced apart by less than 50 bases from the analysis to focus the analysis on the long-range intramolecular and intermolecular interactions.

12. The method according to claim 1 wherein said RNA molecule and/or at least one member of said pair of RNA molecules is ascribed a "circularization score" defined as the average base pair interaction distance within each molecule, normalized by the length of said RNA molecule or the length of said member of said pair of RNA molecules, optionally wherein said RNA molecule and/or said at least one member of said pair of RNA molecules are classified into groups according to their "circularization score".

13. The method according to claim 1, the method further comprising exposing said RNA molecule and/or pair of RNA molecules to a drug and attributing an efficacy score to the drug based on the determined RNA-RNA interactions.

14. The method according to claim 1, wherein the step of sequencing the ligated RNA chimera molecule or pairs to generate a sequence library comprises reverse-transcribing the ligated RNA chimera molecule or pairs to produce complementary DNA (cDNA).

15. The method according to claim 14, the method further comprising circularizing the cDNA.

16. The method according to claim 14, the method further comprising amplifying the cDNA by polymerase chain reaction (PCR).

17. The method according to claim 1, wherein the tag comprises a biotin tag.

* * * * *